(12) United States Patent
Wegst et al.

(10) Patent No.: US 8,877,498 B2
(45) Date of Patent: Nov. 4, 2014

(54) POROUS POLYMER SCAFFOLDS FOR NEURAL TISSUE ENGINEERING AND METHODS OF PRODUCING THE SAME

(75) Inventors: Ulrike G.K. Wegst, Philadelphia, PA (US); Margaret Wheatley, Media, PA (US); Benjamin W. Riblett, Ardentown, DE (US); Nicola Francis, Hamilton Parish (BM); Amalie Elizabeth Donius, Alfred Station, NY (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/309,280

(22) Filed: Dec. 1, 2011

(65) Prior Publication Data
US 2012/0149111 A1 Jun. 14, 2012

Related U.S. Application Data

(60) Provisional application No. 61/418,776, filed on Dec. 1, 2010, provisional application No. 61/474,636, filed on Apr. 12, 2011.

(51) Int. Cl.
*C12N 5/00* (2006.01)
*C12N 5/0793* (2010.01)

(52) U.S. Cl.
CPC .......... *C12N 5/0619* (2013.01); *C12N 2533/74* (2013.01); *C12N 2533/72* (2013.01); *C12N 2533/52* (2013.01); *C12N 2537/00* (2013.01); *C12N 2533/54* (2013.01); *C12N 2533/32* (2013.01)
USPC ....................................................... 435/395

(58) Field of Classification Search
USPC ........................................................ 435/395
See application file for complete search history.

(56) References Cited

PUBLICATIONS

Deville et al. Freeze Casting of Hydroxyapatite Scaffolds for Bone Tissue Engineering; Biomaterials, vol. 27 (2006) pp. 5480-5489.*
Wegst et al. Biomaterials by Freeze Casting; Philosophical Transactions of the Royal Society A; vol. 368 (Mar. 22, 2919) pp. 2099-2121.*
Zhang et al. Aligned Porous Structures by Directional Freezing; Advanced Materials, vol. 19 (2007) pp. 1529-1533.*
Yang et al. The Design of Scaffolds for Use in Tissue Engineering. Part I. Traditional Factors; Tissue Engineering, vol. 7, No. 6 (2001) pp. 679-689.*
Madaghiele et al. Collagen-Based Matrices With Axially Oriented Pores; Journal of Biomedical Materials REsearch, Part A, vol. 85 (2008) pp. 757-767.*
Ashby, "Hybrids to fill holes in material property space." 2005, Philosophical Magazine 85(26): 3235-3257.

Bakshi, A., et al., "Mechanically engineered hydrogel scaffolds for axonal growth and angiogenesis after transplantation in spinal cord injury." 2004, Journal of Neurosurgery: Spine 1(3):322-329.
Bilston, L. et al., "The mechanical properties of the human cervical spinal cord In Vitro" 1995, Annals of Biomedical Engineering 24(0):67-74.
Bozkurt, et al., "In vitro assessment of axonal growth using dorsal root ganglia explants in a novel three-dimensional collagen matrix." 2007, Tissue Engineering 13(12):2971-2979.
Bozkurt, et al., "In vitro cell alignment obtained with a Schwann cell enriched microstructured nerve guide with longitudinal guidance channels." 2009, Biomaterials 30(2):169-179.
Butler, "Instability Formation and Directional Dendritic Growth of Ice Studied by Optical Interferometry" 2001, Crystal Growth & Design 1(3): 213-223.
Chino, et al., "Directionally freeze-cast titanium foam with aligned, elongated pores." 2008, Acta Materialia, 56(1):105-113.
Crowe, M.J., et al., "Apoptosis and delayed degeneration after spinal cord injury in rats and monkeys." 1997, Nat Med 3(1):73-76.
Dalton, P.D., et al., "Manufacture of poly(2-hydroxyethyl methacrylate-co-methyl methacrylate) hydrogel tubes for use as nerve guidance channels." 2002, Biomaterials 23(18):3843-3851.
Deville, et al., "Freeze casting of hydroxyapatite scaffolds for bone tissue engineering." 2006, Biomaterials, 27(32):5480-5489.
Deville, et al., "Freezing as a path to build complex composites." 2006, Science 311(5760):515-518.
Deville, et al., "Ice-templated porous alumina structures." 2007, Acta Materialia 55(6):1965-1974.
Deville, et al., "In Situ X-Ray Radiography and Tomography Observations of the Solidification of Aqueous Alumina Particle Suspensions—Part I: Initial Instants" 2009, Journal of the American Ceramic Society 92(11): 2489-2496.
Deville, et al., "In Situ X-Ray Radiography and Tomography Observations of the Solidification of Aqueous Alumina Particles Suspensions. Part II: Steady State" 2009, Journal of the American Ceramic Society 92(11): 2497-2503.
Ezekwo et al., "On the mechanism of dewatering colloidal aqueous solutions by freeze-thaw processes." 1980, Water Research 14:1079-1088.

(Continued)

*Primary Examiner* — Susan Hanley
*Assistant Examiner* — Paul Martin
(74) *Attorney, Agent, or Firm* — Saul Ewing LLP; Kathryn Doyle; Brian R. Landry

(57) ABSTRACT

The present invention relates to scaffolds that can physically guide cells, e.g. neurons, while best matching the material properties of native tissue. The present invention also relates to methods of generating such scaffolds, and for the use of such scaffolds, e.g. in spinal cord and peripheral nerve injury repair. The methods of the present invention include a uniquely controlled freeze casting process to generate highly porous, linearly oriented scaffolds. The scaffolds of the present invention not only comprise a highly aligned porosity, but also contain secondary guidance structures in the form of ridges running parallel to the pores to create a series of microstructured and highly aligned channels. This hierarchy of structural guidance aligns and guides neurite outgrowth down the channels created by the ridges, and keep neurites from branching perpendicular to the inter-ridge grooves.

12 Claims, 37 Drawing Sheets

(56) References Cited

PUBLICATIONS

Fukasawa, et al. "Pore structure of porous ceramics synthesized from water-based slurry by freeze-dry process.", 2001, Journal of Materials Science 36(10):2523-2527.

Fukasawa, et al., "Synthesis of Porous Ceramics with Complex Pore Structure by Freeze-Dry Processing." 2001, Journal of the American Ceramic Society 84(1):230-232.

Fukasawa, et al., "Synthesis of Porous Silicon Nitride with Unidirectionally Aligned Channels Using Freeze-Drying Process," 2002, Journal of the American Ceramic Society 85(9): 2151-2155.

Guest, et al., "Demyelination and Schwann cell responses adjacent to injury epicenter cavities following chronic human spinal cord injury." 2005, Experimental Neurology 192(2):384-393.

Horky, L.L., et al., Fate of endogenous stem/progenitor cells following spinal cord injury.: 2006, The Journal of Comparative Neurology 498(4):525-538.

Hung, T.-K., et al., "Stress-strain relationship of the spinal cord of anesthetized cats.".1981, Journal of Biomechanics 14(4): 269-276.

Leipzig, N. et al., "The effect of substrate stiffness on adult neural stem cell behavior." 2009, Biomaterials 30(36):6867-6878.

Madigan, N., et al., "Current tissue engineering and novel therapeutic approaches to axonal regeneration following spinal cord injury using polymer scaffolds." 2009, Respiratory Physiology & Neurobiology 169(2)183-199.

Meghri, et al., "Directionally solidified biopolymer scaffolds: Mechanical properties and endothelial cell responses" 2010, JOM-J Min Met Mat S 62 (7):71-75.

Miyawaki, et al., "Analysis of Ice Structure Formed in Frozen Agar Gel." 2004, Food Science and Technology Research 10(4):437-441.

Nunamaker, et al., "Investigation of the material properties of alginate for the development of hydrogel repair of dura mater." 2011, J Mech Behav Biomed 4:16-33.

Oudega, M., et al., "Axonal regeneration into Schwann cell grafts within resorbable poly(alpha-hydroxyacid) guidance channels in the adult rat spinal cord." 2001, Biomaterials 22(10):1125-1136.

Ozawa et al., "Comparison of spinal cord gray matter and white matter softness: measurement by pipette aspiration method," 2001, J Neurosurg 95(2 Suppl):221-224.

Ozawa, H., et al., "Mechanical properties and function of the spinal pia mater." 2004, J Neurosurg Spine 1(1):122-7.

Pattani, et al., "Immunological effects and membrane interactions of chitosan nanoparticles." 2009, Mol. Pharmaceutics 6 (2):345-352.

Schoof, et al., "Dendritic ice morphology in unidirectionally solidified collagen suspensions." 2000, Journal of Crystal Growth 209(1): 122-129.

Schoof, et al., "Control of pore structure and size in freeze-dried collagen sponges." 2001, Journal of Biomedical Materials Research 58(4): 352-357.

Sobani, et al., "Stem cells for spinal cord regeneration: Current status," 2010, Surg. Neurol Int 1, 93.

Sofie, et al., "Freeze Casting of Aqueous Alumina Slurries with Glycerol." 2001,Journal of the American Ceramic Society 84(7):1459-1464.

Stokols,et al., "The fabrication and characterization of linearly oriented nerve guidance scaffolds for spinal cord injury." 2004, Biomaterials 25(27): 5839-5846.

Straley et al., "Biomaterial design strategies for the treatment of spinal cord injuries." 2010, J Neurotrauma 27: 1-19.

Suzuki, et al., "Regeneration of transected spinal cord in young adult rats using freeze-dried alginate gel." 1999, NeuroReports 10:2891-2894.

Teng, Y.D., et al., "Functional recovery following traumatic spinal cord injury mediated by a unique polymer scaffold seeded with neural stem cells." 2002, Proc Nat Acad Sci USA 99(5):3024-3029.

Thuret, et al., "Therapeutic interventions after spinal cord injury." 2006, Nat Rev Neurosci 7(8): 628-643.

Tong, et al, "CPS 768 Formation of anisotropic ice-agar composites by directional freezing." 1984, Colloid & Polymer Science 262(7):589-595.

Tong, et al., "Mechanism of lamellar spacing adjustment in directionally frozen agar gels." 1985, Colloid & Polymer Science 263(2):147-155.

Tunturi, A.R., "Elasticity of the spinal cord dura in the dog." 1977, Journal of Neurosurgery 47(3):391-396.

Wegst et al., "Biomaterials by freeze casting." 2010, Philos Transact A Math Phys Eng Sci 368: 2099-121.

Willerth, S.et al., "Approaches to neural tissue engineering using scaffolds for drug delivery." 2007, Advanced Drug Delivery Reviews 59(4-5):325-338.

Woerly, S., et al., "Spinal cord repair with PHPMA hydrogel containing RGD peptides.(NeuroGel)." 2001, Biomaterials 22(10):1095-1111.

Woerly, S., et al., "Spinal cord reconstruction using NeuroGel implants and functional recovery after chronic injury." 2001, Journal of Neuroscience Research 66(6):1187-1197.

Xu, X.M., et al.,"Regrowth of axons into the distal spinal cord through a Schwann-cell-seeded mini-channel implanted into hemisected adult rat spinal cord." 1999, European Journal of Neuroscience 11(5):1723-1740.

Yook, et al., "Porous titanium (Ti) scaffolds by freezing TiH2/camphene slurries." 2008, Materials Letters 62(30):4506-4508.

Zhang, et al., "Fabrication of semipermeable hollow fiber membranes with highly aligned texture for nerve guidance." 2005, Journal of Biomedical Materials Research Part a 75A(4):941-949.

* cited by examiner

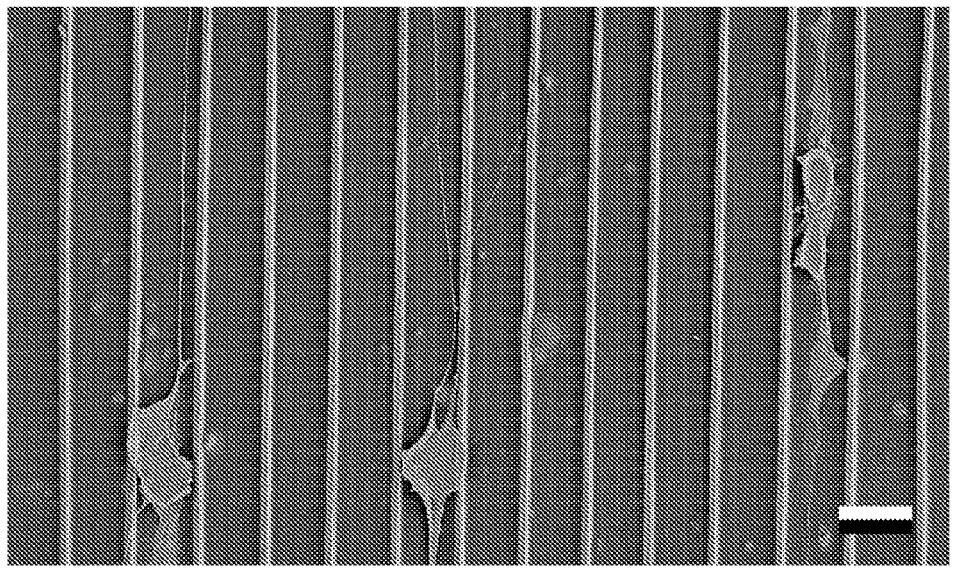
Figure 23
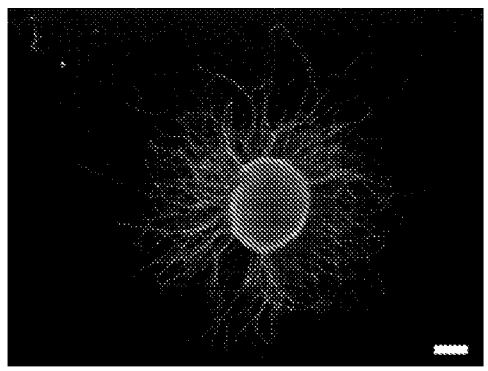 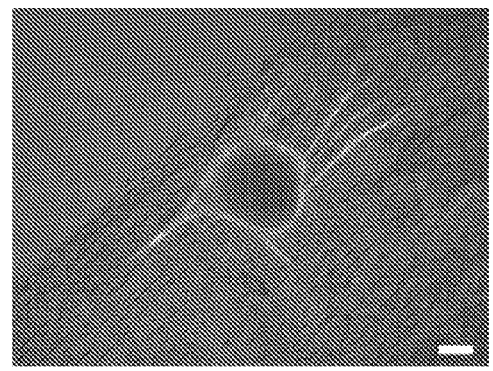
Figure 24A      Figure 24B

Figure 33 Freeze-caster schematic.

Figure 34 Schematic of alginate and how it reacts to the addition of calcium (Prior Art)

US 8,877,498 B2

POROUS POLYMER SCAFFOLDS FOR NEURAL TISSUE ENGINEERING AND METHODS OF PRODUCING THE SAME

CROSS-REFERENCE TO RELATED APPLICATIONS

The present invention and application claims priority to U.S. Provisional Application Nos. 61/418,776, filed on Dec. 1, 2010, and 61/474,636, filed on Apr. 12, 2011, the contents of which are each incorporated by reference herein as if each is set forth herein it its entirety.

BACKGROUND OF THE INVENTION

Spinal cord injury (SCI) has attracted significant interest in the field of biomedical implants; its challenges range from matching the mechanical values of the host tissue to creating a scaffold capable of physically guiding the growing neurites. To date, no scaffold has yielded complete functional recovery, though recent attempts have managed to solve some, but not yet all, of the requirements for an effective scaffold. A historical summary of these efforts and related developments is presented below.

Cellular solids, being composites of a solid material and a gas phase, can be roughly divided into two broad categories: stretch-dominated structures and bending-dominated structures. Stretch-dominated structures are characteristically represented by honeycombs or lattice-like structures, while bending-dominated structures are characteristically represented by equi-axed foams consisting of open cell edges and cell faces [Ashby, 2005, Philosophical Magazine 85(26): 3235-3257]. Cellular solids are further characterized by their relative density: density of the cellular solid divided by the density of the fully-dense constituent materials. Failure of cellular foams can be broadly divided into three categories: plastic deformation, elastic buckling, and brittle fracture. In plastic deformation, the edges of the cell bend plastically, whereas elastomeric foams fail by elastic buckling. Brittle foams fracture at the cell edges. When plotting the material properties of cellular solids, the relative density often provides an intuitive and easy to manage means of comparing broad classes of materials. Typically, axially-loaded honeycombs (stretch-dominated lattices) perform better than equi-axed foams at the same relative density.

The processing of solutions and suspensions by the physical process of solidifying the solvent and removing it has been referred to as many things, including but not limited to: freeze casting, directional and uni-directional solidification, ice templating, and dendritic solidification. During solidification, the solubility of the solute is lower in the solid region than the liquid region; this inequality leads to solute being rejected from the propagating interface and accumulating. This boundary layer of solute changes the local concentrations, which in turn affects the liquidus temperature and creates a liquidus gradient across the boundary. When this liquidus gradient is higher than the temperature gradient formed by the freezing dendrite, the liquid is undercooled, also referred to as supercooled, as it is forced below its freezing temperature while remaining a liquid. This unstable region of supercooled liquid creates the driving force for ice-crystal formation, which propagate throughout the structure. If the overall thermal gradient is uniformly distributed, the ice-crystals will propagate in random directions, resulting in grain-like boundaries of ice. If, in the case of freeze casting, the temperature gradient is directional, then the region of constitutional undercooling will continue to push the ice-crystals in the same direction, creating a freezing front of dendrites. The growth of these dendrites is thus constrained by the undercooling conditions, which is in turn controlled by the temperature gradient; thus the freezing-front velocity of the dendrites is controlled by the rate of thermal diffusion. The rate of thermal diffusion is, in many freeze-casting systems in the art, controlled by controlling the temperature of a cold finger or cold source that the sample is placed in contact with and the cold-source's temperature is lowered at a steady rate, creating a uniform temperature gradient throughout the sample.

It has been reported that the freezing front of linearly aligned dendrites is only established once steady-state conditions have been reached, and two initial regions are observed prior to this steady state [Deville, et al., 2006, Biomaterials, 27(32):5480-5489].

Directly in contact with the cold source, the first zone (identified by Deville et al. in 2006) has little to no porosity, while the second has a uniform cellular morphology. The end of the second zone and the beginning of the third zone is characterized by the transition of the ice-crystals from a disperse cellular morphology to a linearly oriented morphology consisting of dendrites growing parallel to the thermal gradient [Deville, et al., 2006, Biomaterials, 27(32):5480-5489]. This was experimentally verified in-situ in 2009 by Deville et al., who used x-ray radiography to visualize the in-situ solidification of the third zone [Deville, et al., 2009, Journal of the American Ceramic Society 92(11): 2489-2496; Deville, et al., 2009, Journal of the American Ceramic Society 92(11): 2497-2503].

In 1954 Maxwell et al. reported on the freeze casting of thick slips of titanium carbide to make turbosupercharger blades. The researcher's aim was not to use this processing method to create highly porous structures, as most current biomedical applications require, but rather to generate high solid content slips that still retained oriented architectures, The opposite effect was accomplished 30 years later, when Ezekwo et al. and Tong et al. used directional freezing to structure highly porous aqueous agar gels [Tong, et al, 1984, Colloid & Polymer Science 262(7):589-595, Ezekwo et al., 1980, Water Research 14:1079-1088]. These gels exhibited the characteristic linearly oriented porosity of freeze-cast structures, as evidenced by both cross-sections and longitudinal slices. In 1985, Tong and Gryte analyzed the mass diffusion of the agar gels that they created and attempted to correlated the velocity of the freezing front to the resultant lamellae spacing.

More recently, freeze casting has received increased attention in three broad categories—ceramics, polymers, and metals, mostly for biomedical applications due to the inherently controlled architecture with porosity often in the range required for biological integration, Interest in ceramics revamped in the early 2000's, starting with filtration and catalyst applications [Fukasawa, et al., 2001, Journal of Materials Science 36(10):2523-2527; Fukasawa, et al., 2001, Journal of the American Ceramic Society 84(1):230-232; Fukasawa, et al., 2002, Journal of the American Ceramic Society 85(9): 2151-2155; Sofie, et al., 2001, Journal of the American Ceramic Society 84(7):1459-1464; Deville, et al., 2006, Science 311(5760):515-518]. With regard to biomedical applications, collagen has been particularly focused on, with recently some very promising attempts by Bozkurt et al. [Schoof, et al., 2000, Journal of Crystal Growth 209(1): 122-129; Schoof, et al., 2001, Journal of Biomedical Materials Research 58(4): 352-357; Bozkurt, et al., 2007, Tissue Engineering 13(12):2971-2979; Bozkurt, et al., 2009, Biomaterials 30(2):169-179], Metals represent the newest class of materials that have been freeze cast, and titanium scaffolds have opened a new range of material properties achievable for such high porosities [Chino, et al., 2008, Acta Materialia, 56(1):105-113; Yook, et al., 2008, Materials Letters 62(30): 4506-4508].

In 1985, H. M. Tong and C. C. Gryte presented a theory for predicting the size of lamellar ice crystal sheets resulting from steady-state unidirectional freeze casting of aqueous agar. They compared their model against varying concentrations of agar solidification and subsequent lyophilization, and found that the model could not predict the changes when the solution was increased from 3% to 10% by weight.

Tong and Gryte considered a hypothetical interface approximated by a trigonometric function as opposed to the actual finger-like dendritic extension micrographed by Bozkurt et al. in 2009 [Bozkurt, et al., 2009, Biomaterials 30(2): 169-179; Tong, et al., 1985, Colloid & Polymer Science 263 (2):147-155]. They defined $\lambda$ as the lamellar spacing, and set the trigonometric function to $z = p_0 \cos(wx)$ where $p_0$ is the amplitude of the function (and of the ice tips) and $$\lambda = \frac{2\pi}{\omega} = \frac{L_0}{n},$$

where n is the number of crystal tips along $L_0$ minus 1.

With respect to the mass transfer analysis of the situation, Tong and Gryte defined the continuity equation as equation (1), subject to boundary conditions (2) through (5), where is the agar concentration, V is the freezing-front velocity of the ice-crystals, and D is the diffusion coefficient. In essence, these boundary conditions are as follow: The concentration of the solution at $z=\infty$ is that of the bulk agar concentration, and the change in concentration with respect to x (perpendicular to the ice-crystal growth front) is zero at the center of each ice-crystal. They defined the change in concentration along the propagating ice-crystal freezing front (the z-direction) as equation (4) at point T (the tip of the ice-crystal) and zero (with $C=C_g$) at point V (the nadir of the trigonometric function, representing the fully vitrified agar solution). Cg, the agar concentration of the vitrified solution, was taken to be 50%, as previously determined [Tong, et al., 1985, Colloid & Polymer Science 263(2):147-155].

$$\frac{\partial^2 C}{\partial z^2} + \frac{\partial^2 C}{\partial x^2} + \left(\frac{V}{D}\right)\left(\frac{\partial C}{\partial z}\right) = 0 \quad (1)$$

$$C = C_g @ z = \infty \quad (2)$$

$$\frac{\partial C}{\partial x} = 0 @ x = 0 \text{ and } \frac{\pi}{\omega} \quad (3)$$

$$\frac{\partial C}{\partial z} = -\left(\frac{V}{D}\right)(1 - k_0)C = -\left(\frac{V}{D}\right)C_T @ \text{point } T \quad (4)$$

$$\frac{\partial C}{\partial z} = 0 \text{ and } C = C_g @ \text{point } V \quad (5)$$

In order to analyze the solute concentration ahead of the hypothetical interface, Tong and Gryte divided the concentration into two terms—the first a composition averaged across the interface ($c_0$) that is only a function of the z-direction (freezing direction) and the second a radial component that is a function of both x and z directions ($c_1$). See equation (6), where $$\omega = \frac{\lambda}{2\pi}.$$

Using a first-order approximation (n=1), Tong and Gryte were able to analytically solve for the constants a and h as functions of the concentration, freezing front velocity, diffusion constant, and physical parameters. They were thus able to derive a relationship between $p_0$ and $\lambda$—equation (7)—where $$\omega = \frac{\lambda}{2\pi}.$$

$$C\lfloor x,z \rfloor = C_0 \lfloor z \rfloor + C_1 \lfloor x, z \rfloor \quad (6)$$

Where $C_0 \lfloor z \rfloor = C_b + \lambda e^{\left\lfloor \frac{-vz}{D} \right\rfloor}$, $C_1 \lfloor x, z \rfloor = \sum_{n=1}^{\infty} a_n e^{\lfloor -\omega_n z \rfloor \cos \lfloor n\omega x \rfloor}$, and $$\omega_n = \frac{v}{2D} + \sqrt{\left(\frac{V}{2D}\right)^2 + n^2 \omega^2}$$

$$p_0 = \frac{\ln\left(\frac{c_g}{c_b} - 1\right)}{2\omega_1} \quad (7)$$

It is interesting to note, then, that the solution to the mass-diffusion differential equations can be defined by two dimensionless parameters:

$$\left(\frac{\lambda}{p_D}\right) \text{ and } \left(\frac{\lambda V}{D}\right).$$

in order to develop a relationship between the lamellar spacing and the diffusion constant and the freezing front velocity, two different approaches were taken, arriving at two different relationships between $p_0$ and $\lambda$.

The first, more complicated and more accurate method involved analysis of the lowest free energy criterion, wherein it was noted that no significant amount of undercooling was needed for the propagation of the ice crystals, and that therefore equilibrium conditions are established at the freezing front. Analysis of the free energy of the system led to equation (8), which establishes a relationship between $p_0$ and $\lambda$.

$$\Delta G_{total} = \left(\frac{\sigma L_0}{\pi}\right) I\lfloor \omega \rfloor + \text{constant} \quad (8)$$

Where $I\lfloor \omega \rfloor = \int_0^\pi \sqrt{1 + p_D^2 \omega^2 \sin^2 \lfloor y \rfloor} \, dy$ The second, more elegant, albeit less accurate method used Einstein's diffusion theory to relate the time for a molecule to move a distance $$\frac{\lambda}{2},$$

or $$\frac{\pi}{\omega},$$

to the effective diffusion coefficient D. Physically, then, this is the time that it takes the molecules to move from the tip of the ice-crystal to the center of the vitrified region. This distance is by definition $2p_0$, and with V being the velocity of ice the time is thus $$\frac{2p_0}{V}.$$

These two times must be equal to avoid agar build-up between the propagating ice-crystals, and thus solving for $p_0$ as a function of lamellar spacing $\lambda$ yields equation (9).

From empirical testing of $p_0$ and $\lambda$, Tong and Gryte saw that the ratio of $$\frac{\lambda}{p_0}$$

remains constant throughout the freezing process across varying velocities, and that therefore equation (9) reduces to simply $$\frac{V\lambda}{D} = \text{Constant},$$

which for a constant diffusion coefficient reduces to $V\lambda$=Constant.

$$p_0 = \frac{V\pi^2}{4D\omega^2} = \frac{V\lambda^2}{16D} \quad (9)$$

When analyzing these assumptions and comparing them against the literature and other models, several key differences are noticed which could account for the inability to accurately predict the lamellar spacing.

Other equations have been proposed that suggest the linear relationship $$\lambda \propto \frac{1}{V^n},$$

where n is between 1 and 4 [Butler, 2001, Crystal Growth & Design 1(3): 213-223; Deville, et al., 2007, Acta Materialia 55(6):1965-1974].

The majority of freeze-cast polymers to date have been collagen or collagen-combinations, though chitosan has of recent been gaining more attention. Some of the more comprehensive reports have been by Bozkurt et al., who froze collagen for biomedical applications.

In an intact spinal cord, afferent neurons project through interneurons to motor neurons within the gray matter, which send axons out through the dorsal root ganglions to the peripheral nervous system (PNS). Conversely, primary sensory neurons project axons through the PNS to the gray matter in the central nervous system (CNS), where they are transferred to the white matter and directed to supraspinal areas. Lipid-derived myelin coating of the axons allows for saltatory nerve conduction, in which action potentials leap from sequential nodes of Ranvier. This coating is performed by oligodendrocytes in the CNS and Schwann cells in the PNS.

The heterogeneous nature of spinal cord injury (SCI) leads to varied endogenous responses, and can be caused by contusion, compression, or penetration of the spinal cord [Thuret, et al., 2006, Nat Rev Neurosci 7(8): 628-643]. Contusions frequently generate cysts, consisting of astrocytes, progenitor cells, and microglia. Penetrating injuries generally allow for PNS cells to infiltrate and form scar tissue, which is usually formed from fibroblasts, Schwann cells, and various reactive glia. Either of these processes usually interrupts both ascending and descending neuronal tracts, and are detrimental to oligodendrocytes, neuroglia, and precursor cells [Horkey, L. L., et al., 2006, The Journal of Comparative Neurology 498 (4):525-538], while any disconnected axons segments are phagocytosed by macrophages [Thuret, et al., 2006, Nat Rev Neurosci 7(8): 628-643]. Following the initial injury, active secondary processes occur, which have been attributed to apoptosis, Ca2+ influx, plasma membrane disruption, and lipid peroxidation. Apoptotic cells positively expressing oligodendrocyte markers were seen from 6 hours up to 3 weeks [Crowe, M. J., et al., 1997, Nat Med 3(1):73-76], and chronic resulting demylinated axons have been found at the site of injury up to 10 years post-trauma [Guest, et al., 2005, Experimental Neurology 192(2):384-393].

Some of the first quantitative measurements of the spinal cord modulus were performed in the late 1970's at the University of Oregon Health Sciences, Center, and in the early 1980's at the University of Pittsburgh. Archie R. Tunturi, M. D., working in Oregon, measured specifically the spinal cord dura matter in dogs, while the researchers at the University of Pittsburgh sought to test the mechanical properties of the neuronal column itself [Tunturi, A. R., 1977, Journal of Neurosurgery 47(3):391-396]. Three papers resulted from these initial experiments; two on cats, and one on puppies. In all cases, the subjects were anesthetized and mounted within an Instron tensile testing device. Ring clamps were mounted on the subjects' exposed spinal cords, which were then stripped of the dura matter. It is, however, critical to note that by only removing the dura matter, the researchers were testing a combination of pia, gray, and white matter. This is a key distinction to make note of, as the neuronal cells interact with the gray and white matter, but not the pia mater; thus any scaffolds designed to match the mechanical properties need to match those of the gray and white, not the combination of those with the pia mater. By performing these experiments in-situ on anesthetized subjects the researchers avoided changing physiological conditions incurred by death. To avoid dehydration, upon exposure of the spinal cord the researchers housed the test section in a polymer container, and filled the reservoir with Normosol, an isotonic solution of electrolytes as a substitute for the native cerebrospinal fluid [Hung, T.-K., et al., 1981, Journal of Biomechanics 14(4): 269-276].

A more detailed testing procedure was carried out by Bilston and Thibault in 1995, wherein they tested cervical sections of human cadavers. A quasilinear viscoelastic model was arrived at; however, specific moduli for different strain rates were reported, and one can see that the moduli were approximately 1 MPa [Bilston, L. et al., 1995, Annals of Biomedical Engineering 24(0):67-74]. Again, however, Bilston and Thibault reported removing the dura matter but specifically leaving the pia, gray, and white matter. Also, the samples were harvested up to 12 hours post-mortem, which has been suggested to dehydrate and stiffen the native tissues [Bilston, L. et al., 1995, Annals of Biomedical Engineering 24(0):67-74; Ozawa, H., et al., 2004, J Neurosurg Spine 1(1): 122-7]. This explains the significantly higher modulus reported by Bilston and Thibault, as compared to Ozawa et al. in 2004, who measured specifically the Pia mater by itself, the gray and white matter by themselves, and the gray and white matter with the Pia mater left attached. Ozawa et al. found that the Pia mater by itself had a Young's modulus of 2.3 MPa, and when left intact and wrapped around the gray and white matter, it effectively tripled the modulus from 5 to 16 kPa. Unfortunately, the researchers tested the Pia mater itself in tension, and then tested gray and white matter, and the gray/white/Pia combination, in compression, which may explain why the Pia mater, with a Young's modulus of 2.3 MPa in tension, only tripled the compressive modulus of the gray/white/Pia combination to 16 kPa. The researchers also performed a series of cross-sectional compression analyses with and without the Pia mater and concluded that the Pia mater, along with the dura matter, is largely responsible for producing a strain energy on the gray and white matter, which is responsible for maintaining the shape and circumference upon compression.

In 2001, Ozawa et al, performed some of the first mechanical testing on specifically the gray and white matter in-situ. To avoid any post-mortem changes in physiology, they performed their tests within one hour of sacrificing the subjects (cats). They excised the spinal cord segments, removing both dura and pia mater, and sliced the remaining gray and white matter so as to expose either sagittal, axial, or frontal planes. Mechanical testing was performed via pipette aspiration, whereby a glass pipette was placed perpendicular to the substrate, and negative pressure applied via a reservoired vacuum pump. Deformation was measured by a video microscope, and a video dimension analyzer was used to determine the aspirated length of the substrate. Their findings were, expectedly, in close agreement with mechanical testing performed on brain parenchyma [Ozawa, H., et al., 2001, Journal of Neurosurgery: Spine 95:221-224].

The importance of these studies becomes rapidly event when trying to match the mechanical values of a neuronal scaffold to those of the native tissues. Many of the mechanical values reported in the literature only report on an ill-defined "spinal cord's" Young's modulus, and it is only through a thorough investigation of the literature, along with knowledge of the spinal cord anatomy, that one realizes that many of the reported values are not those of the tissues that the neurons actually interact with. One of the first research groups to accurately cite the correct values was headed by Bakshi et al. [Bakshi, A., et al., 2004, Journal of Neurosurgery: Spine 1(3)322-329]; they were able to achieve a hydrogel scaffold of appropriate stiffness.

The importance of matching substrate stiffness has been receiving growing recognition in recent reviews [Madigan, N., et al., 2009, Respiratory Physiology & Neurobiology 169(2):183-199], and for neuronal growth was specifically tested and proven in 2009 by Leipzig and Shoichet [Leipzig, N. et al., 2009, Biomaterials 30(36):6867-6878]. To create a substrate of specific mechanical stiffness, a photopolymerizable methacrylamide chitosan (MAC) was developed, the modulus of which could be directly tuned from the amount of photo-induced crosslinking. Three scaffolds of varying moduli were created, resulted in E=0.8±0.18, 3.59±0.51, and 6.72±0.58 kPa, herein referred to simply as 1, 3.5, and 7 kPa. In order to achieve a more robust cell attachment, the researchers coated their chitosan scaffolds with laminin, a protein family found in the basil lamina. Neural stem/progenitor cells (NSPCs) were harvested from adult subventricular zones and cultured on the various substrates; examined were the differentiation of the NSPCs into the three main cell types of the neuronal cord: neurons, oligodendrocytes, and astrocytes. Cell differentiation and proliferation for neurons were shown to be highest when E=3.5 kPa, consistent with the measured gray and white matter mechanical values by Ozawa et al. in 2001. Oligodendrocyte maturation was shown to be highest on the softest substrates, although cell differentiation was highest on the 7 kPa. The researchers justified this difference in cell maturity and differentiation by explaining that in the presence of increased neuronal growth, the oligodendrocytes would exhibit more mature features, as they had more neurons to ensheath. Leipzig and Shoichet also created substrates with moduli greater than 10 kPa, upon which the NSPCs neither proliferated nor differentiated.

Significant numbers of polymeric scaffolds for spinal cord regeneration of particular mechanical values and/or particular geometries have been created over the years. One of the first papers to recognize the importance of matching mechanical strengths—and realize what the correct mechanical values are—was the previously mentioned paper by Bakshi et al. in 2004. The authors created poly(2-hydroxyethylmethacrylate) (pHEMA) hydrogels with 85% water content and interconnected pores 10 to 20 μm in diameter. When soaked in simulated physiological conditions, the scaffolds had compressive moduli of 3 to 4 kPa, which aligns well with the previously mentioned values. They performed a partial cervical hemisection, peeling back the dura mater and implanting the scaffold before closing the flap of dura and suturing. The authors soaked the pHEMA in brain-derived neurotrophic factor (BDNF) and saw that up to 2 weeks the BDNF-soaked scaffolds promoted significant axonal regeneration and growth into the scaffold. Unfortunately, after the two weeks the axonal growth regressed, most likely due to the BDNF diffusing away, since the authors did allow that unmodified pHEMA was not suitable for axonogenesis [Bakshi, A., et al., 2004, Journal of Neurosurgery: Spine 1(3):322-329].

Aside from BDNF, a host of other growth factors have been similarly used, such as ciliary neurotrophic factor (CNTF), which plays a role in motor neuron growth and survival, fibroblast growth factors (FGFs), which indirectly help by inducing angiogenesis and directly have been shown to promote axon outgrowth, and glial derived neurotrophic factor (GDNF), which is secreted by Schwann cells after injury and is structurally similar to transforming growth factor β (TGF-β), which may be useful for coating neural implants [Willerth, S. et al., 2007, Advanced Drug Delivery Reviews 59(4-5): 325-338]. Schwann cells in particular have been used in many of the more promising experiments, and have been incorporated into a variety of scaffold and scaffold-like containers. In 1999, Xu et al. seeded Schwann cells in Matrigel, an extracellular-like matrix of proteins secreted by mouse sarcoma cells. It was claimed that due to an inherent "syneresis" effect of Matrigel, a cable of aligned Schwann cells formed over 24 hours, though they provided no proof. The Matrigel seeded matrix was placed inside a spun 60:40 acrylonitrile:vinylchloride (PAN/PVC) copolymer which was capped at either ends with a glue of PAN/PVC. The presence of Schwann cells induced up to $10^5$ axons to enter the graft; a result that is not atypical with Schwann cell seeded grafts [Xu, X. M., et al., 1999, European Journal of Neuroscience 11(5):1723-1740; Oudega, M., et al., 2001, Biomaterials 22(10):1125-1136].

Hydrogels are, arguably, the most common scaffolds used for attempted spinal cord reparation. They are generally water-insoluble polymer networks that are highly porous and typically have water contents greater than 90 percent. pHEMA [Dalton, P. D., et al., 2002, Biomaterials 23(18): 3843-3851; Bakshi, A., et al., 2004, Journal of Neurosurgery: Spine 1(3):322-329] and poly N-2-(hydroxypropyl)methacrylamide (PHPMA) [Woerly, S., et al., 2001, Biomaterials 22(10):1095-1111; Woerly, S., et al., 2001, Journal of Neuroscience Research 66(6):1187-1197] are two such hydrogels used as scaffolds for SCI. The biggest drawback of hydrogels is their isotropic nature. While they may be highly porous, their physical structure does not lend itself to aligned growth.

Because of this drawback to hydrogels, many researchers have attempted to generate linearly oriented scaffolds so as to physically guide the growing axons. Teng et al. in 2002 used a poly(lactic-co-glycolic acid) (PLGA) blend to generate axially oriented pores by unidirectionally freezing a solution of PLGA and subliming the solvent. The freezing was produced by lowering the solution into an ethanol/dry ice bath, which created both longitudinal and radial porosity [Teng, Y. D., et al., 2002, Proc Nat Acad Sci USA 99(5):3024-3029]. Another attempt at induced growth by linearly aligned contact guidance was done in 2003 by Yoshii et al. who used bundled collagen filaments to provide linearly oriented cables along which the nerve cells could grow. After 8 weeks in vivo axon growth extended 20-24 millimeters into the graft. The collagen filaments averaged 20 µm in diameter, and both 2000 and 4000 bundled filament grafts were used. Unfortunately, no mention of how tightly compressed or cross-section images of the filaments were reported; thus knowledge of the substrate that the axons were growing on is lacking. A similar attempt was made by Stokols et al. in 2004 when they placed dissolved agarose on top of a pool of liquid nitrogen; the linear ice crystals were then sublimed away.

The average pore diameter was 119 µm, and the walls of the pores were smooth. While the morphology of the scaffolds is approaching that of a well-designed scaffold, the authors failed to recognize the importance of matching the mechanical properties of the scaffold. Their only mention was that the hydrated scaffold was "soft and flexible," possessing mechanical properties "hypothetically advantageous for use in the spinal cord." A nerve growth factor was incorporated into the scaffold, and PC12 cells were cultured successfully, demonstrating the feasibility of the agarose scaffolds [Stokols, et al., 2004, Biomaterials 25(27): 5839-5846].

In 2005, Mahoney et al. attempted a systematic approach to linearly guiding neurite growth by creating channels on a photosensitive polyimide (PSPI). The walls of the channels were 11 µm high and 10 µm wide, while the width of the channel ranged from 20 µm to 60 µm, in steps of 10 µM. PC12 cells were terminally differentiated with NGF and seeded along the patterned chips for 3 days. The length, number of neurites exiting each soma, and angle of neurite to the channel wall were all measured. The neurites often grew towards the channel walls, and then continued in roughly a straight line. It was seen that in the control PC12 cells, which were seeded on flat unpatterned chips, the number of exiting neurons were twice that of those exiting the 20 µm wide channels; however the 20 µm wide channels had the longest neurites. Unfortunately, the authors did not create channels less than 20 µm wide, so there is it not known whether 15 or 10 µm wide channels would generate longer neurites.

Another attempt to linearly guide neurites by growing them along channels was performed by Zhang et al. in 2005. Using wet phase inversion they created hollow fiber membranes out of PLGA with textured inner diameters that had grooves running parallel to the axis of the hollow membrane. Dorsal root ganglions (DRGs) were seeded at one end of the membrane and cultured for 7 days. [Zhang, et al., 2005, Journal of Biomedical Materials Research Part A 75A(4):941-949].

Johansson et al. analyzed sub-micron channel guidance of neurites, using nanoimprint lithography to generate PMMA substrates with 300 nm deep channels of varying width (100 to 400 nm) and varying distance between channels (100-1600 nm). These channels were roughly an order of magnitude smaller than the two previously mentioned studies, and the channels were approximately on the same scale as the extending neurites themselves. The authors reported on a "wandering behavior" of the axons at that scale, and stated that the axons had a tendency to branch back and forth across several ridges, despite maintaining an overall linear growth. SEM images show that the axons grew on the top of the ridges, as opposed to inside the larger channels of Mahoney et al.'s substrates. The SEM images also showed a significantly scattered growth pattern of neurites, to the point where the authors used a Fourier transform to quantify the amount of guidance. Results from their experiments show that nano-scale channels are capable of aligning axons, although the SEMs suggest that the channels were too small to cause any more than general alignment; significant bridging and wandering of the axons can be seen, and their results suggest no clear trend in either channel width or spacing for optimal alignment.

Two of the most impressive papers on spinal cord repair scaffolds were produced by Bozkurt et al. in 2007 and 2009 [Bozkurt, et al., 2007, Tissue Engineering 13(12):2971-2979; Bozkurt, et al., 2009, Biomaterials 30(2):169-179]. Based in Aachen, Germany, the group used freeze casting to general linearly oriented porcine collagen scaffolds with pore diameters of 20 to 50 µm. Biopsy punches were used to generate cylinders of scaffold. DRGs were harvested from Lewis rats and sliced in half; the sectioned surface was then placed on the cross-section surface of the scaffolds and cultured for 21 days. In-vitro analysis was performed using fluorescent light microscopy and confocal laser microscopy.

In 2009 the same group of researches varied the amount of crosslinking within the same freeze-cast collagen scaffolds and seeded the scaffolds with Schwann cells. Crosslinking was achieved with 1-ethyl-3(3-dimethylaminopropyl)carbodiimide (EDC). Gamma irradiation sterilized said scaffolds, and the degree of crosslinking was determined by spectrophotometrically measuring the free amine group content. Immunocytochemistry of the Schwann cells shows linear alignment of the Schwann cells.

Thus, there is a long felt need in the art for a freeze cast polymer scaffold for targeted neuronal growth and repair, as well as a process for controlling freeze casting such that the morphology and mechanical features of the scaffold can be customized and selected for. The present invention satisfies this need.

SUMMARY OF THE INVENTION

A scaffold for supporting cell growth is described. The scaffold includes regions of aligned porosity, wherein the pore walls of the scaffold include ridges that protrude from the pore wall. In one embodiment, the scaffold is composed of a polymer. In another embodiment, the scaffold is composed of a combination of two or more polymers. In another embodiment, substantially parallel grooves are formed between adjacent ridges. In another embodiment, the formation of the height and width of each ridge is controlled in a micrometer to nanometer length scale. In another embodiment, the width of each groove is controlled in a micrometer to nanometer length scale. In another embodiment, the modulus of the scaffold and scaffold forming material is controlled in the kPa to GPa range. In another embodiment, the strength of the scaffold and scaffold forming material is controlled in the kPa to GPa range. In another embodiment, the toughness and fracture toughness of the scaffold and scaffold forming material is controlled in the $J/m^3$ to $MJ/m^3$, and in the $kPa \cdot m^{1/2}$ to $MPa \cdot m^{1/2}$ range, respectively.

Also described is a method of producing a scaffold having regions of aligned pores that include ridges protruding from the pore walls. The method includes the step of freeze casting a compound at a cooling rate of between about 0.1-100° C./m.

Also described is a method of guiding the direction of neurite outgrowth. The method includes the steps of engaging at least one neurite with a scaffold having regions of aligned porosity that include ridges and grooves protruding from the pore walls, such that outgrowth of the neurite is channeled substantially along the linear axis of the ridges or grooves. In one embodiment of the method, outgrowth of the neurite is stunted from growing in a direction that is tangentially skewed from the linear axis of the ridges or grooves.

A method of connecting two or more separated neurites is also described. The method includes the steps of engaging at least two separated neurites with a scaffold having regions of aligned lamellae that include grooves bordered by ridges protruding substantially perpendicular and uniformly from the lamellae wall, such that the outgrowth of the neurites is channeled substantially along the linear axis of the grooves towards each other.

Also described is a method of controlling directional outgrowth of a neurite that includes the steps of engaging at least one neurite with a scaffold having regions of aligned lamellae that include grooves bordered by ridges protruding substantially perpendicular and uniformly from the lamellae wall, such that outgrowth of the neurite is stunted from growing in a direction that is tangentially skewed from the linear axis of the grooves.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 7A is a chart of the modulus vs. freezing rate in the dry state, while

FIG. 10A is a chart of the modulus vs. freezing rate in the wet state, while

FIG. 20B shows two soma nestled within a groove extending neurites. Scale bar for both is 20 μm.

FIG. 23 is a false-colored SEM image of neurons cultured on laminin-coated chitosan scaffolds. Scale bar is 20 μm.

FIG. 24A is an image of a control DRG cultured for 24 hours on a laminin-coated glass coverslide, and FIG. 24B is an image of a DRG cultured on a single lamellae. Partial neurite alignment was seen after 24 hours. Scale bar for both is 200

FIG. 29A is an image created from a full-circled mold, while FIG. 29B is an image created from a half-circle mold. Scale bar for both is 200 μm.

FIG. 54 depicts scanning electron micrographs of chitosan-alginate scaffold directionally frozen at VC/min, prior to crosslinking. FIG. 54A depicts a transverse section of scaffold. FIG. 54B depicts a longitudinal section of scaffold. Scale bar=100 μm.

FIG. 55 depicts scanning electron micrographs of chitosan-alginate scaffold directionally frozen at VC/min, after crosslinking. FIG. 55A depicts a transverse section of scaffold. FIG. 55B depicts a longitudinal section of scaffold. Scale bar=100 μm.

FIG. 56 depicts light micrographs of chitosan-alginate scaffold directionally frozen at 1° C./min, prior to crosslinking; effects of scaffold formation at different pH. FIG. 56A depicts a transverse section of chitosan-alginate scaffold formed at pH 7.4; FIG. 56B depicts a transverse section of chitosan-alginate scaffold formed at pH 4.35. Scale bar=100 μm.

FIG. 57 depicts the results of experiments quantifying the average DRG axon length on scaffolds with various surface coatings.

FIG. 58 depicts confocal microscope images of immunostained DRGs on scaffolds with varying surface treatments: FIG. 58A) uncoated scaffold; FIG. 58B) PLO-coated scaffold; FIG. 58C) PLL-coated scaffold; FIG. 58D) Laminin-coated scaffold; FIG. 58E) PLO and laminin-coated scaffold; FIG. 58F) PLL and laminin-coated scaffold. Scale bar=100 μm.

DETAILED DESCRIPTION

Figure 1:
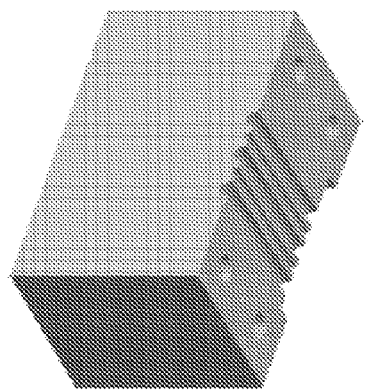
FIG. 1 is a CAD image of one half of the small mold. The mating edge of the other half had similar half-circle grooves, such that when compressed via the 4 outer bolt holes they formed 1 2 mm half-diameter groove, 1 1 mm half-diameter groove, 1 1 mm outer diameter circular groove, and 2 2 mm outer diameter circular grooves.

The present invention relates to a scaffold that can physically guide cells, e.g. neurons, while best matching the material properties of the native tissue. The present invention also relates to methods of generating such scaffolds, and to the use of such scaffolds in spinal cord injury repair. The methods of the present invention include a uniquely controlled freeze casting process to generate highly porous scaffolds with highly aligned porosity. The scaffold pores of the present invention are not only linearly oriented, but also contain secondary guidance structures in the form of ridges running parallel to the long pore axis to create a series of highly aligned channels. This hierarchy of structural guidance is shown in-vitro to align and guide cells, such as neurites, down the channels created by the ridges, and keep these cells from branching perpendicular to the grooves. The structure-property linkages of the constructs were examined for both dry and wet scaffolds, and mechanical values in the wet conditions are shown to be within a few kPa of the native tissue. Scaffolds were also freeze cast in different shapes and sizes, for example, with a circular and semicircular cross-section of 1 to 2 mm diameter molds to match rat spinal cords.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Exemplary Polymer Materials

Demonstrated herein is the feasibility of freeze casting biomaterials in the construction of neuronal scaffolds. In various embodiments, the scaffolds of the present invention can be constructed from a variety of polymer compositions, including, but not limited to, chitosan, chitin, cellulose, alginate, agar, gelatin, soy protein, hyaluronic acid collagen, elastin, and silk alone or in combination with any other polymer composition, in any concentration and in any ratio. In one embodiment, the scaffolds of the present invention comprise chitosan, either separately or in combination with one or more other materials. Chitosan is a polysaccharide and is a partially deacetylated derivative of chitin. Chitosan is cationic in nature, and allows for modifications with other molecules, such as glycosaminoglycans. Chitosan provides many options for ionic and covalent modifications and cross linking (e.g. with genipin), allowing mechanical properties and swelling to be adjusted and tailored for a particular application. Chitosan is also preferable for its relatively easy processing requirements. In another embodiment, chitosan may be used in combination with other materials, such as with gelatin or alginate.

Freeze-cast polymer structures were created across a range of processing conditions and sample sizes, and the structure-property correlations were elucidated, with particular emphasis on the local conditions required for ridge formation to occur in the solidifying structure and how these ridges serve to strengthen the elastically-dominated deformation in both dry and wet conditions.

In one aspect, polymer solutions having varying amounts of polymer dissolved in an acidic solution is used. The concentration of the acid can be adjusted depending on the amount of polymer dissolved. In one aspect, the acidic solution is 1% (v/v) acetic acid. In one embodiment, the amount of polymer in solution is between about 0.5-5% (w/v) and any whole or partial increments therebetween. For example, the amount of polymer in solution (w/v) can be about 0.5%, about 1%, about 1.5%, about 2%, about 2.5%, about 3%, about 3.5%, about 4%, about 4.5% or about 5%. In a preferred embodiment, the amount of polymer in solution is about 2.4% (w/v). In other various embodiments, the polymer is dissolved in at least one of water, acid, acetic acid, camphene, or camphene-naphthalene.

In another aspect, polymer solutions having varying amounts of chitosan dissolved in an acidic solution is used. The concentration of the acid can be adjusted depending on the amount of chitosan dissolved. In one aspect, the acidic solution is 1% (v/v) acetic acid. In one embodiment, the amount of chitosan in solution is between about 0.5-5% (w/v) and any whole or partial increments therebetween. For example, the amount of chitosan in solution (w/v) can be about 0.5%, about 1%, about 1.5%, about 2%, about 2.5%, about 3%, about 3.5%, about 4%, about 4.5% or about 5%. In a preferred embodiment, the amount of chitosan in solution is about 2.4% (w/v). In other various embodiments, the chitosan is dissolved in at least one of water, acid, acetic acid, camphene, or camphene-naphthalene.

In one aspect, polymer solutions can include varying amounts of gelatin in combination with varying amounts of chitosan, each dissolved in an acidic solution. The concentration of the acid can be adjusted depending on the amount of gelatin in combination with chitosan that is dissolved. In one aspect, the acidic solution is 1% (v/v) acetic acid. In one embodiment, the amount of gelatin in solution is between about 1-10% (w/v) and any whole or partial increments therebetween. For example, the amount of chitosan in solution (w/v) can be about 1%, about 2%, about 3%, about 4%, about 5%, about 6%, about 7%, about 8%, about 9% or about 10%. In a preferred embodiment, the amount of chitosan in solution is about 5.5% (w/v). In a more preferred embodiment, the polymer solution includes a combination of about a 2.4% (w/v) chitosan solution and about a 5.5% (w/v) gelatin solution. In other various embodiments, the gelatin in combination with varying amounts of chitosan is dissolved in at least one of water, acid, acetic acid, camphene, or camphene-naphthalene.

In an alternative embodiment, alginate is used as a scaffold material, either separately or in combination with one or more other materials. Alginate is easily processed, water soluble, and non-immunogenic. Alginate is a biodegradable anionic polysaccharide with free hydroxyl groups that offer easy gelling. Alginate is a derivative of brown seaweed that has been used for a various medical applications from impression casting in dentistry to medical bandages. The ability to be cast easily and proof of biocompatibility make alginate a desirable material for use in the present invention. Alginate absorbs and holds water well, making it ideal for injury repair where a moist environment is ideal for healing. Previous studies have shown promising results on alginate's process ability and properties for use in nerve repair [Suzuki, et al., 1999, NeuroReports 10:2891-2894; Nunamaker, et al., 2011, J Mech Behav Biomed 4:16-33; Pattani, et al., 2009, *Mol. Pharmaceutics*. 6 (2):345-352; Sobani, et al., 2010, Surg Neural Int 1, 93].

As contemplated herein, other polymer materials may be used, either separately or in any combination, and in any concentration, in the creation of the scaffolds of the present invention. Such additional or alternative materials may include, without limitation, collagen, elastin, agar, hydroxyapatite, PVA, agarose, PHBHHx (poly(3-hydroxybutyrate-co-3-hydroxy-hexanoate)), BGAL (1,2,3,4,6-pentaacetyl â-D-galactose), PCL, Alginate/CPC, and Soy Protein Isolate, for example. In one alternative embodiment, the polymer may be a polyelectrolyte complex mixture (PEC) formed from a 1:1 solution of chitosan and alginate. In yet another embodiment, the scaffold may formed from an alginate/calcium carbonate/glucono-delta-lactone mixture, such as 0.5-5% alginate, 0.5-15 g/L calcium carbonate, and 1-50 g/L gluconon-delta-lactone in a ratio of 2:1:1 (alginate:$CaCO_3$:GDL).

Depending on the materials and material ratios in mixture, the scaffolds may optionally be crosslinked. For example, after freezing and drying, a PEC mixture formed from a 1:1 solution of chitosan and alginate may be crosslinked in calcium chloride. In another example, an alginate based scaffold can be at least partially pre-gelled (by addition of $CaCO_3$: GDL), or crosslinked, to maintain the scaffold for freeze casting, drying and subsequent crosslinking with $CaCl_2$.

Additionally, the scaffolds as described herein can be coated fully or in-part with a variety of compounds, to alter the surface charge of the scaffold material, and in certain embodiments, to promote cell growth. For example, the scaffold can be at least partially coated with a polypeptide, such as polylysine or polyornitine, or glycoproteins. In another example laminin, either separately or in combination with a polypeptide, can be used to at least partially coat the scaffold. It should be appreciated that any polypeptide, glycoprotein or combination thereof, may be used to coat the scaffolds of the present invention.

Controlling the Cooling Rate During Freeze Casting

The aforementioned polymer solutions are freeze cast in various sized mold systems as would be understood by those skilled in the art, and further described in the examples presented herein. When pipetting the polymer solutions into small molds, air bubble formation is avoided by placing a micropipette on the open end of one of the mold grooves and repeatedly flushing the entire canal system until the residual air was flushed out.

In one aspect of the present invention, the rate of cooling is highly controlled, as the size and alignment of pores, as well as the formation of ridges, is effected by the cooling rate. In one embodiment, controlling thermal transfer from the cold finger to the mold can be accomplished with a tightly fitting secondary mold (copper) placed on the bottom of the primary mold so as to provide a controlled thermal transfer from the cold finger upon which the primary mold is placed. In some embodiments, the secondary mold at least partially covers the primary mold, and can leave the top of the primary mold open to ambient air conditions. In one embodiment, the rate of cooling is controlled by controlling the temperature at one end of the mold. In another embodiment, the rate of cooling is controlled by controlling the temperature at more the one end of the mold. In a further embodiment, the rate of cooling is controlled by transitioning the mold through a temperature gradient.

In another aspect of the present invention, the cold finger can be cooled down at various rates. In one embodiment, the cooling rate can range between about 0.1-100 degrees Celsius per minute CC/m) and any whole or partial increments therebetween. In a preferred embodiment, the cooling rate can range between about 1-10° C./m, and any whole or partial increments therebetween. For example, the cooling rate (° C./m) can be about 0.1, about 0.5, about 1, about 2, about 3, about 4, about 5, about 5.5, about 6, about 6.5, about 7, about 7.5, about 8, about 8.5, about 9, about 9.5, or about 10. The cooling rate can be achieved by, for example, the use of a PID controller, a band heater wrapped around the cold finger, a thermocouple imbedded under the surface of the cold finger, and submerging the opposite end of the cold finger in a bath of liquid nitrogen. In this way, the band heater counteracts the thermal diffusion of the liquid nitrogen and power is slowly reduced by the PID controller to ensure an even cooling rate. The cold finger can be held steady at about 5° C. to begin, and slowly lowered to about −150° C. Upon reaching −150° C., the cold finger can be held steady until the entire sample is frozen solid.

Scaffold Morphology and Mechanical Strength

In one aspect of the invention, the overall morphology of the freeze-cast polymer scaffolds is characterized by regions of aligned pores, or lamellae. In another aspect, ridges are formed along the lamellae and can protrude substantially perpendicular and uniformly in only one direction of the lamellae wall, creating a series of substantially parallel grooves between ridges. In one embodiment, the ridges along the lamellae are spaced about 1-50 µm apart, and any whole or partial increments therebetween. In preferred embodiments, the spacing between ridges can be about 10 µm, about 15 µm, about 20 µm, about 25 µm, about 30 µm, about 35 µm, about 40 µm, about 45 µm, or about 50 µm. Formation of these ridges is controlled by manipulation of the local freezing front velocity and cooling rate experienced by the sample during freeze casting. In one embodiment, ridges are generated along the lamellae when the cooling rate is equal to or greater than about 6° C./min. The formation of ridges, as well as the spacing between ridges, can also vary depending on the type and combination of polymer materials used.

In another aspect, the scaffolds include excellent pore alignment, with pore diameters of between about 10-200 µm, and any whole or partial increments therebetween. In certain embodiments, pore diameters can range between about 10-50 µm, and any whole or partial increments therebetween. In preferred embodiments, pore sizes can be about 10 µM, about 15 µm, about 20 µm, about 25 µm, about 30 µm, about 35 µm, about 40 µm, about 45 µm, or about 50 µm. The selection of pore size within the scaffold can be controlled by manipulation of the local freezing front velocity and cooling rate experienced by the sample during freeze casting. The selection of pore size can also be controlled by selection of the type and combination of polymer materials used.

In another aspect, the scaffolds have a Young's modulus of about 1-15 kPa, and any whole or partial increments therebetween. In preferred embodiments, the modulus can be about 1 kPa, about 2 kPa, about 3 kPa, about 4 kPa, about 5 kPa, about 6 kPa, about 7 kPa, about 8 kPa, about 9 kPa, about 10 kPa, about 11 kPa, about 12 kPa, about 13 kPa, about 14 kPa, or about 15 kPa. In a preferred embodiment, the modulus can be 3-5 kPa. The resulting modulus of various portions of the scaffold can be controlled by manipulation of the local freezing front velocity and cooling rate experienced by the sample during freeze casting. The modulus can also be controlled by selection of the type and combination of polymer materials used.

In yet another aspect, the scaffolds have a plateau strength of about 0.1-1 kPa. In preferred embodiments, the plateau strength can be about 0.1 kPa, about 0.2 kPa, about 0.3 kPa, about 0.4 kPa, about 0.5 kPa, about 0.6 kPa, about 0.7 kPa, about 0.8 kPa, about 0.9 kPa, or about 1 kPa. The resulting plateau strength of various portions of the scaffold can be controlled by manipulation of the local freezing front velocity and cooling rate experienced by the sample during freeze casting. The plateau strength can also be controlled by selection of the type and combination of polymer materials used. The plateau strength can also be controlled by selection of the type and combination of crosslinkers used.

In yet another aspect, the spacing of lamellae within the scaffold can range between 5-200 µm. In preferred embodiments, the spacing between lamellae can be about 5 µm, about 10 µm, about 15 µm, 20 µm, about 40 µm, about 60 µm, about 80 µm, about 100 µm, about 120 µm, about 140 µm, about 160 µm, about 180 µm, or about 200 µm. The spacing of the lamellae within the scaffold can be controlled by manipulation of the local freezing front velocity and cooling rate experienced by the sample during freeze casting. The spacing of the lamellae within the scaffold can also be controlled by selection of the type and combination of polymer materials used.

In selected embodiments, the bottom layers of the scaffolds have a consistently higher modulus and smaller lamellae spacing, which leads to a more tightly packed system of supporting lamellae. This is due in part to the freezing front velocity and the local cooling rate being faster at the bottom of the sample.

In certain embodiments, the positive charge (if any) on the scaffold can be neutralized. The neutralization of the positive charges can change the solubility of the chitosan within PBS, allowing the scaffold to retain its shape and not dissolve. Neutralization also brings the scaffolds of the present invention to the approximate kPa values of host, or native tissues. Thus, in another aspect, the mechanical values of scaffolds soaked in PBS can approximate the kPa values of host tissues, and can be further modified by different neutralization methods. One such method includes the use of calcium chloride to neutralize the chitosan scaffolds and make them stable in PBS.

For example, in one embodiment, the properties of the scaffold are controlled through directional freezing, scaffold composition and the degree of cross-linking. The resulting scaffold structure preferably has a substantially aligned porosity, where porosity is approximately 97%, and the Young's modulus is preferably in the range of 3–5 kPa. In other embodiments where the scaffold has approximately 97% porosity, the Young's modulus of Gelatin can be in the range of 11.6–17.6 kPa in the dry state and in the range of 25.6–30.4 kPa in the wet state. As may be the case with Chitosan, the Young's modulus can be in the range of 12–2.7 kPa in the wet state.

Directional Control of Neuronal Growth

In another aspect of the present invention, the polymer scaffolds described herein can be used to control the guide neuronal growth while best matching the material properties of the native tissue. Thus, the present invention includes a method of guiding the direction of neuron growth, including the steps of engaging at least one neurite with the grooves along the lamellae of a scaffold, such that outgrowth of the neurite is channeled substantially along the linear axis of the grooves.

The present invention also includes a method of connecting two or more neurites, including the steps of engaging at least two neurites along the length of the grooves of the lamellae of a scaffold, such that the outgrowth of the neurites is channeled substantially along the linear axis of the grooves towards each other.

The present invention also includes a method of controlling directional outgrowth of a neurite, including the steps of engaging at least one neurite with the grooves along the lamellae of a scaffold, such that outgrowth of the neurite is stunted from growing in a direction that is tangentially skewed from the linear axis of the grooves.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

The following methods and materials were used in the experimental examples presented herein.

Polymer Preparation

Varying combinations of chitosan and gelatin, each dissolved in 1% (v/v) acetic acid, were created and analyzed. To prepare the chitosan solution, 2.4 grams of low molecular weight chitosan powder was weighed (XP105 Delta Range Balance, ±0.01 mg, Mettler Toledo Inc., Columbus, Ohio) and placed in a glass amber-colored jar with 100 ml of 1% (v/v) glacial acetic acid in de-ionized (DI) water so as to produce a 2.4% (w/v) solution. This solution was then mixed on a Wheaton bench top roller machine at approximately 10 rpm for a minimum of 24 hours to ensure complete dissolution of the chitosan. To avoid potential degradation of the chitosan in solution, not only was the jar amber-colored but solution more than 1 week old was not used. The gelatin solution was prepared by weighing 5.5 grams of gelatin powder and placing the powder in a beaker with 100 ml of 1% (v/v) glacial acetic acid in DI water to create a 5.5% (w/v) gelatin solution. Dissolution was achieved by magnetically stirring a Teflon-coated magnetic stir bar inserted into the solution at 60 rpm while heating the solution on a VWR hot plate stirrer to 35° C. for a minimum of 12 hours.

Prior to freezing, the solutions of chitosan and gelatin were combined in a mixing cup specific to the mixing unit, a high shear SpeedMixer (DAC 1510 FVZ-K, FlackTek, Landrum, S.C.) at 2400 rpm for 2 minutes.

Freeze Casting

Freeze casting is a material processing technique based on the principles of directional solidification to control the properties and structure of a material in solution by slowly advancing unidirectional temperature gradient during the freezing process to form unidirectional pores [Wegst U, et al., 2010, Phil Trans R Sac A 368:2099-2121]. It creates the porous scaffolds by trapping the material between the ice crystals that form. The ice is removed through freeze-drying, or sublimation, which results in a porous scaffold of the material that was in solution. By freezing the solution in a uniform direction, the formed pores align and extend in the direction of the freezing. Pore size, geometry and porosity of the whole sample can be specifically tailored to an application. Additionally, mechanical properties can be altered by crosslinking the polymer before or after freezing [Meg et al., 2010, JOM-J Min Met Mat S 62 (7):71-75]. Crosslinking the polymer during the freezing process can also be performed.

The solutions were freeze cast in two differently sized molds. The first, used for mechanical testing, most imaging, and in-vitro analysis, was a 25 mm O.D.×50 mm tall cylinder mold with a tightly fitting copper mold placed on the bottom of the cylinder so as to provide a controlled thermal transfer from the cold finger upon which the cylinder is placed; the top of the cylinder was left open to the ambient air conditions. The second mold, which was used to prove the feasibility of future in-vivo models, was composed of two halves, with half-circle groves along the mating edge (FIG. 1).

A circular depression was milled out of one side, such that a copper disk fit snugly. The copper disk side was then placed on the cold finger in the same fashion as the larger cylinder mold. When pipetting into such small molds, it was critical that air bubble formation be avoided; this was achieved by placing a micropipette on the open end of one of the grooves and repeatedly flushing the entire canal system until the residual air was flushed out. Both large and small molds were placed with the copper plate on the copper cold finger of the freeze casting system and secured with a tight wrapping of electrical tape. Once secured, the solution was pipetted in as described and then the copper cold finger was cooled down at various rates, ranging from 0.1 degrees Celsius per minute to 10 degrees per minute (° C./m). This was achieved by the use of a PID controller, a band heater wrapped around the copper cold finger, a thermocouple imbedded under the surface of the cold finger, and submerging the opposite end of the cold finger in a bath of liquid nitrogen. The band heater counteracted the thermal diffusion of the liquid nitrogen and power was slowly reduced by the PID controller to ensure an even cooling rate. The cold finger was held steady at 5° C. to begin, and slowly lowered to −150° C. Upon reaching −150° C., the cold finger was held steady until the entire sample was frozen solid. This was determined visually, as ice crystals condensed on the surface of the frozen sample.

Figure 33:
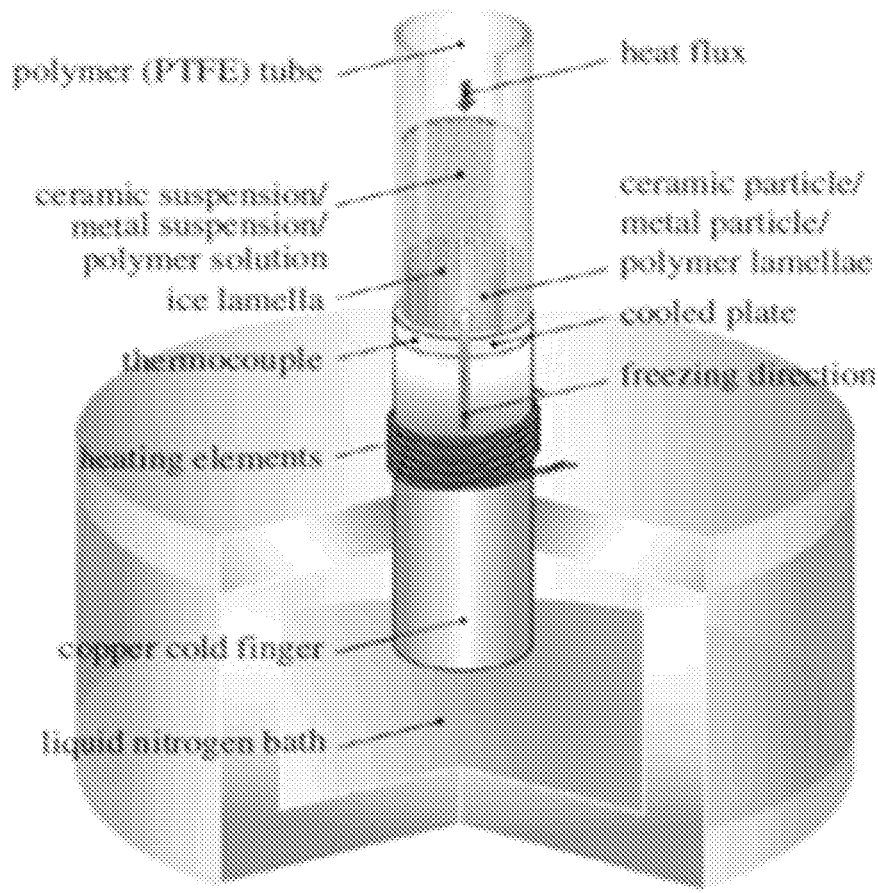
FIG. 33 is a schematic depicting the construction of the freeze-easter.

Further, a freeze-caster was constructed (FIG. 33) by suspending a copper cold finger in a bath of liquid nitrogen. Attached to the copper cold finger on the top end was a heating element and thermocouple which were connected to a control system linked to a computer that monitors and regulates the temperature. The solution is poured into the mold with the cooper plug and placed on top of the copper cold finger. The desired cooling rate can then be selected and run using the computer program.

Lyophilization

Once the freezing process was completed, the samples were removed from their molds, wrapped in Kimwipes, and placed in a FreeZone 4.5 Liter Benchtop Freeze Dry System (Labconco, Kansas City, Mo.). The inner coil was held at −50° C. and the samples themselves at 0.18 mBar for at least 48 hours to ensure complete sublimation of the ice. Removal of the larger samples was performed with a Teflon punch attached to an Arbor press; removal of the smaller samples was performed manually with a wooden toothpick.

Sectioning

Sectioning of the samples was performed with a 220 μm diameter diamond-imbedded steel wire Well 4240 saw (WELL Diamond Wire Saws, Inc, Norcross, Ga.) with a wire speed of 0.7 m/s. The cylindrical samples were mounted on ceramic disks with Crystalbond 509 (Aremco Products, Inc, Valley Cottage, N.Y.); the ceramic disk was used to position the samples within the saw. Samples were sectioned in similar fashion, such that the three layers used for mechanical testing came from the same height within each sample. Within each layer used for mechanical testing 4 cubes, measuring 5 mm×5 mm×5 mm each, were cut out. These cubes were marked with a dot on the bottom-right corner prior to the last cut so that subsequent mechanical testing was performed on the same surface in the same direction for all of the samples. Approximately 4 mm separated each layer used for mechanical testing; these 4 mm were cut into two cross-section slices and used for various tests, including swelling, imaging, and in-vitro analysis.

Testing and Evaluation Procedure

Mechanical testing was performed on an Instron Model 4440 single-column bench-top machine with two different load cells. For dry scaffold testing, a 50 Newton (N) load cell was used; for wet scaffold testing, a 5 N load cell was used. All testing was done in compression with a cross-head speed of 0.05 minis and tested in the axial direction, with the load parallel to the direction of both pores and lamellae walls. After the samples were sectioned they were weighed for later density calculations and imaged for pore size analysis.

Samples tested in the wet environment were tested in PBS; however, prior to testing in PBS, the positive charge on the chitosan scaffold was neutralized. Neutralization was achieved by a 15 minute soak in a 0.4% glacial NaOH in 95% ethanol solution, followed by rinsing in ethanol for approximately 30 seconds. The neutralization of the positive charges changed the solubility of the chitosan within PBS, allowing the scaffold to retain its shape and not dissolve. A permanent black Sharpie marker was used to mark the corner of the scaffold; the markings faded slightly, but were still visible, after the charge neutralization and soaking in PBS. All scaffolds tested in PBS were soaked for 24 hours prior to testing.

In another embodiment, the wet samples were soaked in $CaCl_2$ for 10 minutes, dipped in DI water and then soaked in HEPES for 30 minutes. HEPES (4-(2-hydroxyethyl)-1-piperazineethanesulfonic acid) is a zwitterionic organic chemical buffering agent. This was chosen as a buffer because it is chemically stable, has a pH range of 6.0 to 8.0, high solubility and has limited effects on biochemical processes.

Figure 2:
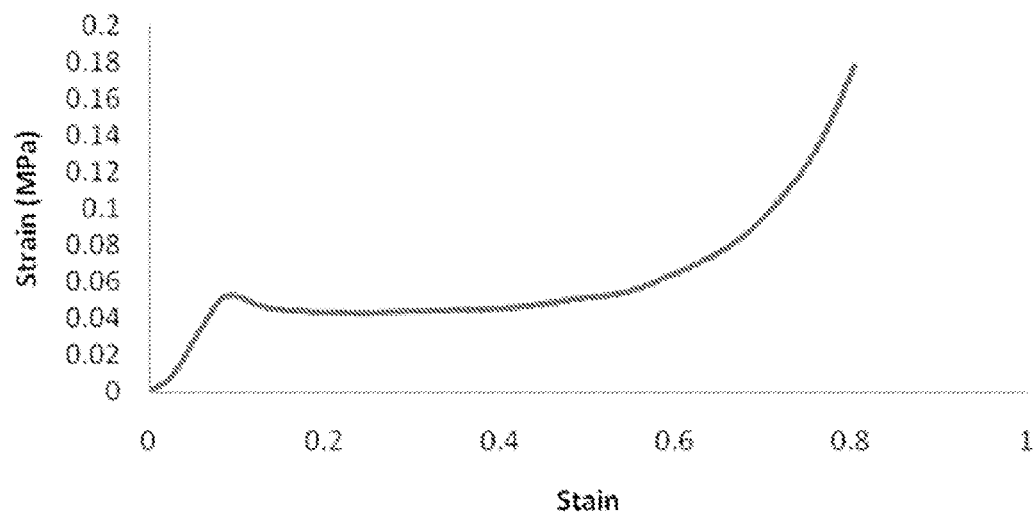
FIG. 2 is a representative stress-strain plot of a 100% chitosan scaffold tested in dry conditions. Modulus (slope of the initial linear region) and plateau (horizontal value post-yielding) were extracted.

Extension and load, the raw data generated from the Instron machine, were converted to strain and stress, respectively, by dividing the extension by the length of the entire sample (5 mm) and by dividing the load by the cross-sectional area of the sample (25 $mm^2$). These were used to generate a stress-strain plot (FIG. 2), from which the modulus and plateau strength of the samples were extracted.

Imaging

Figure 3:
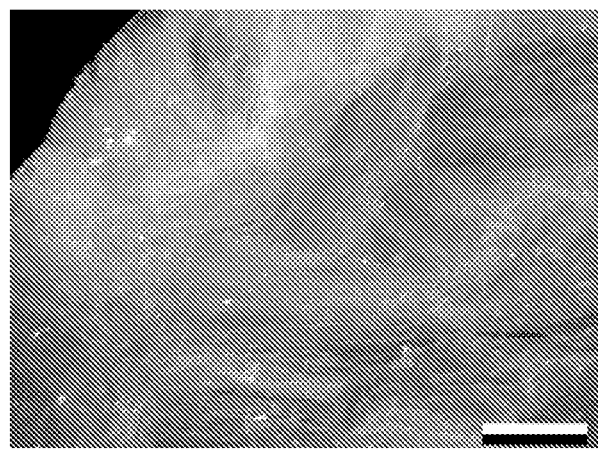
FIG. 3 is a cross-sectional optical microscope image of 100% chitosan scaffold frozen at 6 degrees/minute. Scale bar is 2 mm.

Optical imaging of the dry scaffolds was performed on a Leica Microsystems DFC400 optical microscope (Leica Microsystems, Ltd, Germany). SEM imaging was performed with a Zeiss Supra 50VP (Carl Zeiss SMT Inc, Peabody, Mass.) located in Drexel University's Centralized Research Facility. To measure and analyze both types of images, imaging software (ImageJ, U.S. National Institute of Health, Bethesday, Md.) was used. No sample preparation was required for the optical microscopy; however, SEM preparation was required. For the two-dimensional single lamellae mounted on glass cover slides, the lamellae were dehydrated from their PBS-soaked state with a series of 10-minute immersions in ethanol-water solutions (30, 50, 70, 90%) followed by an overnight immersion in 100% ethanol before final dehydration in ambient conditions. The glass cover slides were mounted onto the SEM sample stubs with a layer of carbon and then sputtered with platinum-palladium for 30 seconds. Larger samples not mounted on glass cover slides were directly placed on the layer of carbon, itself in turn placed directly on the SEM sample stub. Conductive silver paint was placed on one side of the samples to ensure conductivity from the top of the sample to the stub, and then the samples were sputtered as before. Optical imaging of the stained neurons propagation along the scaffolds was performed on an Olympus IX71 Fluorescence Microscope, In-Vitro Testing In-vitro analysis was performed, and a cross-sectional image of the chitosan scaffolds is shown in FIG. 3. As depicted in FIG. 3, the overall morphology of the freeze-cast chitosan scaffolds can be seen, characterized by regions of aligned lamellae. For two-dimensional testing it was necessary to isolate individual lamellae; for three-dimensional testing it was necessary to prepare a clean-cut surface for the cells to propagate down.

Two-Dimensional Lamellae Isolation

Figure 4:
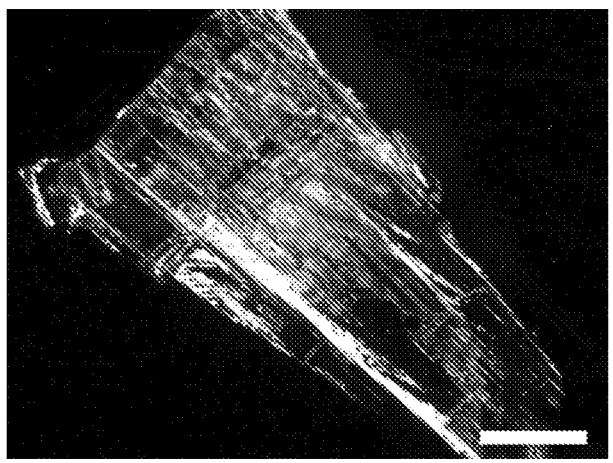
FIG. 4 is an image of a single lamellae isolated from a pure chitosan scaffold frozen at 6 degrees/minute. Scale bar is 1 mm.
Figure 5:
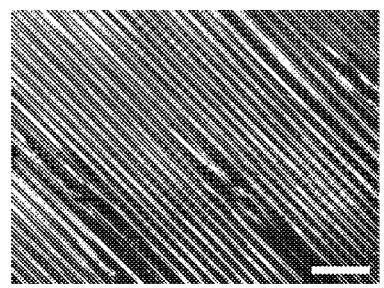
FIG. 5 is an image illustrating the grooves formed along the individual chitosan lamellae. Scale bar is 100 μm.

Two-dimensional analysis was performed to determine whether or not the cells would align with the grooves formed within the pure chitosan scaffolds. Isolation of the individual lamellae was performed under the previously mentioned Leica Microscope and with the use of two Dumoxel #7 forceps. Cross-sections approximately 4 mm thick were sliced with surgical scalpels (FIG. 3). Once sliced, the lamellae were gently teased apart with the use of forceps until a single lamellae was isolated (FIG. 4). The purpose of single lamellae isolation was to expose the grooves (FIG. 5), Once exposed, the lamellae were placed on 5 mm×5 mm pieces of glass cover slides and wetted with two drops of 95% ethanol. As the ethanol dried, the lamellae gently stuck to the glass such that they could be easily pulled off; however, they were still sufficiently stuck to avoid floating during the subsequent neutralization and sterilization steps. Neutralization of the chargers was performed in the same fashion as described above, and sterilization was achieved by soaking the lamellae in 70% ethanol/DI-water solution.

Three-dimensional sections of scaffolds were prepared by slicing with surgical scalpels the chitosan scaffolds. Care was taken to ensure a cleanly sliced surface; lamellae sliced by other means were often pushed over. Various attempts were made to prepare 3-dimensional scaffolds for in-vitro analysis. Multi-lamellae peelings were isolated (ranging from 2 to 7 lamellae thick) and either laid down on glass cover slides or pinched on one side with a polypropylene clip that held the lamellae upright. Slices of varying thicknesses were sectioned with surgical scalpels; these were also either laid down on glass cover slides or of sufficient cross-sectional area to stand upright on their own. All three-dimensional scaffolds produced were neutralized and sterilized as described above.

In-Vitro Testing and Evaluation Procedure

Figure 6:
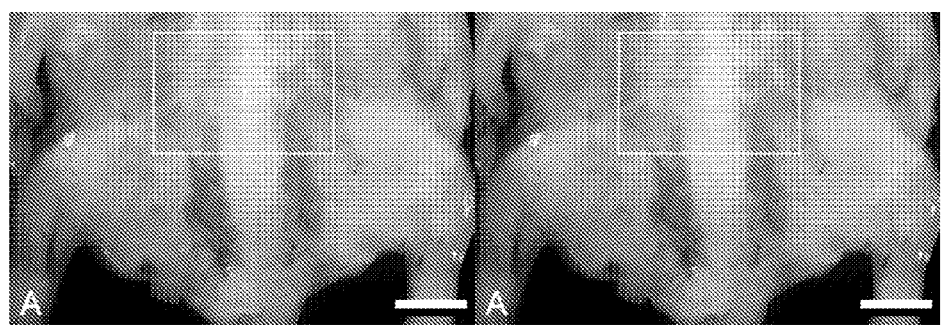
FIG. 6 is an in-situ optical micrograph of exposed chick embryonic spinal cord. DRGs present as spheres located on either side of the vertebrae. At this point the caudal 12 DRGs have already been excised; 4 remain clearly visible. Scale bar is 1 mm. (B) Magnified image of white box in (A), showing the remaining DRGs: two on the left, unmarked, and two on the right, circled. Scale bar is 500 μm.

Chick embryos were sacrificed on day 10 (E10), and DRGs were harvested from the spinal cord (FIG. 6). Excised DRGs were cultured on or in the scaffolds in DMEM medium with 10% fetal bovine serum, 1% antibiotic, and 100 ng/ml NGF for 24 or 48 hours prior to analysis. The primary antibody staining for neuron extension was mouse anti-neurofilament 200 (NF200); the secondary antibody stain was goat anti-mouse Alexa Fluor 488. Both whole DRGs and individual neurons were cultured on the isolated individual lamellae; individual neurons were obtained by manually pipetting the DRGs to break up the agglomeration. Fluorescent microscopy was used to visualize the growth of the neurons.

Example 1

Generation of Chitosan Scaffolds

Figures 30A, 30B:
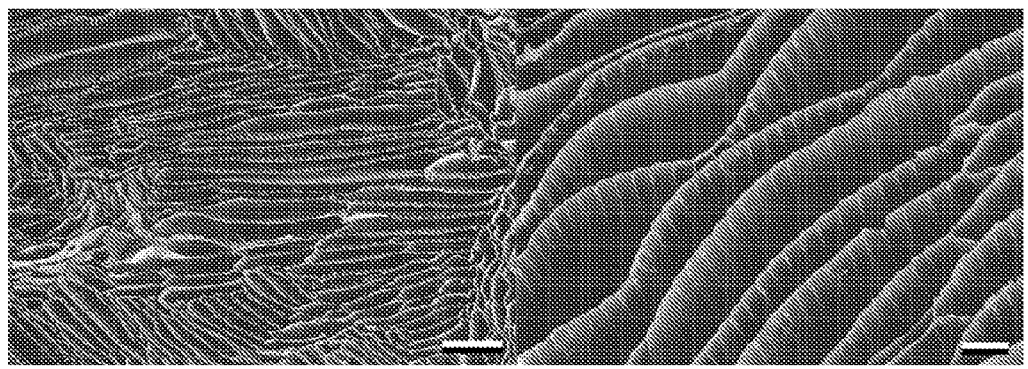
FIGS. 30A and 30B are magnified images of a small-diameter scaffold. Scale bar for FIG. 30A is 200 μm; scale bar for FIG. 30B is 40 μm.

Demonstrated herein is an analysis of how the freezing rate, from 0.1° C./m to 10° C./m, affects the mechanical properties of the resultant chitosan scaffolds. Scaffolds were mechanically evaluated in both dry (ambient air) and wet (soaked in PBS) conditions. FIGS. 30A and 30B depict how the modulus and plateau strength (both MPa) vary according to the freezing rate in dry conditions. For each freezing rate, 3 layers were tested; the middle-height from the sample's bottom of the three layers is given in Table 1.

TABLE 1

Height (mm) from the bottom of the sample to the bottom, middle, and top of each layer.

| Layer | Bottom of Layer | Middle of Layer | Top of Layer |
|---|---|---|---|
| Top | 25.33 | 27.83 | 30.33 |
| Middle | 14.83 | 17.33 | 19.83 |
| Bottom | 4.33 | 6.83 | 9.33 |

Three layers were mechanically tested from each sample.

Figure 7A:
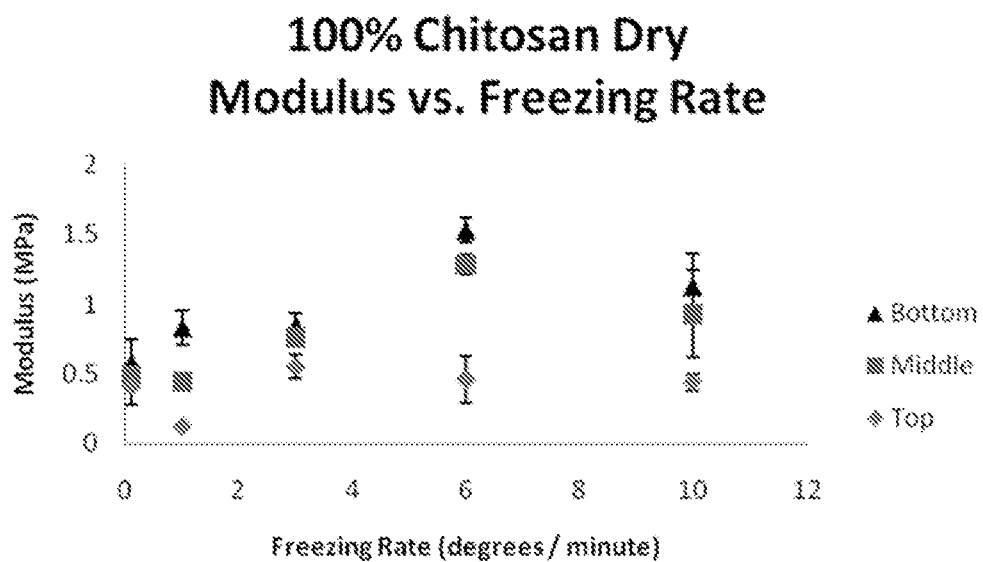
Figure 7B:
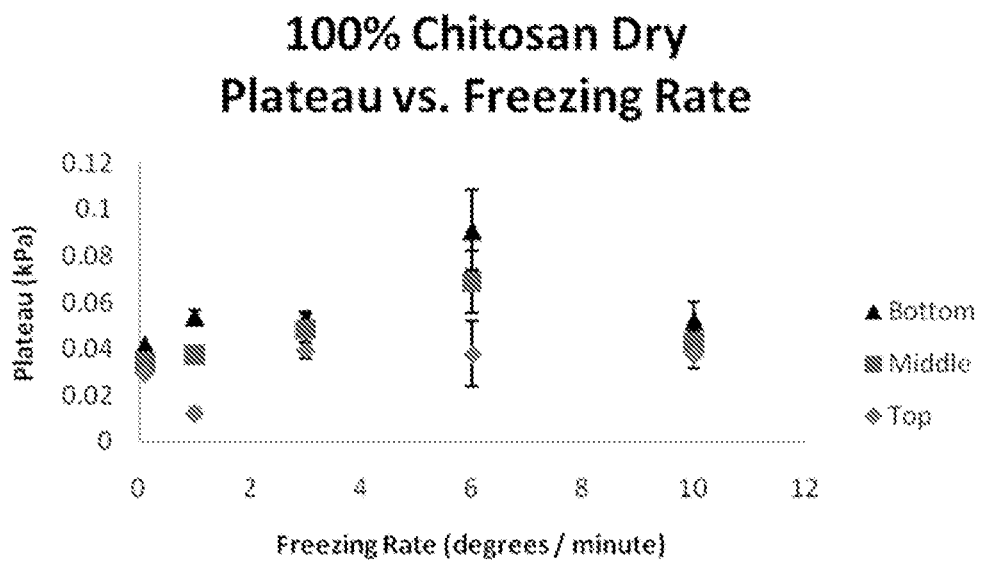
FIG. 7B is that of the plateau strength's dependence on freezing rate.

From FIGS. 7A and 7B, one can clearly see the change in values from within each sample; the bottom layer has a consistently higher modulus and plateau, while the top layer performs weaker than the other two. This is because within each sample, both the freezing front velocity and the local cooling rate are seen to be faster at the bottom of the sample. This result is consistent with the general trend that with faster freezing velocities and cooling rates come smaller lamellae spacing, which leads to a more tightly packed system of supporting lamellae. This in turn leads to both stiffer and stronger buckling limits when a load is applied. All general trends have limits, however, and the data support the theory that when the sample is frozen at 10° C./m, the decreasing lamellae spacing results in a decreased lamellae wall thickness that compromises some of the structural integrity. Within the faster freezing rates, this decrease in lamellae spacing stiffens the structure. However, when the freezing rate is increased to 10° C./m, the decrease in lamellae wall thickness is sufficient to reduce the mechanical properties, despite a more tightly packed lamellae architecture.

During the freezing of the faster freezing rates (6 and 10° C./m) it was noticed that throughout the bottom ⅔ of the 10° C./m and throughout the bottom half of the 6° C./m (which experiences a faster freezing rate than the top) small ridges were forming along the lamellae. These ridges did not act as full bridges seen in previously freeze-cast structures, but rather protruded perpendicular to the lamellae wall and, interestingly, protruded uniformly in only one direction of the lamellae wall. The formation of these ridges was directly correlated to the local freezing front velocity and cooling rate experienced by the sample, and from the mechanical data plots one can see that the formation of these ridges serve to add support to the lamellae. This result is plausible, as the ridges would serve to increase the second moment of area of each lamella, which in turn would stiffen the lamellae against both bending and buckling.

Figure 13A:
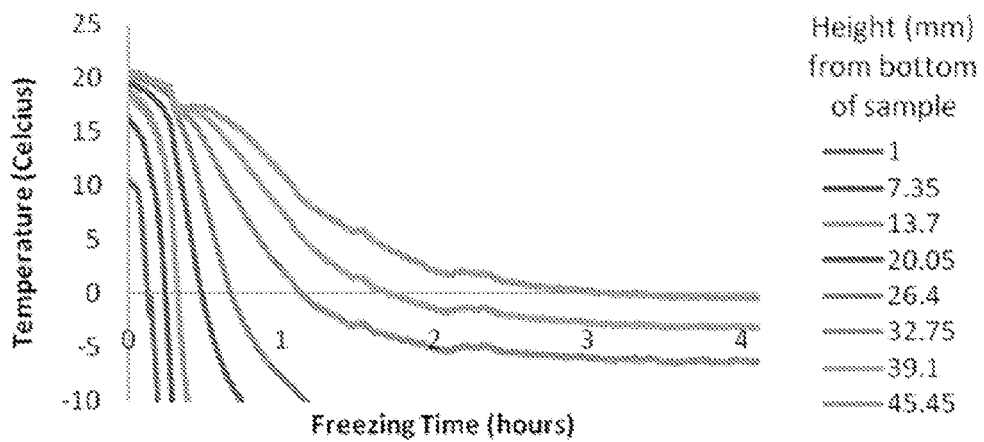
FIG. 13A is a chart of the temperature throughout the sample as it freezes.
Figure 13B:
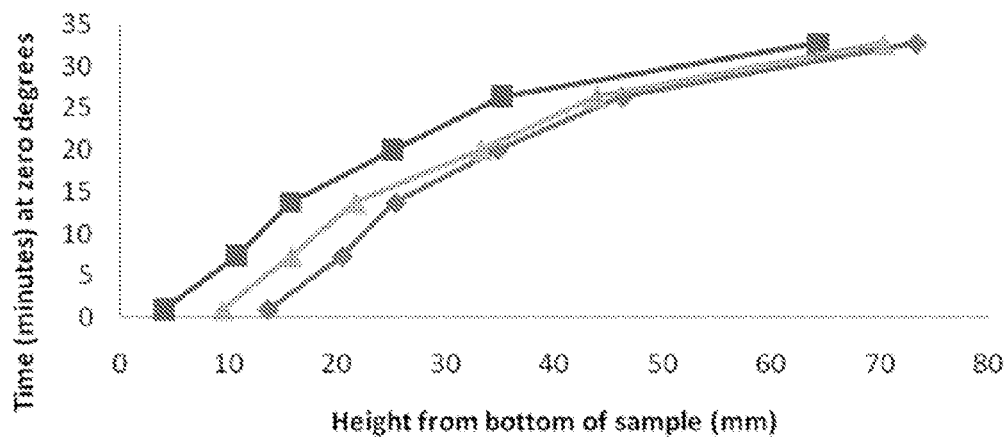
FIG. 13B is that of time each thermocouple reached zero degrees for three different samples. The slope of FIG. 13B at the various heights along the sample is thus the freezing front velocity at that height, and is plotted in FIG. 14A. The slope of FIG. 13A at zero degrees is the local cooling rate, and is plotted in FIG. 14B.

To investigate the local freezing front velocity within the 6° C./m samples, which experience a transition from ridge-formation to no ridge-formation within the same sample, a sample mold with thermocouples embedded within the walls was used to freeze thrice. Data from the thermocouple yielded the temperature at various heights along the sample throughout the freezing process (FIG. 13A).

Figure 14A:
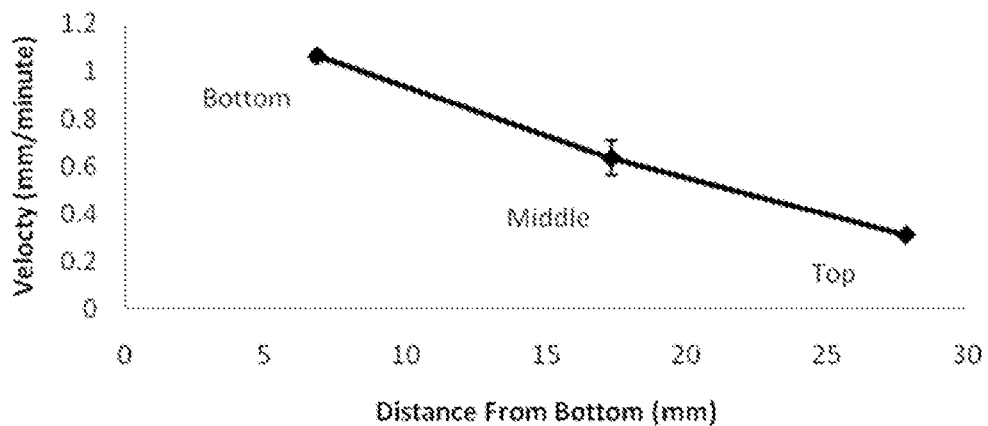
FIG. 14A is a chart of the freezing front velocity along the sample height, calculated from the slope of FIG. 13B at the various heights.
Figure 14B:
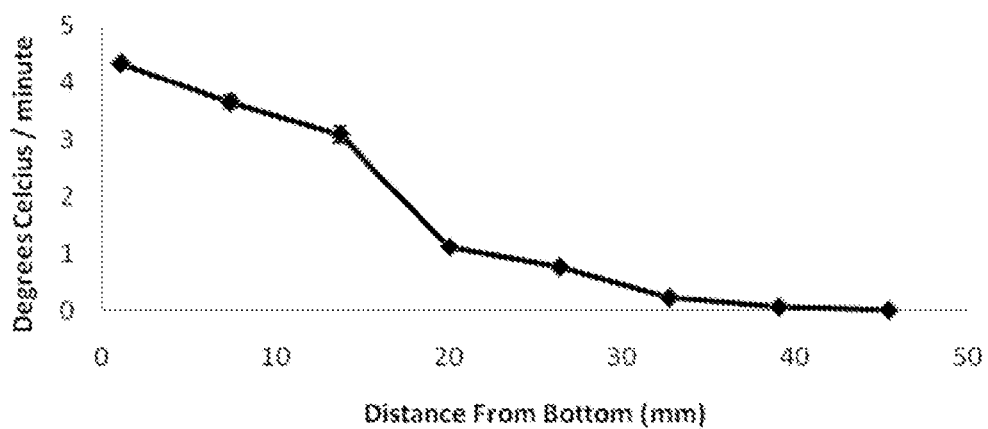
FIG. 14B is that of the local cooling rate, and is calculated from the slope of FIG. 13A at the zero degree temperature for the various heights along the sample.

From the thermocouple-mold data the time at which the various heights reached zero degrees were determined and plotted against the heights; the slope of this line was considered to be the freezing front velocity within the sample at the given height (FIG. 14A). The local cooling rate was also calculated by determining the slope of 13A (temperature vs. time) when the thermocouples passed the zero degree temperature. According to the theory of undercooling when the thermocouples register zero degrees, the solution is not quite frozen; however, as no study was taken to determine the precise temperature at which the solution does solidify, zero degrees was used.

The following optical micrograph was taken from a 6° C./min middle-layer lamellae. The height from the bottom of the sample was approximately 17 mm, which correlates to a freezing front velocity of approximately 0.6 mm/min and a local cooling rate of approximately 2° C./min. It is interesting to note that at this transition height of 15 to 20 mm, where the ridges were seen to disappear, that the local cooling rate experiences a much more rapid decrease than the freezing front velocity. This result is in good agreement with the theory that the local cooling rate, which dictates how quickly the slush-zone of undercooling solution is decreasing in temperature, affects the formation of ridges and lamellae more so than the speed at which the solution reaches zero degrees. If the sample did not experience any undercooling then one would expect the two to decrease at the sample rate; however as the data shows that the freezing front velocity and local cooling rate decrease at different rates the theory of undercooling is supported.

Figures 15A, 15B:
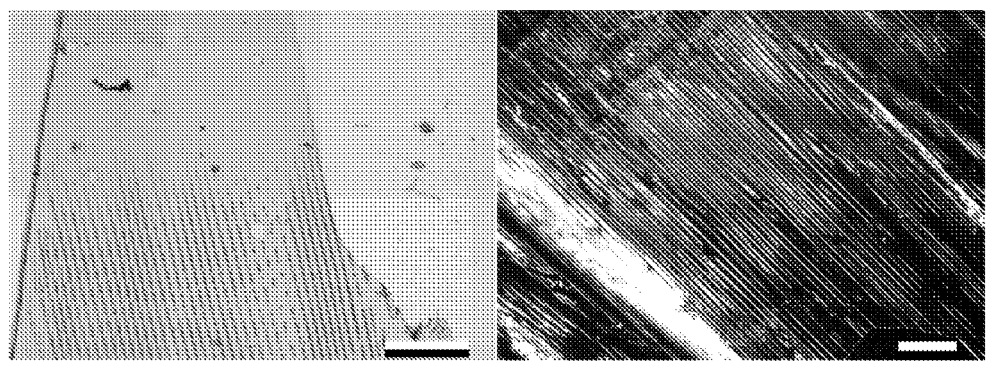
FIG. 15A is an image of a single lamellae approximately 17 mm from the base of the sample; this correlates to a local freezing front velocity of approximately 0.6° C./m and a local cooling rate of approximately 2 degrees per minute. Note the transition from partial ridge-formation (bottom) to only residual formation (top).
FIG. 15B is an image of a single lamellae isolated from a sample height of 7 mm, correlating to a freezing front velocity of 1 mm/minute and a local cooling rate of 3.5 degrees per minute. Scale bar is 200 μm for both.

The bottom layer, taken 10 min closer towards to the bottom of the sample than the lamellae in FIG. 15A, has a freezing front velocity of approximately 1 min/minute and a local cooling rate of 3.5 degrees per minute. This faster solidification results in less time for the diffusion of the water molecules out of the solute system; this in turns seems to cause a bunching-up of the polymer into folds, or ridges, that are highly dependent on the amount of time the water has to diffuse out of the system. Single-lamellae isolated from heights of 7 mm corroborate this, and can be seen in FIG. 15B.

Figure 8A:
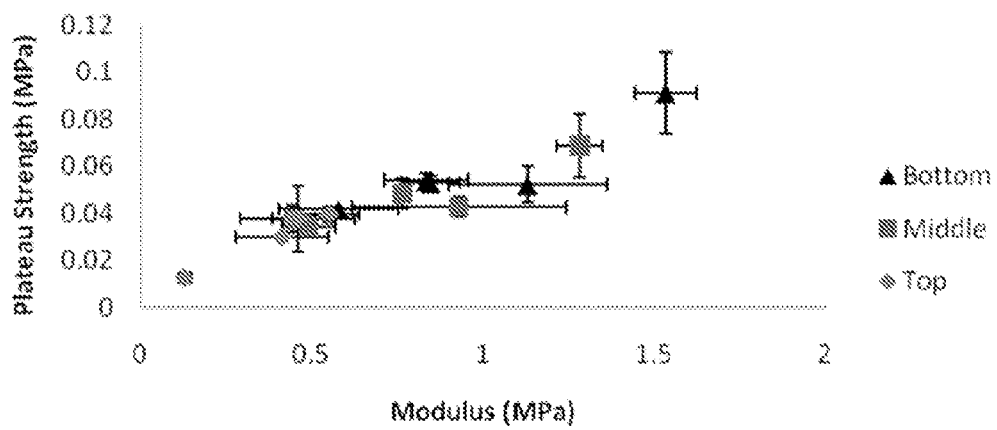
FIG. 8A is a chart of the plateau strength plotted against the modulus in the dry state, highlighting the differences of the three layers within the samples.
Figure 8B:
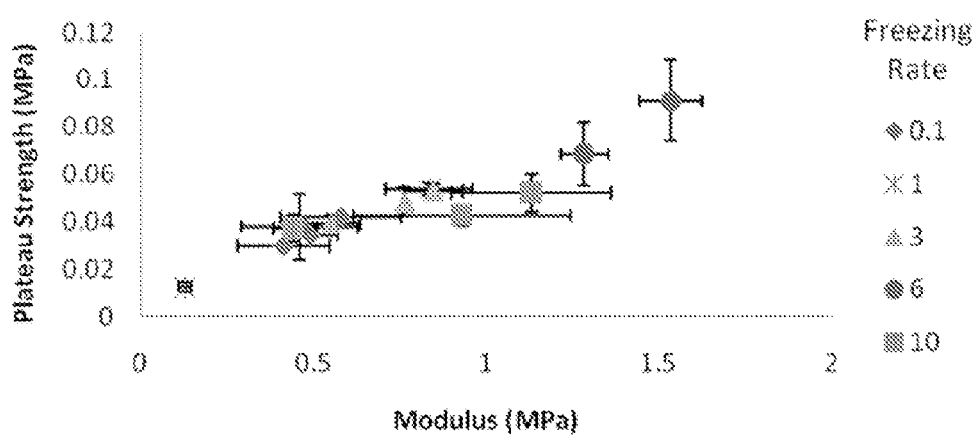
FIG. 8B are the same values plotted for the different freezing rates.
Figure 16:
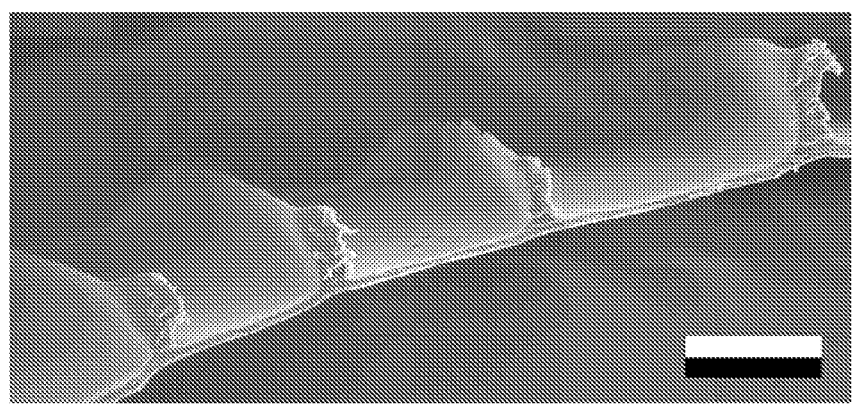
FIG. 16 is an SEM of a cross-section of a single lamellae isolated from a sample height of approximately 7 min, which correlates to a freezing front velocity of 1 mm/minute and a local cooling rate of 3.5 degrees per minute. Ridges act to stiffen the structure, increasing the second moment of bending much like half of an 1-beam. Scale bar is 5 μm.

FIGS. 8A and 8B plot the plateau strength vs. modulus within the dry state, highlighting either the layers (FIG. 8A) or the freezing rate (FIG. 8B). One can see a distinct cluster of 4 data points with moduli higher than 1 MPa; these data points correlate to the bottom two samples from 10° C./min and 6° C./min. What sets these samples apart is that the solidification rate within these samples was fast enough to cause ridges, which act increase the second moment of bending within the structures as a load is applied and can be clearly seen in FIG. 16.

The plot of strength vs. modulus also yields insight into the failure mechanism of the chitosan scaffolds. One can see that the modulus increases faster than the plateau strength; this result indicates that the lamellae are elastically buckling when a load is applied. If this is indeed the case, and assuming that the structure acts as an ideal honeycomb, as opposed to an equi-axed foam, we would expect the plateau strength, $\sigma_{pi}^*$, to scale with the modulus, $E^*$, as equation 10. If the structure were instead an equi-axed foam, plateau strength and modulus would scale as equation 11.

$$\sigma_{pi}^* = C * E^* \left(\frac{\rho^*}{\rho_s}\right) \tag{10}$$

$$\sigma_{pi}^* = C * E^* \left(\frac{\rho^*}{\rho_s}\right)^2 \tag{11}$$

Figure 17:
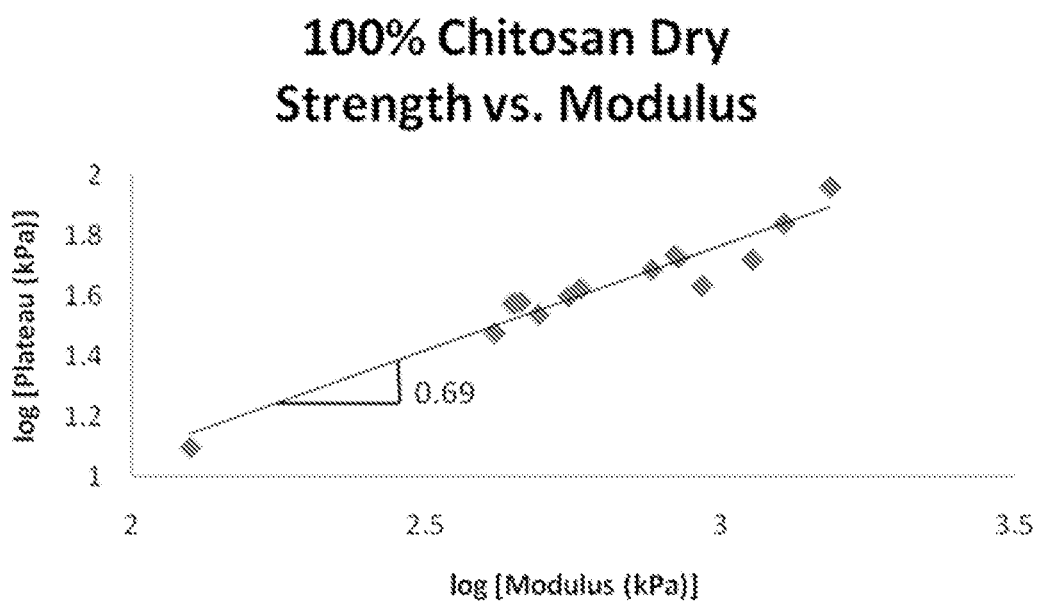
FIG. 17 is a chart depicting the plateau strength vs. modulus in dry conditions, related as $\sigma_{pt}'=0.058\ (E^*)^{0.69}$.
Figure 18:
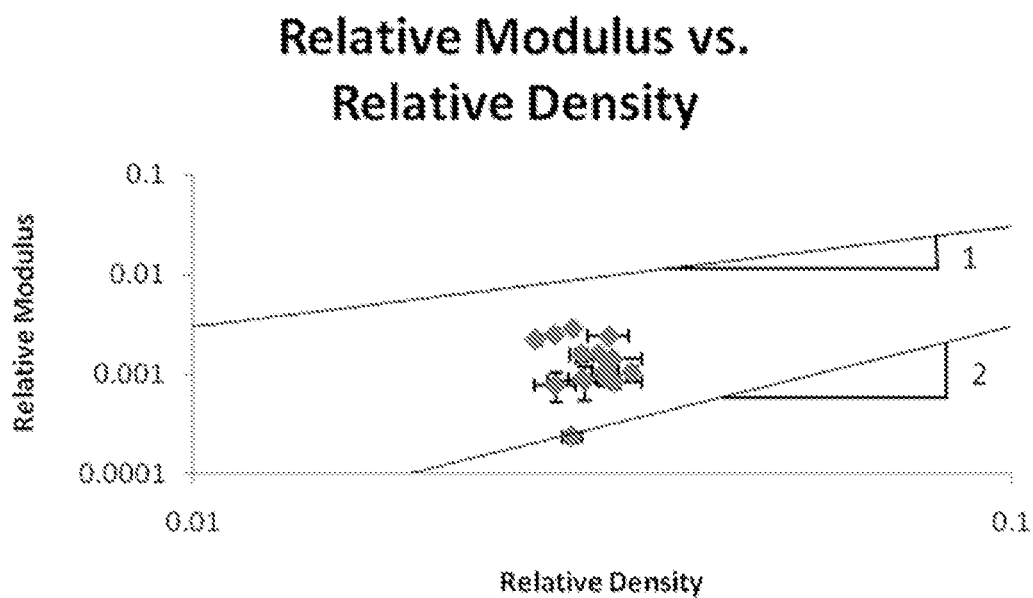
FIG. 18 is a chart depicting the relative modulus vs, relative density, assuming a density and modulus of 1.22 Mg/m³ and 534 MPa, respectively. A line of slope 1 indicates honeycomb-like stretch-dominated structures, while a slope of 2 indicates equi-axed foam-like bending-dominated structures. A correction factor of 0.3 was applied to the ideal case; this factor of 0.3 represents imperfections and deviations from the ideal, and has been empirically determined.

Replotting FIG. 8A as the log of the values (FIG. 17), one sees that the power falls shy of 1, which would indicate ideal honeycomb. SEM analysis shows that the scaffolds are not ideal honeycomb, but as the lamellae are linearly oriented they approximate honeycombs more so than equi-axed foams.

Scaling to the power of 0.69 is in close agreement with the values obtained in a related study of freeze-cast chitosan and gelatin blends, where Meghri et al. obtained a relationship of $\sigma_{pi}^* = 0.05 (E^*)^{0.9}$.

Figure 10A:
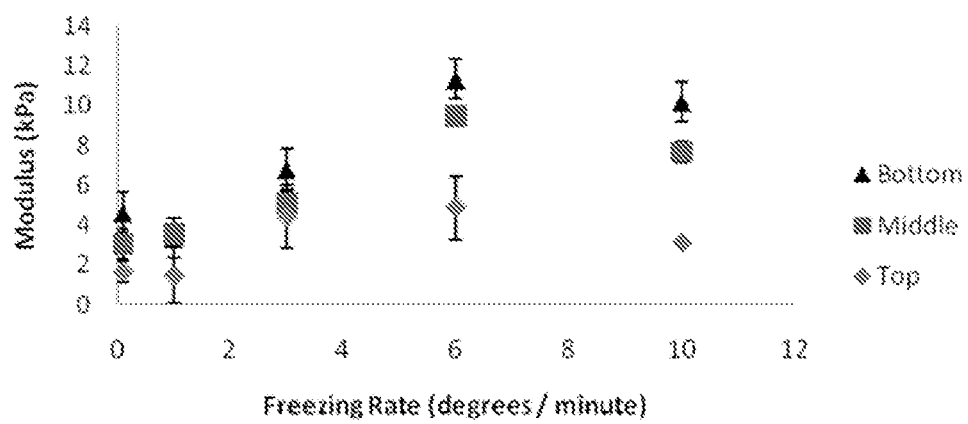
Figure 10B:
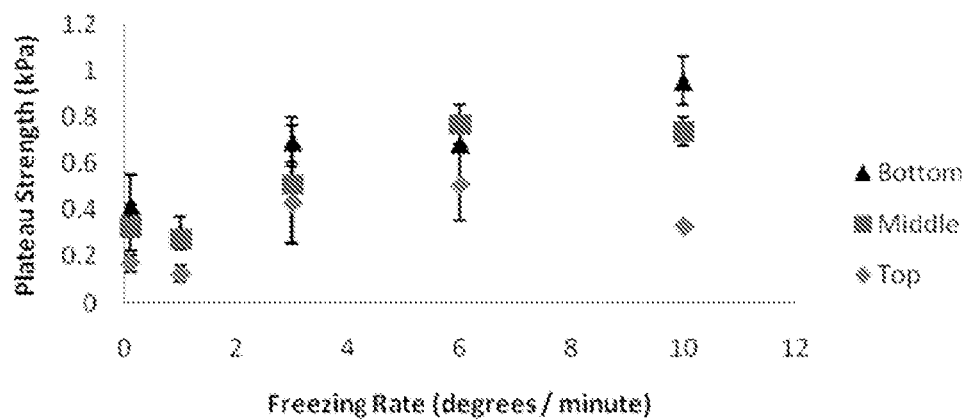
FIG. 10B is that of the plateau strength's dependence on freezing rate.
Figure 19A:
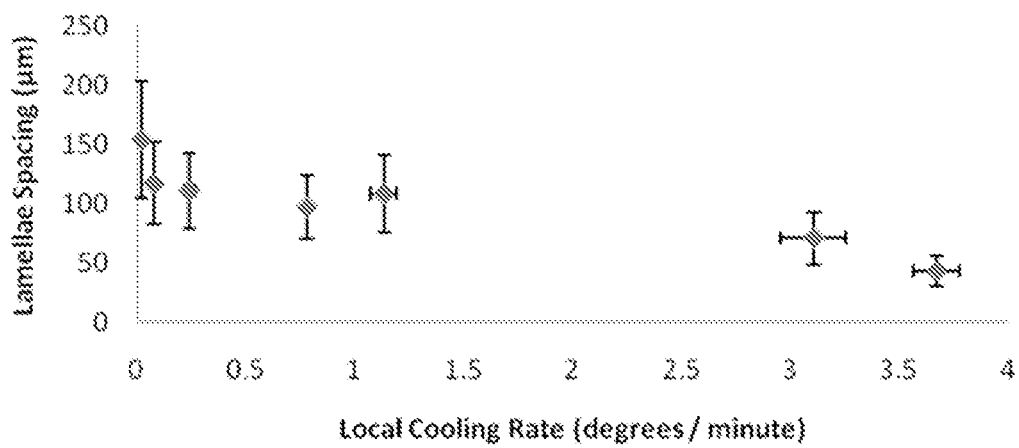
FIG. 19A is a chart of the lamellae spacing (μm) vs. local cooling rate (° C./m) of a 6° C./m sample.
Figure 19B:
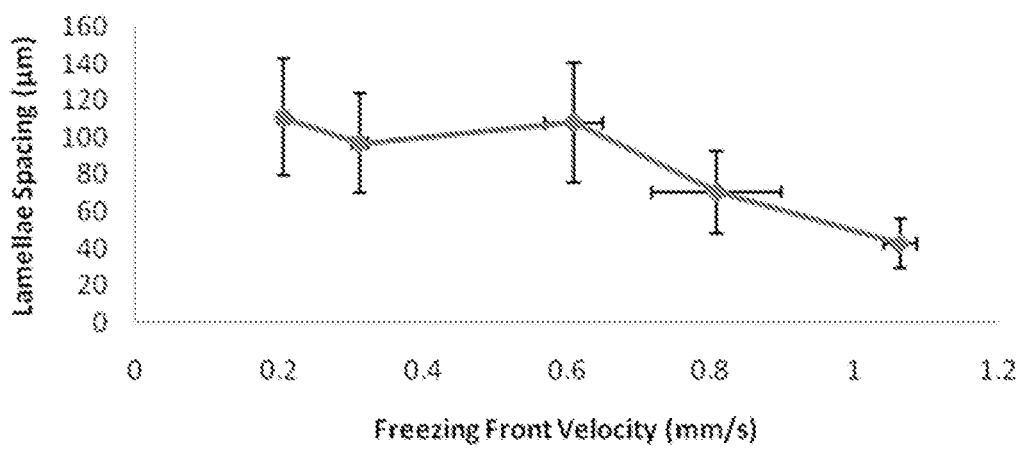
FIG. 19B is that of the lamellae spacing vs. freezing front velocity (mm/s) in the same sample.
Figures 20A, 20B:
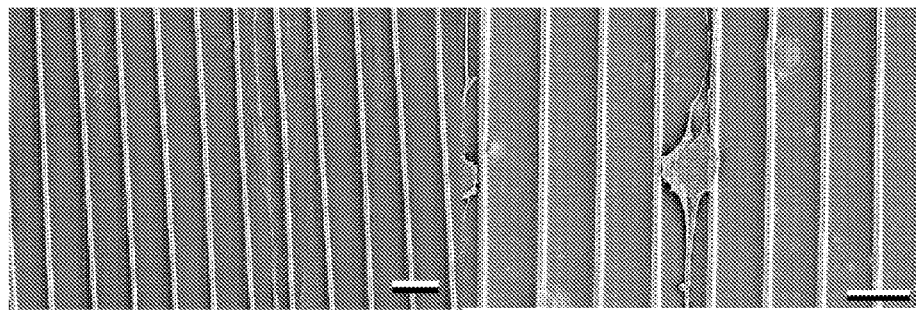
FIGS. 20A and 20B are both SEM images of neurons cultured on laminin-coated isolated lamellae.

FIGS. 10A and 10B, those of the relative modulus vs. relative density, reveal again a data cluster that performs better at the same relative density. These data points are the same outliers as in the strength vs. modulus plots, and are the samples that contained ridges. According to the Gibson-Ashby model of foam and porous structure failures, the relative modulus, $$\frac{\varepsilon^*}{\varepsilon_s},$$

scaled with the relative density, $$\left(\frac{\rho^*}{\rho_s}\right),$$

according to equations 12 and 13 depending on whether or not the structure is that of an ideal honeycomb (12) or that of an equi-axed foam (13). Deviations from the ideal exist, however, and an empirically derived correction factor of 0.3 has been determined for this relationship [Ashby, 2005, Philosophical Magazine 85(26): 3235-3257]. Plotting this relationship along with equations 12 and 13, corrected by 0.3, show that the structures lie within the bounds of honeycomb and equi-axed foams (FIG. 19A).

$$\frac{\varepsilon^*}{\varepsilon_s} \propto \left(\frac{\rho^*}{\rho_s}\right) \tag{12}$$

$$\frac{\varepsilon^*}{\varepsilon_s} \propto \left(\frac{\rho^*}{\rho_s}\right)^2 \tag{13}$$

Figure 9A:
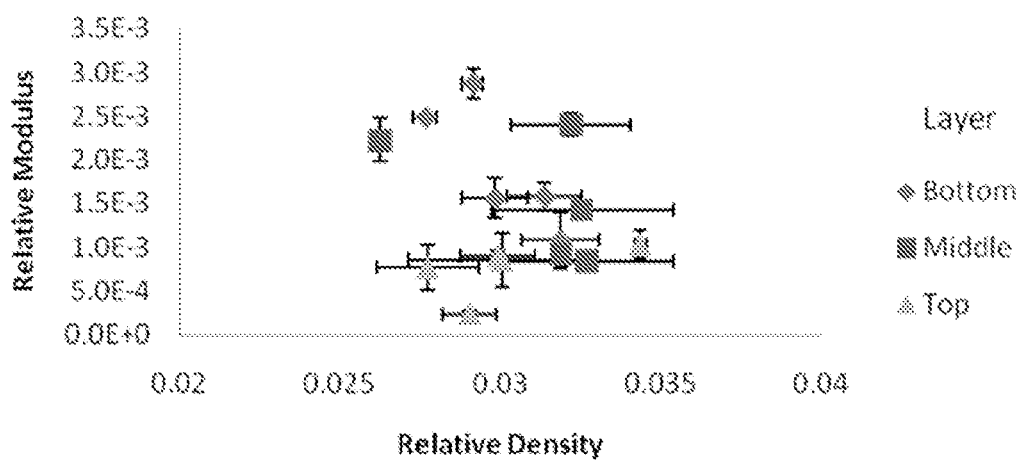
FIG. 9A is a chart of the relative modulus plotted against the relative density in the dry state highlighting the differences of the three layers within the samples.
Figure 9B:
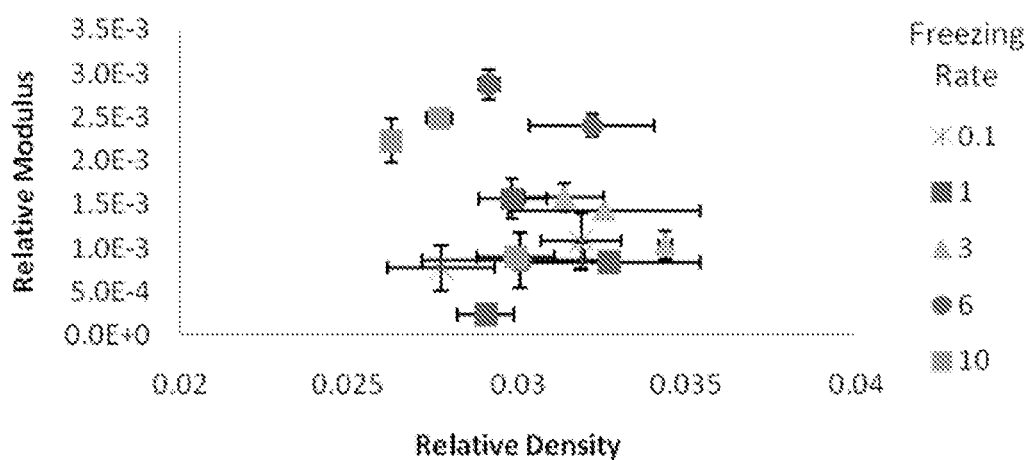
FIG. 9B are the sample values plotted for the different freezing rates.

The data clusters representing those with ridges seen in FIGS. 9A and 9B fall closer to the honeycomb-like slope of 1; this further proves that the ridges act to stiffen the structures, as they are more efficient in deformation.

Lamellae spacing was analyzed and measured using ImageJ software on optical micrographs. Slices were taken at heights equal to those of the thermocouples embedded in the molds; from each slice, 3 images were taken and at least 30 measurements were taken from each image. The resultant plot of lamellae spacing vs. height can be seen in FIG. 12. 19A correlates the spacing to the local cooling rate measured at the same height within the same sample, while 19B correlates the spacing to the freezing front velocity. As explained previously, the relationship between lamellae spacing and freezing front velocity as $$\lambda \propto \frac{1}{V^n},$$

where $\lambda$ is the lamellae spacing, V is the velocity, and the exponent n has been reported to be from 1 to 4 [Butler, 2001, Crystal Growth & Design 1(3): 213-223; Deville, et al., 2007, Acta Materialia 55(6):1965-1974]. FIGS. 13A through 14B show a relatively linear decrease in cooling conditions during the first 15 minutes; this result makes sense as at that point the copper cold finger has reached −80° C. and stops cooling down. Thus when solving for the exponent n, only the freezing front velocities for the first 3 data points were used; from this a value of n=1.67 was obtained. This value is in general agreement with the 1-4 range reported in the literature; however the constant calculated was on the order of $10^{-10}$, whereas Miyawaki et al. reported the slope of the correlation on the order of $10^{-19}$, which is on the order of the self diffusion coefficient of water [Miyawaki, et al., 2004, Food Science and Technology Research 10(4):437-441].

Example 2

Effects of Scaffolds on Neurite Growth

Figures 21A, 21B:
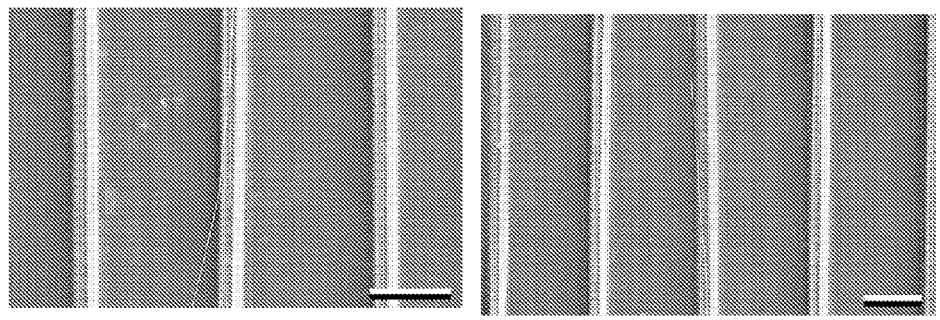
FIGS. 21A and 21B are SEM images showing an extending neurite growing onto (21A) and off of (21B) the same laminin-coated ridge. Scale bar for both is 10 μm.
Figures 22A, 22B:
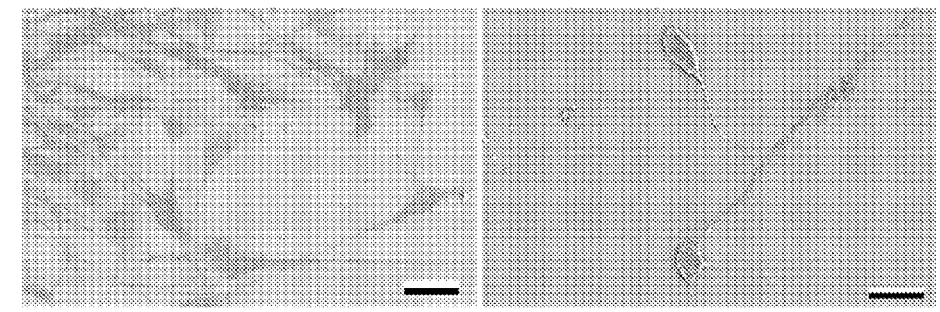
FIGS. 22A and 22B are SEM images showing control neurites cultured on laminin-coated glass coverslides. Scale bar for 22A is 40 μm; scale bar for 22B is 20 μm.

Having elucidated the structure-property correlations within the samples, and showing that the ridges serve to strengthen the elastic buckling-dominated architecture, the next logical step was to determine the ridge's effect on neurite outgrowth. SEM images of dissociated neurons cultured on the scaffolds (FIGS. 20A through 21B) show the soma (FIG. 20B) nestled between two ridges; neurites extended from the soma linearly, and stay within their respective grooves. One or two neurites were seen to jump from groove to groove, but predominately the neurites were guided by the ridges. FIGS. 21A and 21B show the same neurite growing up onto and then off of the same ridge. FIGS. 20A through 21B are in direct contrast to the controls, where both DRGs (FIG. 22A) and dissociated neurons (22B) were cultured on laminin-coated glass coverslides. Neurites were seen to extend in twisting, random directions from the soma; this was further corroborated by subsequent fluorescent microscopy.

The linear alignment of neurites seen in FIG. 23, for example, was further explored using fluorescent microscopy. 24-hour cultures were initially performed, and from FIGS. 24A and 24B, one can see that after 24 hours, partial alignment was achieved, and that the length of the neurites extending from the central bundle was similar to the control. FIG. 24A is a fluorescent image, appearing black and green (the stain). FIG. 24B is an overlaid image of a black-and-white image and a fluorescent image, resulting in a combination of stain (green) and black-and-white, so as to visualize both scaffold, which does not fluoresce, and neurites, which do.

Figures 25A, 25B:
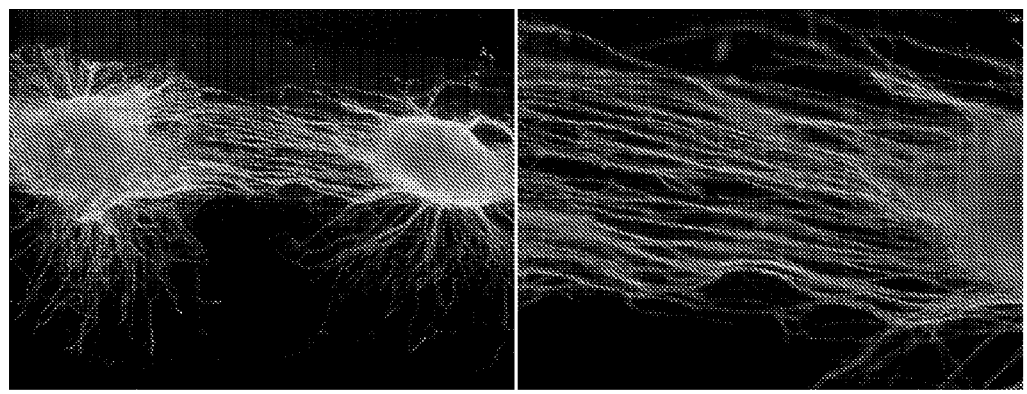
FIGS. 25A and 25B are fluorescent images of DRG cultured for 48 hours on laminin-coated scaffolds.

Forty-eight hour cultures were subsequently undertaken (FIGS. 25A through 27B) and one can clearly see that the DRGs extended neurites along the grooves formed by the ridges. FIG. 25A shows two DRGs, seeded at opposite ends of the isolated lamellae, extending neurites in linearly oriented paths towards each other. The width of the lamellae was approximately the diameter of the DRGs, which is why the neurites extending above and below the DRGs are not aligned; these neurites grew off of the scaffold and served as another version of control.

Figures 26A, 26B:
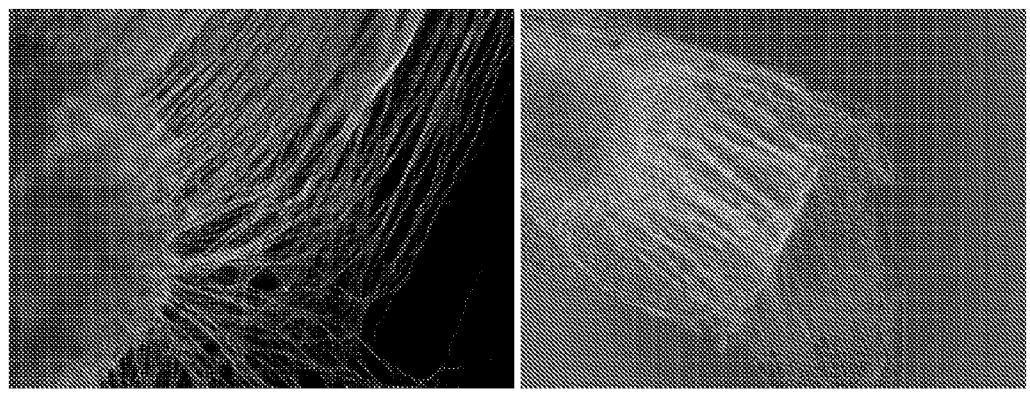
FIG. 26A is a fluorescent image of a DRG cultured for 48 hours.
FIG. 26B is an overlaid fluorescent and black-and-white image showing a DRG cultured for 48 hours on a scaffold with a fold in the middle.

FIG. 26A is that of the DRG bundle extending neurites, which can clearly be seen to curve and align themselves with the ridges and grooves formed within the chitosan scaffold. Growth of axons perpendicular to the ridges was stunted, as can be seen in FIG. 26B through 27B. FIG. 26B is that of a lamellae that became folded prior to culturing; this proved advantageous as the axons can clearly be seen to grow along the grooves, underneath the folded layer of lamellae and terminate at the fold. This is important because the axons did not continue to grow perpendicular to the fold, and reinforces just how well the grooves control the growth of the neurites.

Figures 27A, 27B:
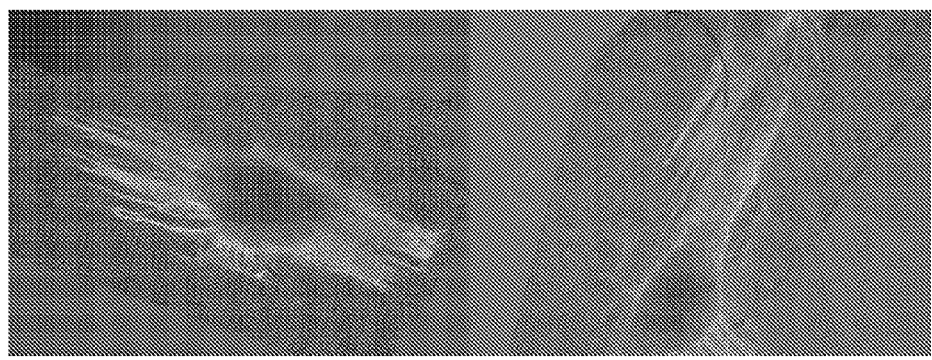
FIGS. 27A and 27B are overlaid fluorescent and black-and-white images of 48 hour DRG cultures showing the DRGs propagating and aligning with the ridges.

Concern was raised that in-vitro, the DRGs may be exuding chemicals or other growth factors that draw far neurites toward it, such would explain the orientation of the bridging neurites seen in FIG. 25A. To prove that the ridges were responsible for such guidance, and not any such factors, two DRGs were seeded opposite a lamellae, as in FIG. 25A, but were offset as can be seen in FIG. 27B. After a 48 hour culture the neurites were seen to grow directly past each other, and stayed aligned to their respective grooves.

Having thus proven that DRGs and dissociated neurites aligned within the grooves, the mechanical properties of the scaffolds within simulated physiological conditions were examined. As explained previously, the samples were soaked in PBS prior to mechanical testing.

Figure 11A:
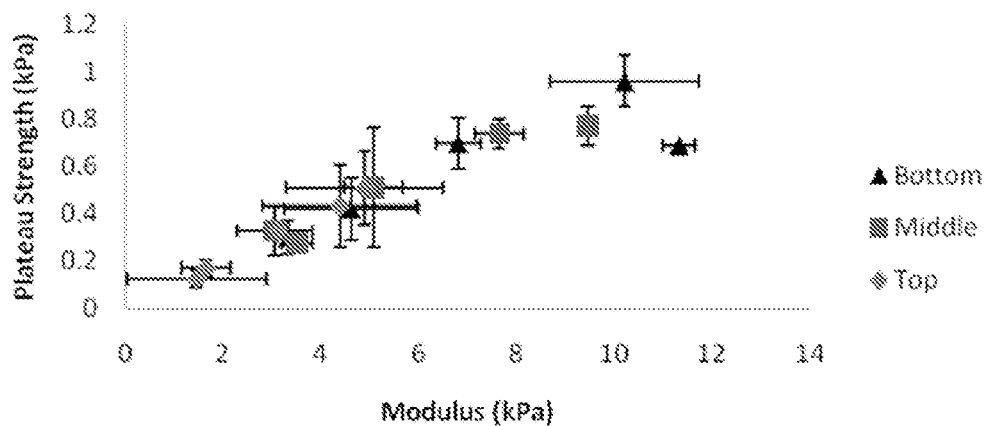
FIG. 11A is a chart of the plateau strength plotted against the modulus in the wet state, highlighting the differences of the three layers within the samples.
Figure 11B:
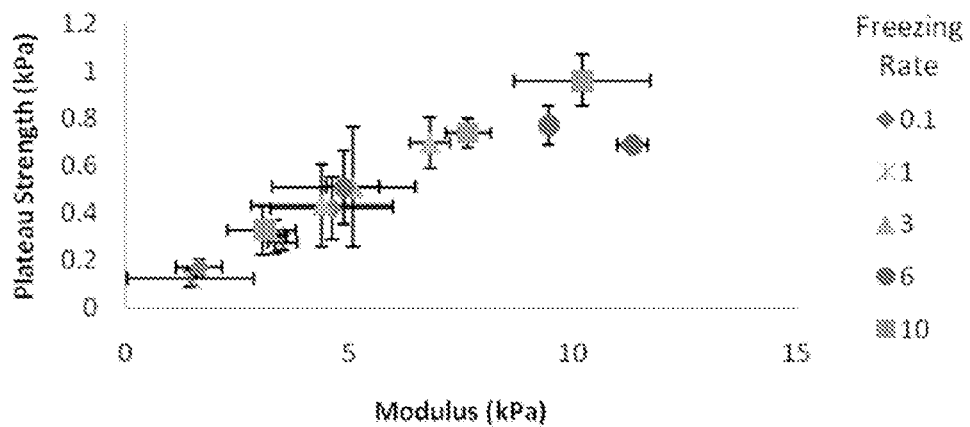
FIG. 11B are the same values plotted for the different freezing rates.
Figure 12:
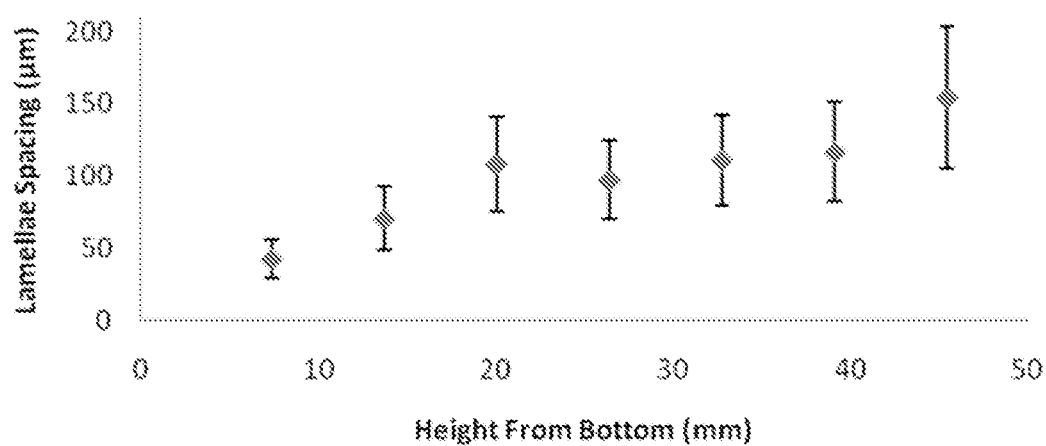
FIG. 12 is a chart illustrating lamellae spacing (mm) vs. height from bottom of sample (mm). Samples were frozen at 6° C./m.
Figure 28:
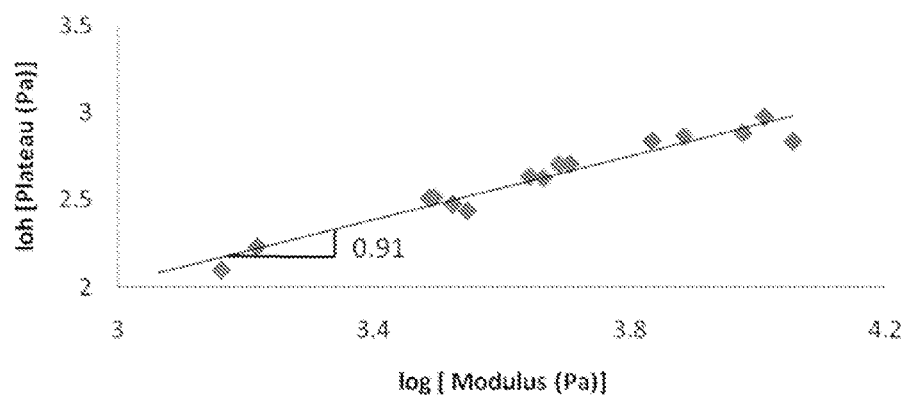
FIG. 28 is a chart of the plateau strength vs. modulus in wet conditions, related as $\sigma_{pl}^* = 0.1 \ (E^*)^{0.91}$.

FIGS. 10A and 10B are those of the modulus and plateau, respectively, versus the various freezing rates in PBS. As with the same samples in dry conditions, one sees that the bottom layer generally outperforms the middle and top layer; this again is consistent with the understanding that at the bottom of the sample the freezing front velocity and the local cool rates are both higher, which lead to smaller lamellae and stronger, stiffer scaffolds. The neutralization of the charges and subsequent soaking in PBS was seen to lower the average chitosan scaffold's modulus and plateau from 721±143 kPa and 45.4±5.6 kPa to 5.36±0.76 kPa and 0.48±0.09 kPa, respectively. The decrease from dry to wet for both modulus and plateau strength was slightly over two orders of magnitude. FIGS. 11A and 12, those of the strength vs. modulus in the wet state, show a similarly higher modulus and plateau for the bottom two layers of 6° C./m and 10° C./m, and when replotting the logs of each one sees that the relationship scales as $\sigma_{pi}^* = 0.1 (E^*)^{0.91}$, as shown in FIG. 28.

The modulus of the bottom two layers of 6° C./m, those containing ridges and those that the in-vitro analysis was performed on, averaged 10.38±0.18 kPa. This value also represents only one method of treatment post-lyophilization, and it is conceivable that either a shorter or different neutralization procedure not explored in this study could lower the resultant wet modulus.

Figures 29A, 29B:
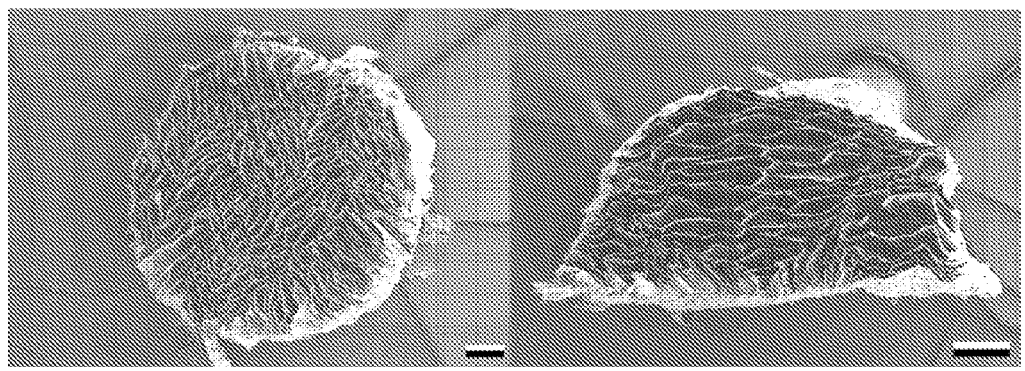
Figure 31:
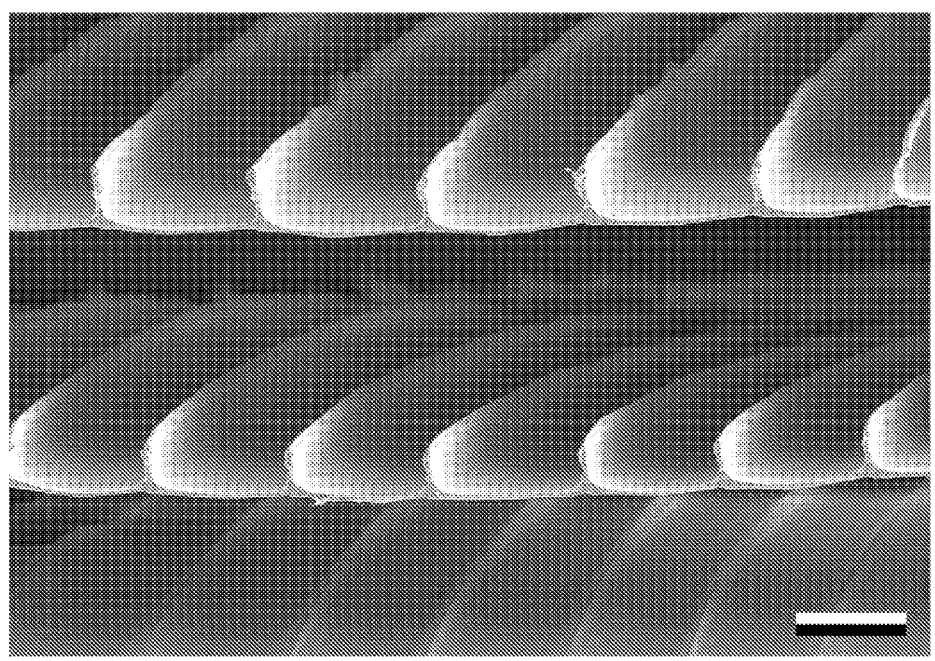
FIG. 31 is a magnified image of FIG. 30A, showing the uniformly distributed ridge formation in small-diameter scaffolds. Scale bar is 15 μm.

The results of the in-vitro analysis, having looked promising, prompted the study of whether or not the scaffolds could be generated on the scale required for in-vivo analysis. Mechanical testing was performed on scaffolds roughly equivalent to that of the human spinal cord. However, in-vivo analysis would begin with rat or comparable spinal cord hemisections, with diameters of approximately 1 mm. To achieve scaffolds of that size, a mold was constructed as detailed previously. Freezing was performed at 6 degrees per minute, although the thermal conditions were different as the size and shape of the mold was different; this difference was visually confirmed as the samples froze in approximately half the time. Nonetheless, as one would expect from the 10° C./m samples, the small scaffolds still created the preferred ridges, and were able to be physically handled, sectioned, and imaged despite their relatively small size. FIGS. 29A and 29B show two of the generated scaffolds, with an outer diameter of approximately 1.5 mm, maintaining their structural rigidity and characteristic ridge-forming lamellae. FIGS. 30A through 31 are magnified SEM images of the small diameter scaffolds demonstrating that the ridges are still present and, as seen in FIG. 31, quite uniformly distributed.

Thus, demonstrated herein the feasibility of freeze casting, a relatively novel processing approach to biomaterials, with regard to neuronal scaffolds. Chitosan, a polysaccharide, is a partially deacetylated derivative of chitin and is cationic nature, which allows for future modifications with glycosaminoglycans, and has relatively easy processing requirements. Freeze-cast chitosan structures have been created across a range of processing conditions and sample sizes, and the structure-property correlations have been elucidated, with particular emphasis on the local conditions required for ridge formation to occur in the solidifying structure, and how these ridges serve to strengthen the elastically-dominated deformation in both dry and wet condition. Individual lamellae were physically isolated and in-vitro analysis was performed by culturing DRGs. The results of these tests show neurites aligning with the ridges and propagating down the channels. This, coupled with the observations that neurite growth perpendicular to the ridges was stunted, leads to these structures as neuronal-guiding scaffolds for spinal cord injury reparation and other such conditions. Mechanical values of scaffolds soaked in PBS are within a few kPa of host tissues, and can be further modified by different neutralization methods.

Example 3

Chitosan-Alginate and Alginate Scaffolds

In preparation of a chitosan-alginate scaffold, a chitosan-alginate polyelectrolyte complex (PEC) mixture is prepared by sonicating or homogenizing on ice a in a range of 1:1 to 1:9 solutions (both ways) of chitosan (prepared in 1% acetic acid) and alginate (prepared in water), total polymer content ranging from 0.5%-5%. The pH of the resulting mixture is adjusted with NaOH up to approximately 10.0. The chitosan-alginate PEC mixture is freeze cast (directionally frozen) at a constant cooling rate (0.1°/min-10°/min) until solid and lyophilized until dry. Dried scaffolds are crosslinked in 0.1-2.5% calcium chloride for 5-30 minutes and washed in phosphate buffered saline (PBS) prior to any further use of the scaffold. For cell attachment, scaffolds can be coated in polylysine or polyornithine (0.5 mg/ml for 6 minutes) followed by coating in laminin (10 μg/ml-250 μg/ml for 30 mins-24 hours). Mechanical testing of the scaffolds was performed in compression at a strain rate of 0.01/second in phosphate buffered saline. In vitro analysis was performed by seeding embryonic day 10 chick dorsal root ganglia (DRGs) on laminin-coated scaffolds. After 7 days in culture, the DRG-seeded scaffolds were fixed and processed for immunocytochemistry using mouse monoclonal anti-neurofilament 200 kDa and AlexaFluor 488 and analyzed with confocal microscopy.

Figure 32:
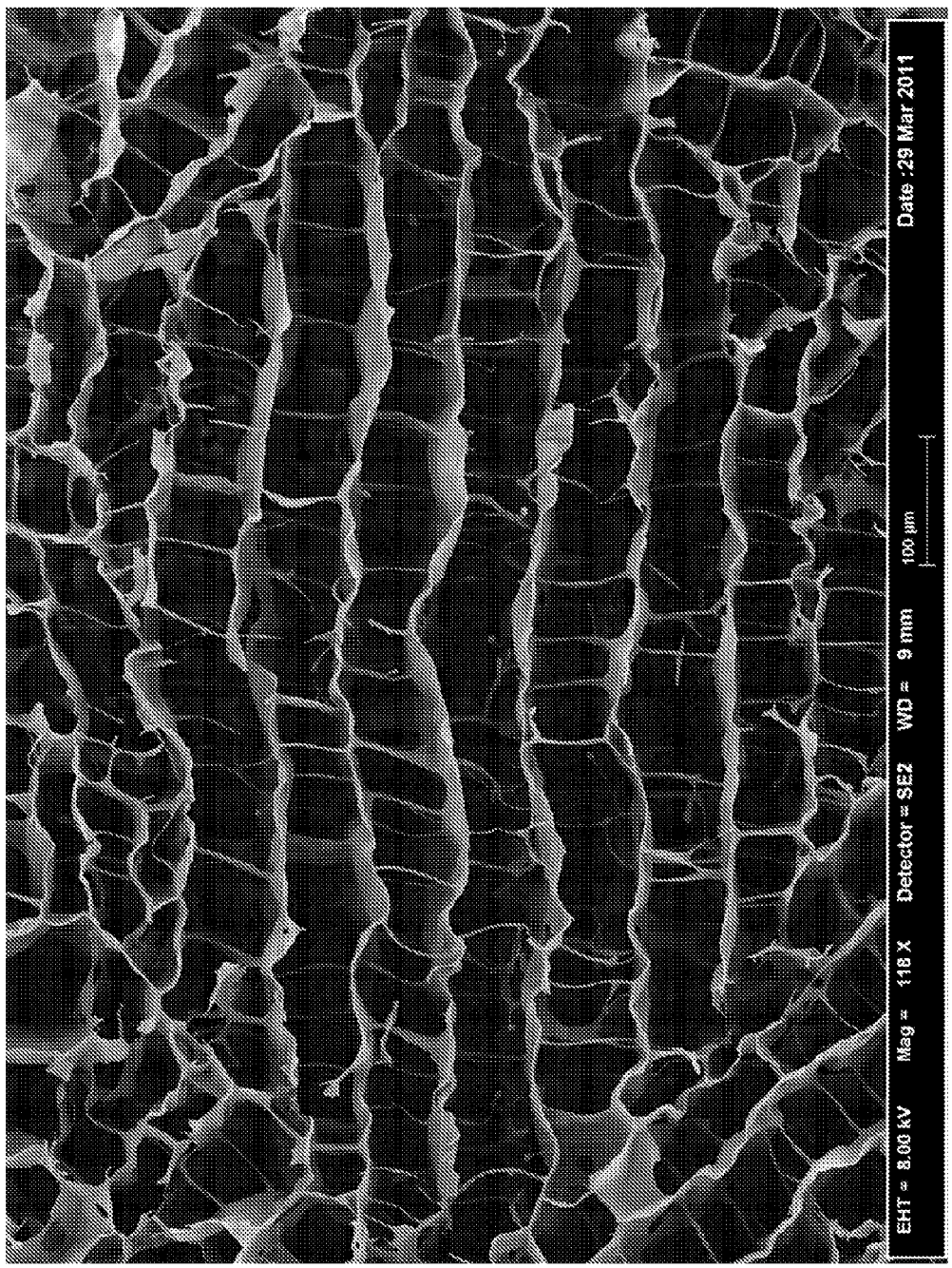
FIG. 32 is a scanning electron microscope image of a cross-section of a chitosan-alginate scaffold.

The aforementioned process produced a linearly aligned porous chitosan-alginate scaffold with a Young's modulus of 5.08+/−0.61 kPa, comparable to reported values of 3-5 kPa for native spinal cord tissue. Scanning electron microscopy analysis indicated suitable channel width, with the channels extending longitudinally throughout the scaffold. The resulting scaffold can be seen in FIG. 32. It was also shown that DRG explants adhered to the scaffold and extended neurites through the scaffold in parallel alignment with the channel direction. Coating the scaffold with poly-L-ornithine and laminin promoted significantly more neurite growth than uncoated scaffold ($p<0.001$). This suggests that such chitosan-alginate scaffolds are a promising candidate for use as a neural tissue engineering scaffold, due to their ability to support DRG attachment and promote the directionally oriented growth of DRG neurites.

In preparation of an alginate scaffold, an alginate/calcium carbonate/glucono-delta-lactone mixture is prepared by stirring, with concentrations ranging from 0.5-5 wt. % alginate, 0.5-15 g/L calcium carbonate, and 1-50 g/L glucono-delta-lactone in a volume ratio of 2:1:1 (alginate:$CaCO_3$:GDL) as a "pre-gelling" process. The resulting mixture is freeze cast (directionally frozen) at a constant cooling rate (0.1°/min-10°/min) until solid and lyophilized until dry. The dried scaffolds are crosslinked in 0.1-2.5 wt. % calcium chloride for 5-30 minutes and washed in HEPES buffered saline prior to any further use of the scaffold. For cell attachment, scaffolds can be coated in polylysine or polyornithine (0.1-1.0 mg/ml for 3-10 minutes) followed by coating in laminin (10 μg/ml-250 μg/ml for 30 mins-24 hours). This resulted in the unexpected finding that without the partial pre-gelling by addition of $CaCO_3$:GDL, the scaffolds could not be cross linked with $CaCl_2$ after freeze drying without adequately maintaining the structure of the scaffold.

Example 4

Fabrication of Microcapsules Containing Bioactive Compounds and/or Stabilizers

In the preparation of alginate microcapsules, a Buchi-190 Mini Spray Dryer is used, and 1-2% alginate is spray dried and collected in a dry container or collected in 1%-3% calcium chloride. For ionic crosslinking, microcapsules collected in calcium chloride are washed in water and further coated in: A) 0.1-1% chitosan solution (prepared in 1% acetic acid) for 5-20 minutes, B) the solution of (A) followed by 0.1-1% alginate solution for 5-20 minutes; and/or C) the solution of (A) followed by 0.1-1% polyethylene glycol solution for 5-20 minutes. The additional crosslinking/coating steps are followed by washing in water, freezing, and lyophilizing until dry.

For covalent crosslinking, alginate microcapsules (collected dry or collected in calcium chloride) are suspended in ethanol. Epichlorohydrin (1-25% v/v) is added to the microcapsule mixture in ethanol. The mixture is sonicated or homogenized on ice while adding 1M-6M sodium hydroxide. The mixture is stirred at room temperature for 6-24 hours and the reaction is then stopped by adjusting the pH to 7 with 1M hydrochloric acid. The crosslinked microcapsules are washed in ethanol in decreasing concentrations (e.g., 75%, 50%, 25%), followed by washing in water three times. Alternate covalent crosslinking is performed by suspending the alginate microcapsules in methanol containing 1-25% glutaraldehyde and 0.05-5% hydrochloric acid, stirring for 0-48 hours. Remaining calcium chloride is removed by stirring microcapsules in 55 mM sodium citrate for 10 minutes, followed by washing in water. Microcapsules can also be coated here in A) 0.1-1% chitosan solution (prepared in 1% acetic acid) for 5-20 minutes, B) the solution of (A) followed by 0.1-1% alginate solution for 5-20 minutes; and/or C) the solution of (A) followed by 0.1-1% polyethylene glycol solution for 5-20 minutes. The additional crosslinking/coating steps are followed by washing in water, freezing, and lyophilizing until dry.

In the preparation of chitosan microcapsules, a Buchi-190 Mini Spray Dryer can be used, and 1-2% chitosan is spray dried and collected in a dry container. Chitosan microcapsules are stirred in 0.4% sodium hydroxide in ethanol solution for 15 mins to 1 hr before washing in PBS. The microcapsules can be coated in 0.1-1% alginate solution for 5-20 minutes before washing in water, freezing, and lyophilization until dry. For covalent crosslinking, the microcapsules are stirred in a 0.001%-1% genipin solution prepared in PBS, or 0.001-25% glutaraldehyde solution for 0-48 hours. Crosslinking is stopped by stirring the microcapsules in a 10% glycine (prepared in PBS) solution for 30 minutes. The microcapsules can also be coated in 0.1-1% alginate solution for 5-20 minutes, or alginate solution followed by 0.1-1% polyethylene glycol solution for 5-20 minutes before washing in water, freezing, and lyophilizing until dry.

To load protein, growth factors, enzymes or other components into the microcapsules, the microcapsules are soaked (either from a dry state or pre-hydrated in PBS) in the desired protein solution (with or without stabilizers such as trehalose) with concentrations ranging from 1 μg/ml to 1 g/ml for 15 mins to 24 hours before rinsing with PBS.

To incorporate the microcapsules into scaffolds, the protein-loaded alginate or chitosan microcapsules are stirred into the polyether mixture prior to freeze casting (directional freezing) for spatial localization of growth factors or enzymes within the scaffold. Microcapsule-loaded scaffolds are prepared as described above.

To spatially locate the bioactive microcapsules, the freeze casting is performed in stages, adding polymer/bioactive mixtures at points where the bioactive agent is required, for example enzyme would be most valuable at the ends of the scaffold where it could act on the glial scar in the spinal cord, and growth factors should be located so that a gradient of released factor could be developed which attracts neuronal growth along the gradient towards higher concentrations.

Example 5

Alginate-Based Scaffolds

Figure 34:
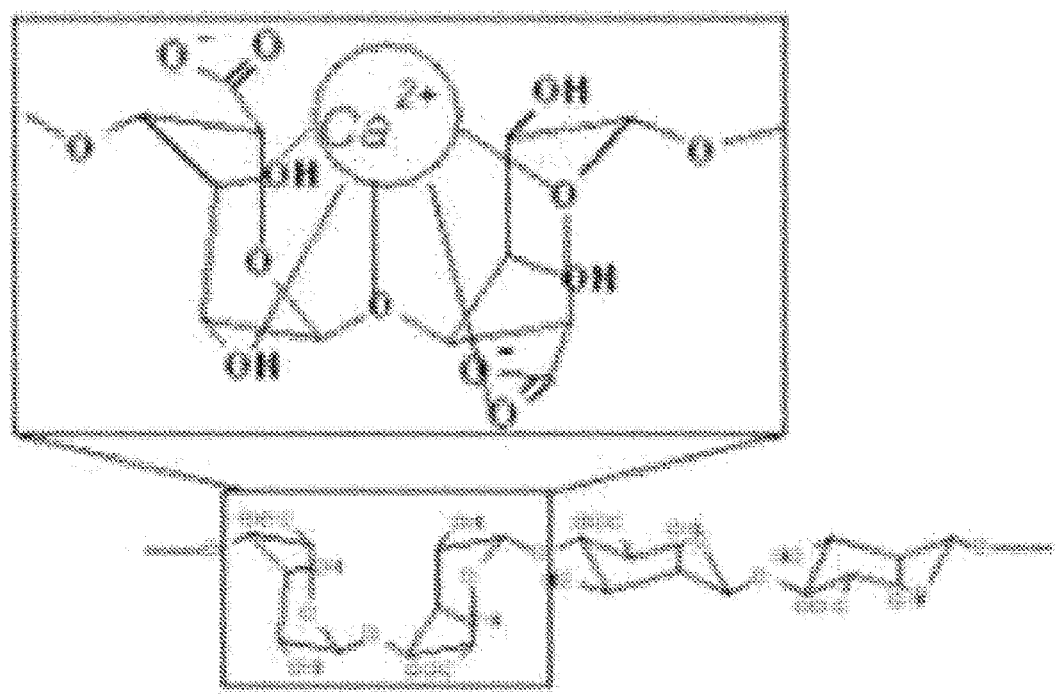
FIG. 34 is a schematic depicting the structure of alginate and how it reacts to the addition of calcium.

A weight by volume (w/v) alginate solution in DI water was prepared and filtered with a 0.45 micrometer bottle filter to remove any particles and then frozen to −80° C. The frozen sample was lyophilized in a 4.5 Liter Benchtop Freeze Dry System (Labconco, Kansas City, Mo.). The filtered lyophilized alginate is reconstituted into solutions of various concentrations (0.1%-5%) with water or buffer. Three methods of crosslinking were tested with two different crosslinkers, calcium chloride and calcium carbonate. The calcium carbonate is a slow crosslinker, samples could take several hours up to days to fully crosslink, and so to control and increase the speed of the react ion glucono delta lactone (GDL) is added. The GDL hydrolyses and enables the $Ca^{2+}$ ions to get free of the carbonate and crosslink the alginate as depicted in FIG. 34.

Because calcium chloride is a fast crosslinker, the samples will fully gel in a few minutes. In one method, the addition of $CaCl_2$ to the alginate solution was made prior to freezing; it was allowed to fully gel before being placed on the freeze caster. Other methods used a 5.5% (w/v) solution of calcium carbonate+GDL added to the alginate solution prior to initial freezing. The full crosslinking process lasted approximately 90 minutes. A series of samples was made having been fully crosslinked, referred to later as gel phase or (gelled). In other instances, samples were put on the freeze caster immediately following the addition of the calcium carbonate+GDL to the alginate solution, referred to later as (L) phase.

The alginate solution was poured into a polytetrafluoroethylene (PTFE) tube that was sealed at the bottom with a copper plug. PTFE was used as the mold material because it allows easy removal of the sample following freezing. Copper was chosen as the plug material because it has the same thermal conductivity as the copper cold fingers of the freeze caster. Petroleum jelly was applied around the rim of the plug to ensure a tight seal. The PTFE tubes have an outer diameter of 25 mm, a wall thickness of 7 mm, and a height of 50 mm.

The alginate solution was degassed in a speed mixer and poured slowly into the tubes to prevent bubbles from forming. Bubbles can affect the structure of the sample by forming voids and weakening it. The full tube was placed on the copper cold finger and taped in place with black electrical tape. The cooling rates tested were 10° C./min, 6° C./min and 1° C./min. The samples were freeze cast starting at 5° C. and going to −150° C. They were held at −150° C. on the cold finger until completely frozen. The formation of ice crystals on the surface of the sample was the visual confirmation the sample was fully frozen.

The results of the experiments are now described.

Figure 35:
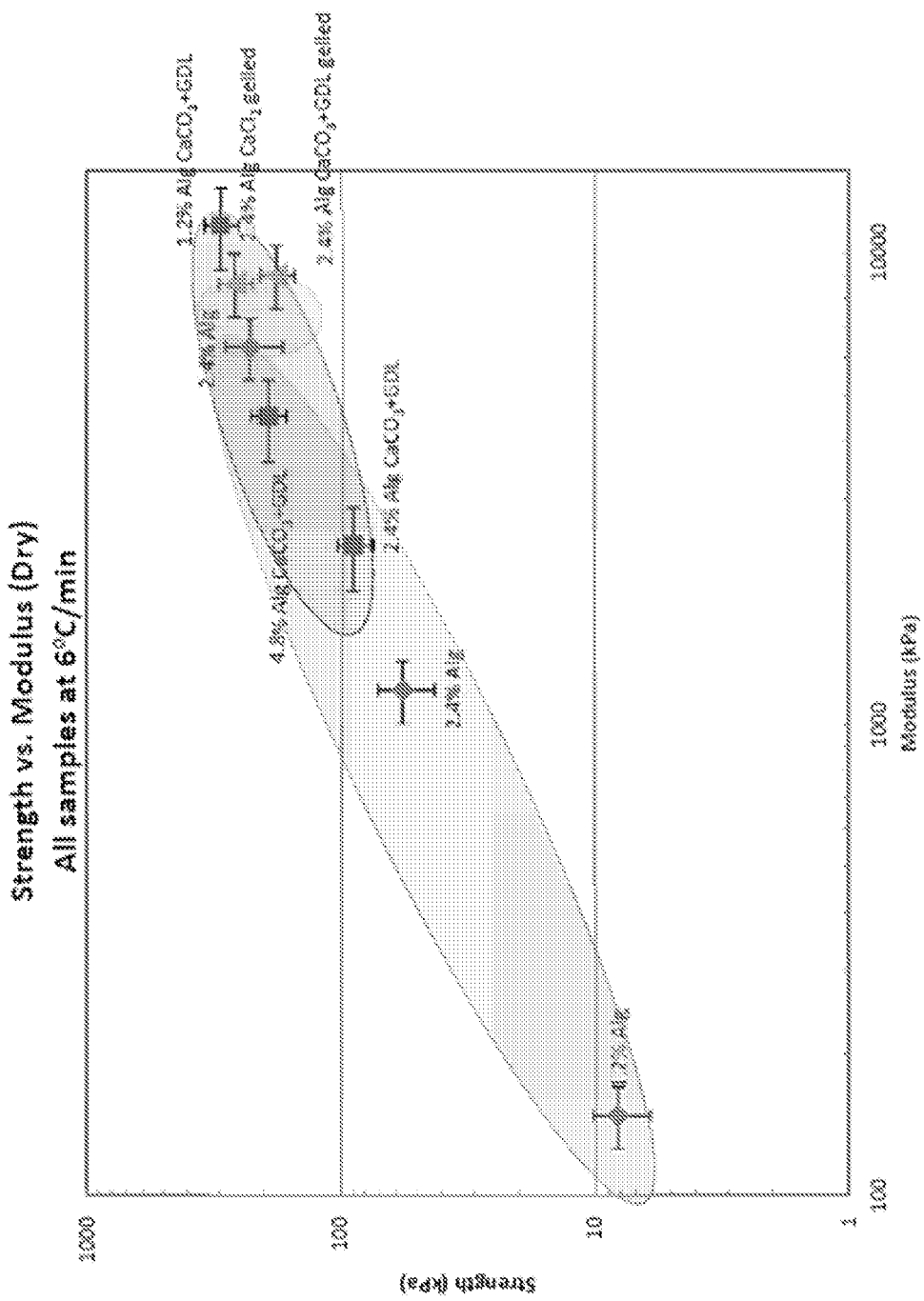
FIG. 35 is a chart of yield strength vs. Young's Modulus in the dry state.
Figure 36:
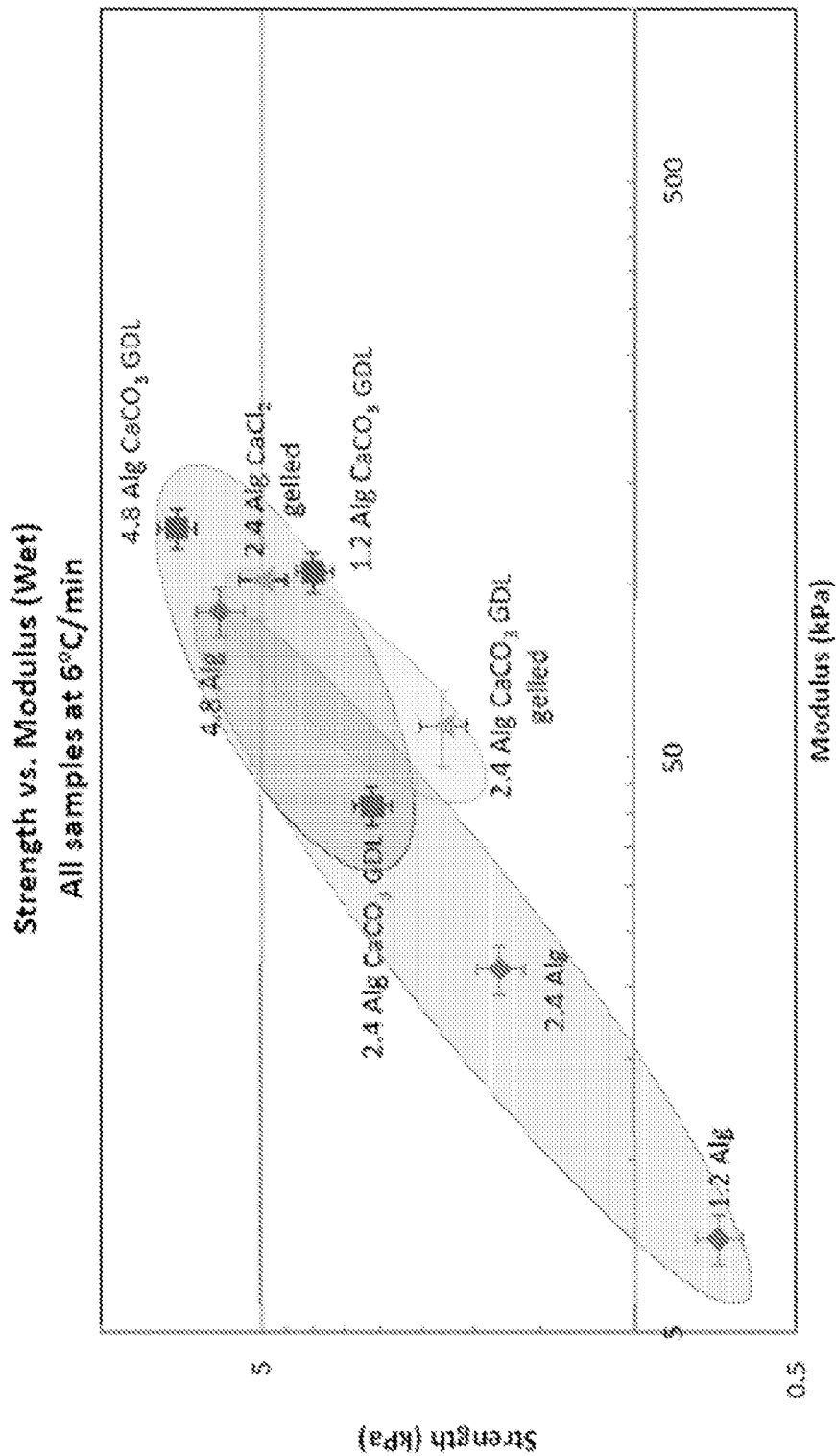
FIG. 36 is a chart of yield strength vs. Young's Modulus in the wet state.

FIG. 35 and FIG. 36 show that as the polymer concentration is increased from 1.2% to 2.4% to 4.8%, there is an increase in the mechanical properties; note the diamond data points. As the degree of crosslinking is increased the mechanical properties also increase; note the square and triangle data point markers. Those samples marked by the squares had the crosslinker added and were immediately put onto the freeze caster and crosslinked during the freezing process. The triangle data points are that of samples which were allowed to fully crosslink and gel before being put onto the freeze caster. The amount of crosslinker added was held constant for all samples, and is thought to be the reason for the one outlying square data point of 1.2% alginate $CaCO_3$+GDL. Because of high ratio of crosslinker to polymer in those samples, it is believed those samples fully crosslinked and gelled giving them higher mechanical property values. Fully gelled samples also showed a lower pore aspect ratio than the rest and this was observed in the 1.2% alginate $CaCO_3$+GDL samples, see Aspect ratio in Table 2.

TABLE 2

Structure properties

| Composition | Cooling Rate (° C./min) | Pore Length (μm) | Pore width (μm) | Aspect ratio | Wall thickness (μm) | Ridge Height (μm) | Ridge Spacing (μm) |
|---|---|---|---|---|---|---|---|
| 1.2% Alginate | 1 | 550 | 100 | 5.5 | 0.15 ± 0.05 | 10 ± 4 | 30 ± 8 |
|  | 6 | 370 | 65 | 5.7 | 0.13 ± 0.03 | 8 ± 3 | 26 ± 5 |
|  | 10 | 320 | 80 | 4.0 | 0.10 ± 0.04 | 6 ± 2 | 23 ± 4 |
| 2.4% Alginate | 1 | 400 | 80 | 5.0 | 0.25 ± 0.03 | 11 ± 3 | 29 ± 6 |
|  | 6 | 345 | 70 | 4.9 | 0.23 ± 0.04 | 10 ± 3 | 25 ± 4 |
|  | 10 | 300 | 70 | 4.3 | 0.22 ± 0.02 | 10 ± 4 | 22 ± 5 |
| 4.8% Alginate | 1 | 400 | 90 | 4.4 | 0.32 ± 0.04 | 12 ± 5 | 30 ± 4 |
|  | 6 | 330 | 65 | 5.1 | 0.29 ± 0.05 | 10 ± 4 | 23 ± 4 |
|  | 10 | 300 | 70 | 4.3 | 0.27 ± 0.02 | 10 ± 6 | 20 ± 5 |
| 1.2% Alginate + $CaCO_3$ + GDL | 1 | 70 | 40 | 1.8 | 0.12 ± 0.03 | N/A | N/A |
|  | 6 | 60 | 35 | 1.7 | 0.10 ± 0.02 | N/A | N/A |
|  | 10 | 55 | 39 | 1.4 | 0.09 ± 0.03 | N/A | N/A |
| 2.4% Alginate + $CaCO_3$ + GDL | 1 | 420 | 90 | 4.7 | 0.24 ± 0.05 | 9 ± 4 | 30 ± 5 |
|  | 6 | 350 | 65 | 5.4 | 0.22 ± 0.03 | 10 ± 3 | 24 ± 4 |
|  | 10 | 280 | 60 | 4.7 | 0.21 ± 0.04 | 10 ± 5 | 21 ± 6 |
| 4.8% Alginate + $CaCO_3$ + GDL | 1 | 300 | 60 | 5.0 | 0.35 ± 0.05 | 11 ± 4 | 31 ± 6 |
|  | 6 | 210 | 34 | 6.2 | 0.32 ± 0.03 | 10 ± 4 | 19 ± 5 |
|  | 10 | 240 | 55 | 4.4 | 0.29 ± 0.02 | 10 ± 3 | 18 ± 7 |
| 2.4% Alginate + 8 mMol $CaCl_2$ (gelled) | 6 | 120 | 40 | 3.0 | 0.23 ± 0.04 | 0.6 ± 0.2 | 15 ± 5 |
| 2.4% Alginate + $CaCO_3$ + GDL (gelled) | 6 | 140 | 80 | 1.8 | 0.21 ± 0.05 | N/A | N/A |

Figure 37:
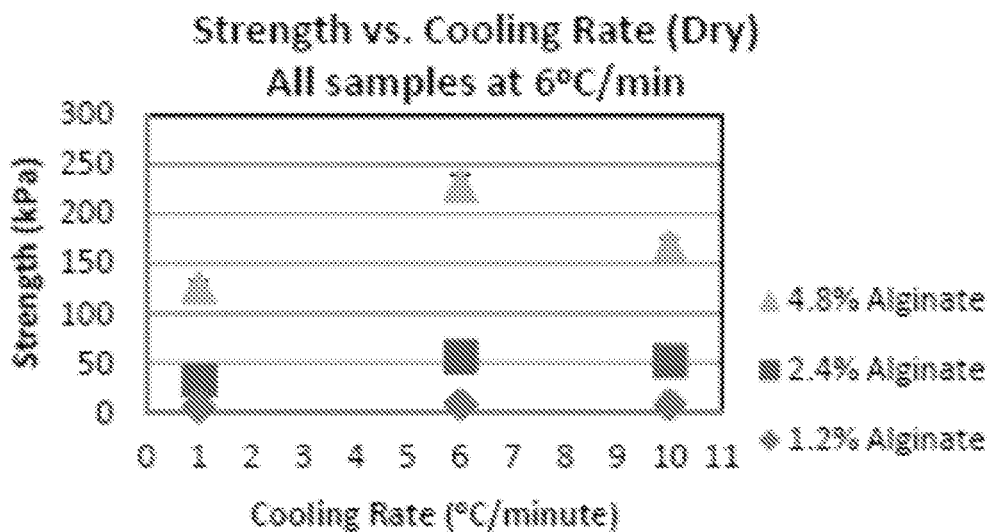
FIG. 37 is a chart of yield strength vs. cooling Rate in the dry state.
Figure 38:
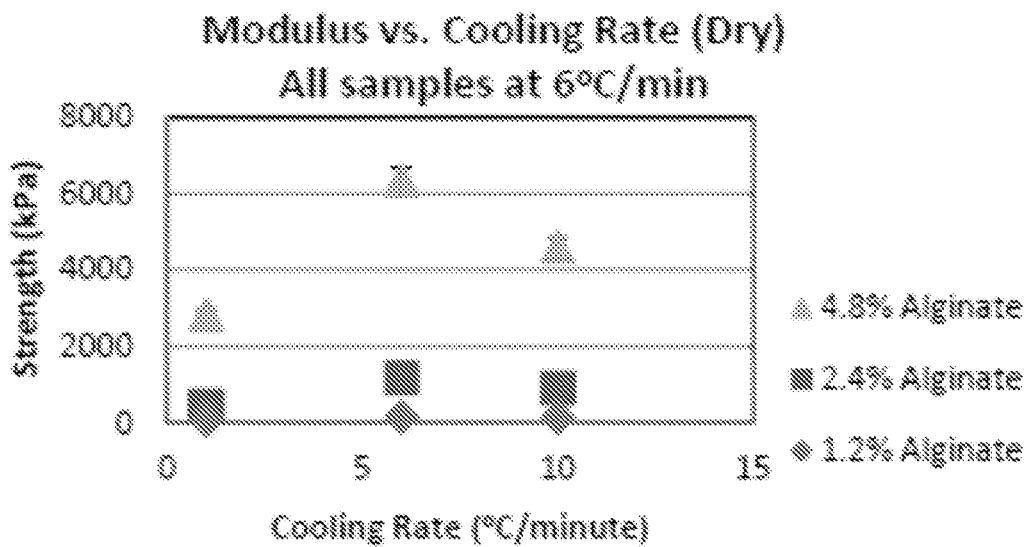
FIG. 38 is a chart of Young's Modulus vs. cooling Rate in the dry state.

As seen in FIG. 37 and FIG. 38 there is an increase in mechanical properties as cooling rate increase from 1° C./min to 6° C./min. As the cooling rate is increased from 6° C./min to 10° C./min, there is a slight drop in properties. This is due to the faster formation of the ice crystals during the freezing process, allowing less time for the polymer to get oriented, thereby making a less stable structure. A cooling rate of 6° C./min was shown to produce the highest mechanical properties in all plain alginate samples, but for crosslinked samples there was an increase of properties with an increase in cooling rate from 1° C./min to 6° C./min to 10° C./min degrees per minute, see Tables 3 and 4.

TABLE 3

Dry Mechanical properties.

| DRY Composition | Cooling Rate (° C./min) | Density (g/cm3) | Parallel to lamellae | | Perpendicular to lamellae | |
|---|---|---|---|---|---|---|
| | | | Young's Modulus [kPa] | Yield Strength [kPa] | Voting's Modulus [kPa] | Yield Strength [kPa] |
| 1.2% Alginate | 1 | 0.012 ± 0.003 | 75.1 ± 17.5 | 5.5 ± 1.8 | 2.6 ± 0.4 | 0.5 ± 0.1 |
| | 6 | 0.022 ± 0.001 | 148.3 ± 43.2 | 8.2 ± 3.4 | 9.8 ± 3.5 | 1.2 ± 0.4 |
| | 10 | 0.022 ± 0.002 | 128.8 ± 20 | 7.9 ± 2.5 | 8.0 ± 2.1 | 1.0 ± 0.3 |
| 2.4% Alginate | 1 | 0.047 ± 0.001 | 430.0 ± 118.3 | 31.8 ± 4.9 | 18.3 ± 9.4 | 1.3 ± 0.3 |
| | 6 | 0.049 ± 0.004 | 1185.8 ± 342.0 | 56.7 ± 4.4 | 28.4 ± 18.2 | 2.1 ± 1.2 |
| | 10 | 0.048 ± 0.001 | 902.7 ± 232.9 | 52.0 ± 6.3 | 40.2 ± 17.6 | 3.5 ± 1.5 |
| 4.8% Alginate | 1 | 0.066 ± 0.001 | 2831.17 ± 289.2 | 126.7 ± 4.1 | 15.2 ± 7.2 | 3.1 ± 1.7 |
| | 6 | 0.072 ± 0.002 | 6359.3 ± 946.8 | 228.3 ± 21.4 | 61.2 ± 4.6 | 4.8 ± 0.3 |
| | 10 | 0.070 ± 0.002 | 4611.2 ± 680.3 | 167.5 ± 8.2 | 28.9 ± 15.6 | 4.1 ± 1.3 |
| 1.2% Alginate + 5.55% CaCO$_3$ + 28GDL (L) | 1 | 0.022 ± 0.002 | 6771 ± 1505.2 | 171.7 ± 35.2 | 1247.7 ± 808.2 | 49.3 ± 23.3 |
| | 6 | 0.030 ± 0.005 | 11480.3 ± 2341.4 | 296.7 ± 48.5 | 1011.3 ± 312.0 | 51.7 ± 11.2 |
| | 10 | 0.027 ± 0.004 | 16647.0 ± 6075.2 | 351.0 ± 100.0 | 1237.7 ± 1012.1 | 34.3 ± 24.0 |
| 2.4% Alginate + 5.5% CaCO$_3$ + 2RGDL (L) | 1 | 0.034 ± 0.002 | 3078.7 ± 1500.0 | 116.7 ± 40.0 | 92.3 ± 40.2 | 8.3 ± 2.2 |
| | 6 | 0.041 ± 0.003 | 2408.7 ± 704.2 | 91.2 ± 9.3 | 265.1 ± 12.1 | 18.8 ± 5.2 |
| | 10 | 0.036 ± 0.002 | 3801.3 ± 204.2 | 136. ± 210.3 | 441.0 ± 210.3 | 25.0 ± 12.3 |
| 4.8% Alginate + 5.5% CaCO$_3$ + 28GDL (L) | 1 | N/A | N/A | N/A | N/A | N/A |
| | 6 | 0.071 ± 0.005 | 4500 ± 500 | 195.6 ± 43.2 | 50.9 ± 20.3 | 4.7 ± 2.1 |
| | 10 | 0.065 ± 0.001 | 6206.7 ± 1200 | 258.3 ± 52.1 | 62.1 ± 31.5 | 4.6 ± 2.3 |
| 2.4% Alginate + 8 mMol CaCl$_2$(gelled) | 6 | 0.053 ± 0.002 | 8988.9 ± 1570.2 | 182.2 ± .36.1 | N/A | N/A |
| 2.4% Alginate + 5.5% CaCO$_3$ + 2SGDL (gelled) | 6 | 0.081 ± 0.004 | 8649.4. ± 1312.3 | 261.5 ± 45.9 | N/A | N/A |

| DRY Composition | Relative Density | Relative Modulus (Par) | Relative Strength (Par) | Relative Modulus (Perp) | Relative Strength (Perp) |
|---|---|---|---|---|---|
| 1.2% Alginate | 0.0075 | 0.000131 | 5.69E−05 | 4.54E−06 | 5.18E−06 |
| | 0.01374 | 0.000259 | 8.49E−05 | 1.71E−05 | 1.24E−05 |
| | 0.01374 | 0.000225 | 8.18E−05 | 1.4E−05 | 1.04E−05 |
| 2.4% Alginate | 0.02936 | 0.00075 | 0.000329 | 3.14E−05 | 1.35E−05 |
| | 0.03061 | 0.002068 | 0.000587 | 4.89E−05 | 2.17E−05 |
| | 0.02998 | 0.001574 | 0.000538 | 6.98E−05 | 3.62E−05 |
| 4.8% Alginate | 0.04122 | 0.004941 | 0.001304 | 2.62E−05 | 3.21E−05 |
| | 0.04497 | 0.011161 | 0.00236 | 0.000106 | 4.97E−05 |
| | 0.04372 | 0.008047 | 0.001729 | 5.06E−05 | 4.24E−05 |
| 1.2% Alginate + 5.55% CaCO$_3$ + 28GDL (L) | | | | | |
| 2.4% Alginate + 5.5% CaCO$_3$ + 2RGDL (L) | | | | | |
| 4.8% Alginate + 5.5% CaCO$_3$ + 28GDL (L) | | | | | |
| 2.4% Alginate + 8 mMol CaCl$_2$(gelled) | | | | | |
| 2.4% Alginate + 5.5% CaCO$_3$ + 2SGDL (gelled) | | | | | |

TABLE 4

Wet mechanical properties

| WET Composition (w/v) | Cooling Rate (° C./min) | Parallel to lamellae | |
|---|---|---|---|
| | | Young's Modulus [kPa] | Yield Strength [kPa] |
| 1.2% Alginate | 1 | N/A | N/A |
| | 6 | 7.3 ± 1.4 | 0.7 ± 0.2 |
| | 10 | 3.1 ± 1.5 | 0.2 ± 0.1 |
| 2.4% Alginate | 1 | 15.4 ± 6.1 | 0.7 ± 0.2 |
| | 6 | 21.4 ± 3.5 | 1.8 ± 0.3 |
| | 10 | 13.4 ± 3.5 | 0.7 ± 0.3 |
| 4.8% Alginate | 1 | 72.3 ± 14.1 | 3.9 ± 0.2 |
| | 6 | 89.7 ± 16.5 | 6.0 ± 2.4 |
| | 10 | 96.7 ± 15.4 | 8.3 ± 1.2 |
| 1.2% Alginate + CaCO$_3$ + GDL | 1 | 87.9 ± 7.3 | 3.8 ± 0.3 |
| | 6 | 105.1 ± 5.2 | 4.0 ± 0.2 |
| | 10 | 88.7 ± 20.4 | 3.3 ± 0.7 |

TABLE 4-continued

Wet mechanical properties

| WET Composition (w/v) | Cooling Rate (° C./min) | Parallel to lamellae | |
|---|---|---|---|
| | | Young's Modulus [kPa] | Yield Strength [kPa] |
| 2.4% Alginate + CaCO$_3$ + GDL | 1 | 33.0 ± 8.9 | 1.5 ± 0.7 |
| | 6 | 41.2 ± 7.2 | 3.1 ± 0.3 |
| | 10 | 36.4 ± 7.4 | 2.1 ± 0.3 |
| 4.8% Alginate + CaCO$_3$ + GDL | 1 | N/A | N/A |
| | 6 | 125 ± 10.4 | 7.2 ± 2.3 |
| | 10 | 178.5 ± 15.1 | 9.5 ± 2.5 |
| 2.4% Alginate + 8 mMol CaCl$_2$ (gelled) | 6 | 101.7 ± 7.2 | 5.0 ± 0.8 |
| 2.4% Alginate + CaCO$_3$ + GDL (gelled) | 6 | 56.7 ± 14.1 | 2.3 ± 0.3 |

Figure 39:
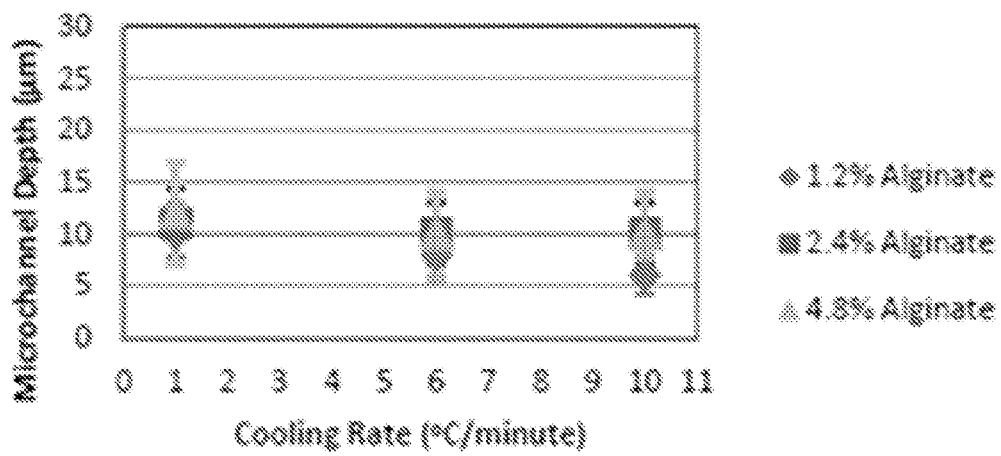
FIG. 39 is a chart of microchannel depth vs. cooling rate.
Figure 40:
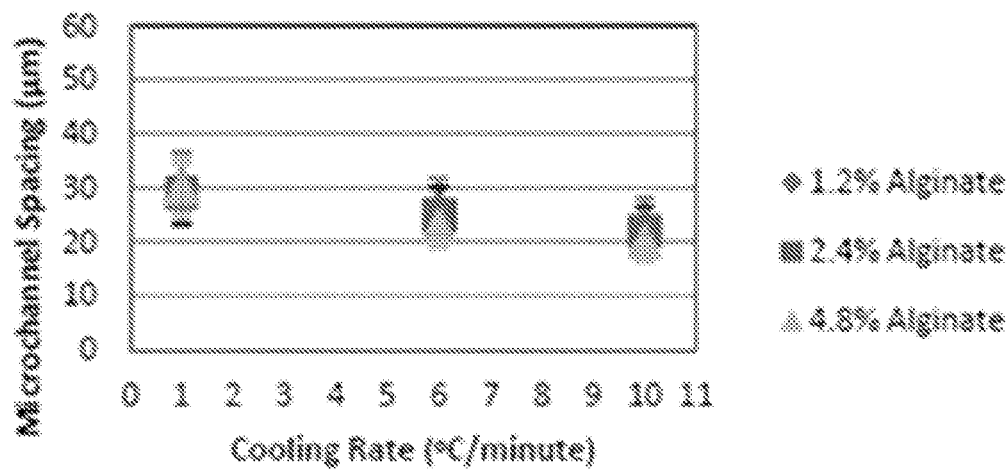
FIG. 40 is a chart of microchannel width vs. cooling rate.
Figure 41:
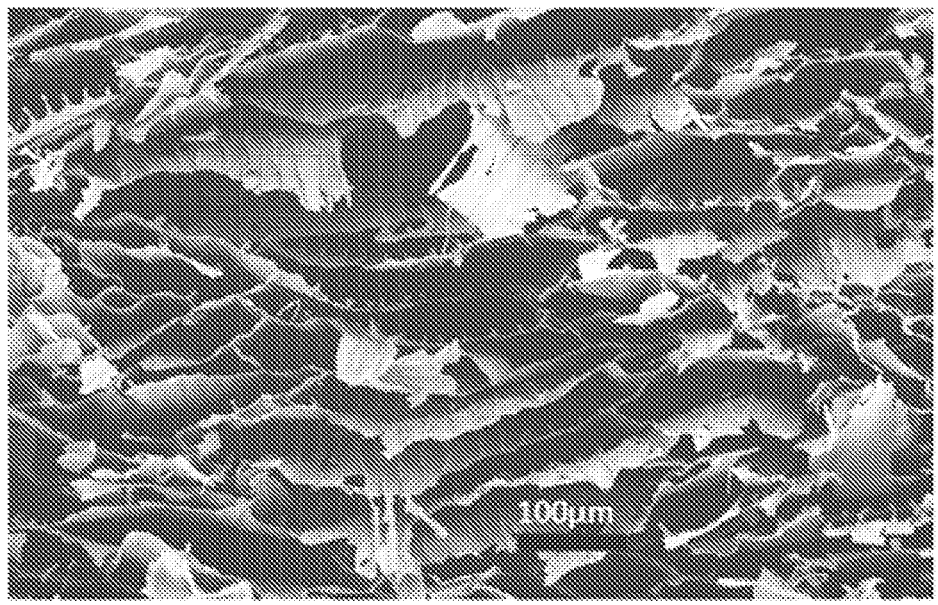
FIG. 41 is a micrograph taken on scanning electron microscope of 1.2% alginate at 6° C./min.
Figure 42:
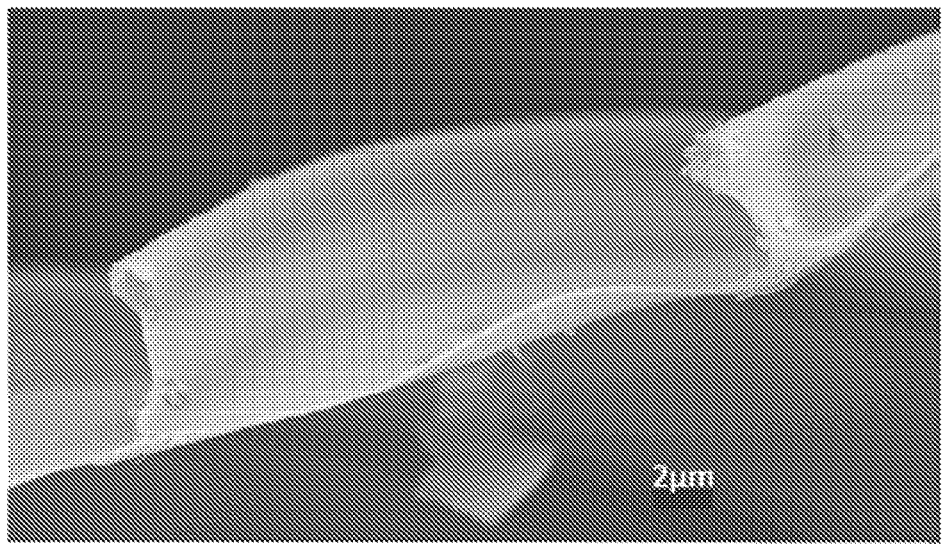
FIG. 42 is a micrograph taken on a scanning electron microscope of ridges from the top layer of a 1.2% alginate sample.

FIG. 39 and FIG. 40 show similar trends related to cooling rate. There is only a slight decrease in microchannel size and depth with the increase in cooling rate. All depths observed in the present experiment were larger than 3 μm, so the channels contain nearly all neuronal growth from cross-channel climbing. As for channel width, the average was slightly above 25 μm, with the range of 10-30 μm. As for ridge formation and structure, channels have been observed in all three layers of all plain alginate samples. Examples of ridges and microchannels can be seen below.

Figure 45:
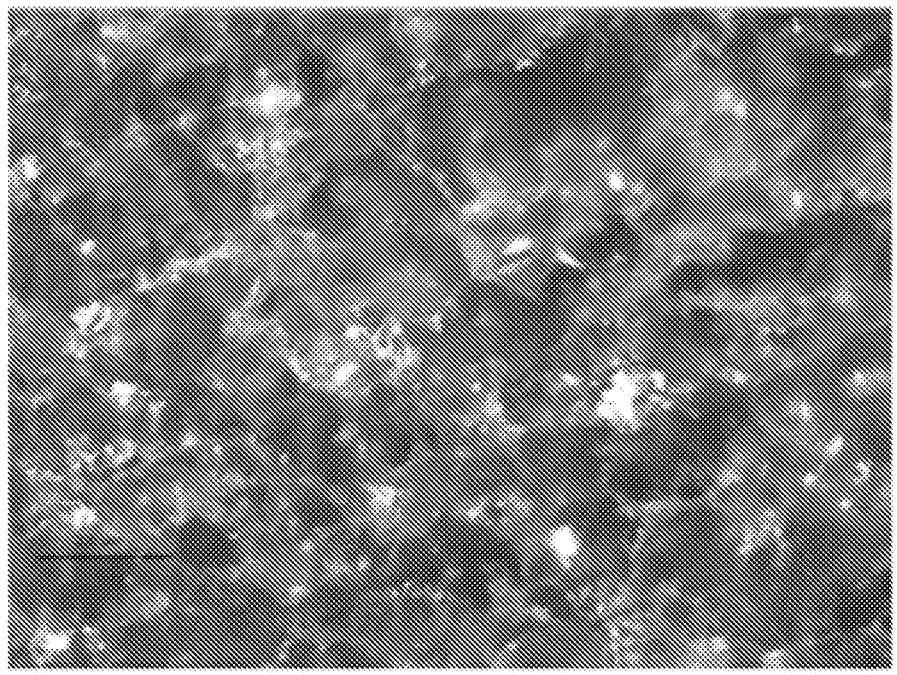
FIG. 45 is a micrograph taken on a Leica optical microscope of the honeycomb like structure of the fully gelled calcium carbonate+GDL sample, scale bar is 200 μm.
Figure 46:
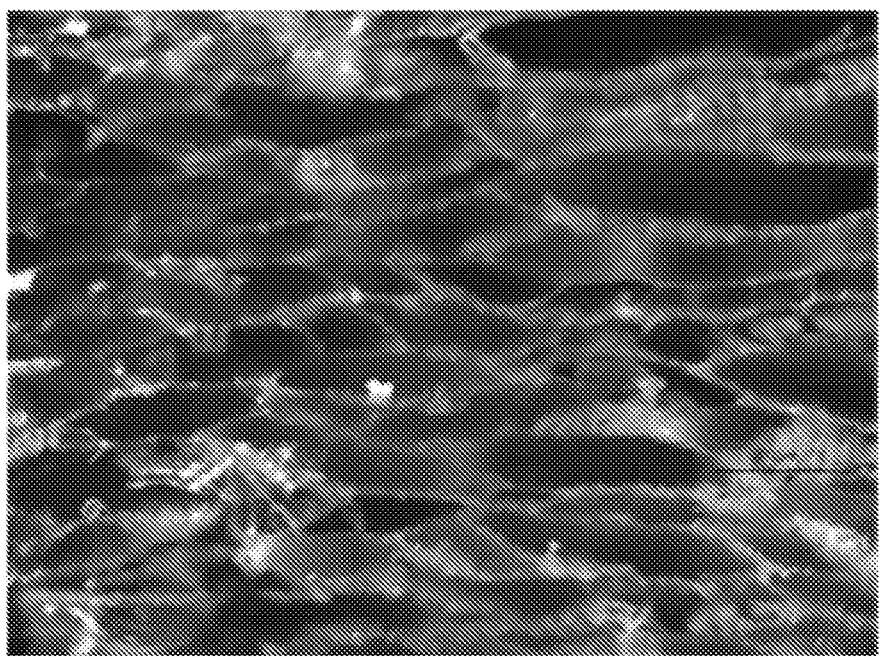
FIG. 46 is a micrograph taken on a Leica optical microscope of elongated pore structure seen in most samples, pictured here is 4.8% alginate, scale bar is 200 μm
Figure 47:
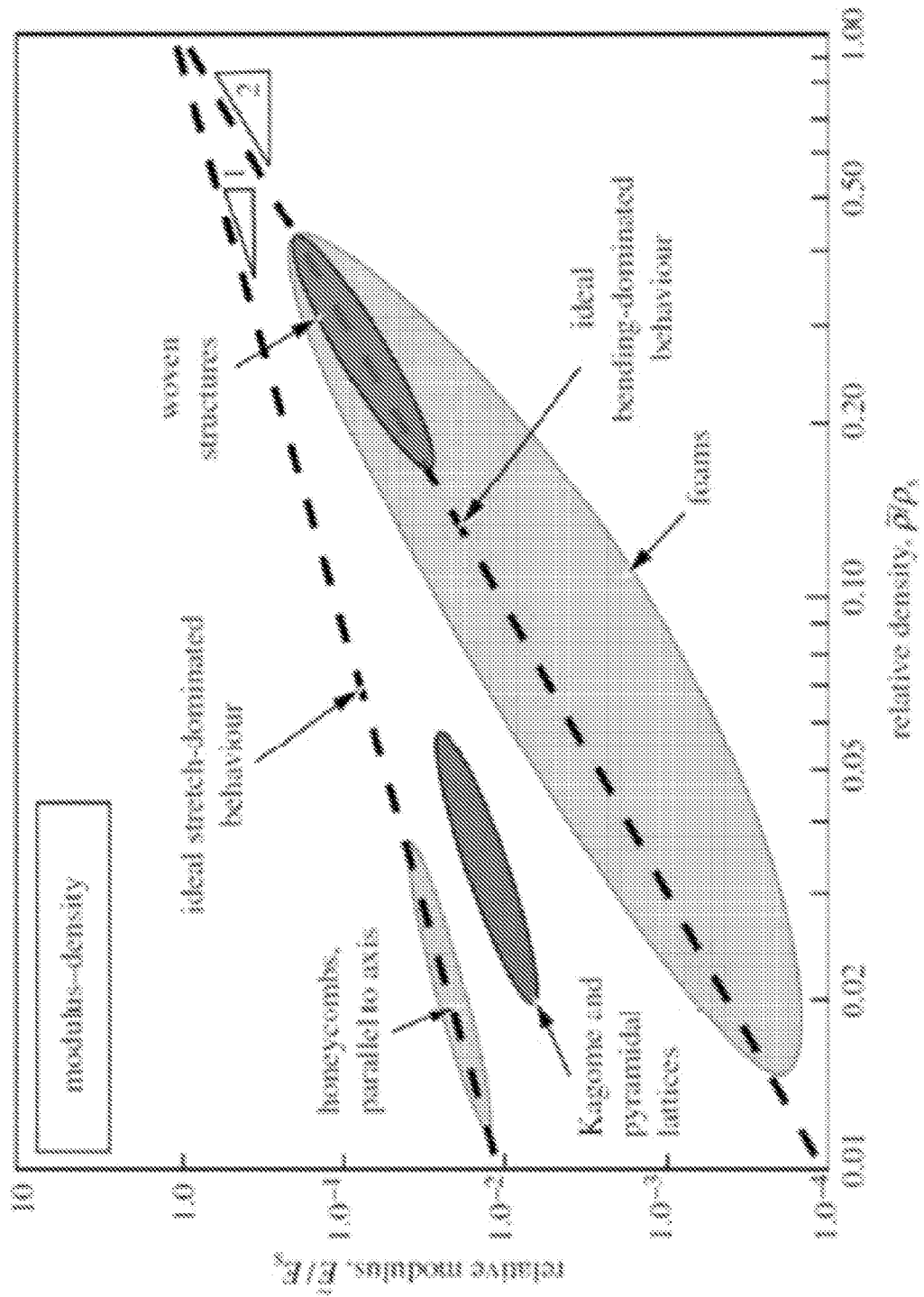
FIG. 47 is a chart of relative modulus vs. relative density, Gibson-Ashby model.
Figure 48:
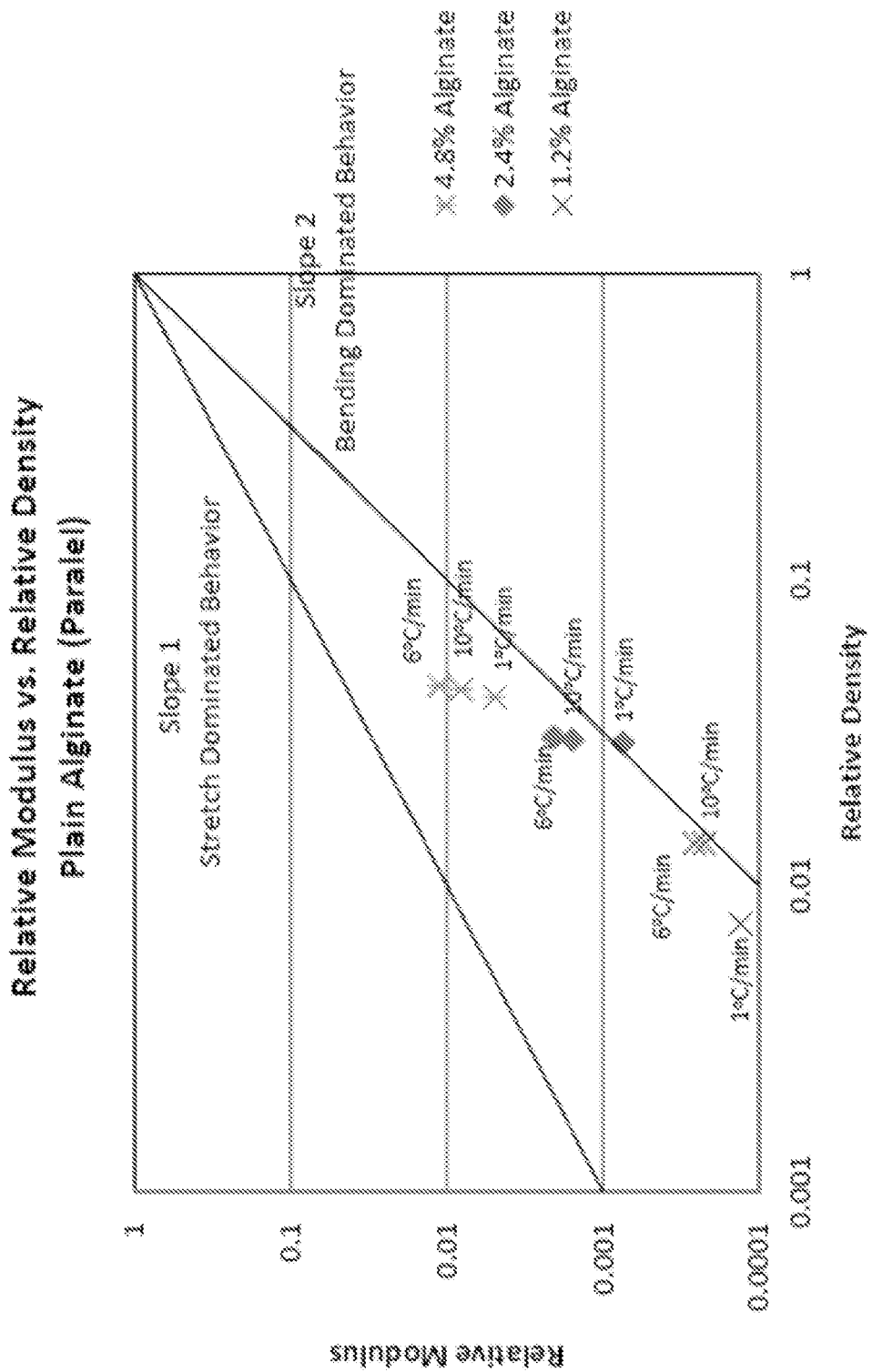
FIG. 48 is a chart of relative modulus vs. relative density (parallel to pores)

When analyzing the pore structure, there was a strong correlation between crosslinking agents and the structure. Aspect ratios decreased in samples that were fully gelled prior to freezing, but the samples that were crosslinked during freezing had similar aspect ratios to samples that were not crosslinked. As seen in FIG. 45, the alginate samples with that were fully gelled prior to freezing had smaller pore size than the samples that were not crosslinked and those that were crosslinked during freezing. The fully gelled calcium carbonate+GDL and 8 mMol calcium chloride samples had much smaller pore sizes compared with the other samples showing the effects of degree of crosslinking on pore size. The fully gelled calcium carbonate+GDL sample had a very interesting structure similar to styrofoam, in that it was somewhat brittle and had very small pores of homogenous size throughout the entire sample. The pores of the CaCO$_3$+GDL gelled samples were the closest looking to a honeycomb structure; all other samples had a more elongated pore structure.

Figure 43:
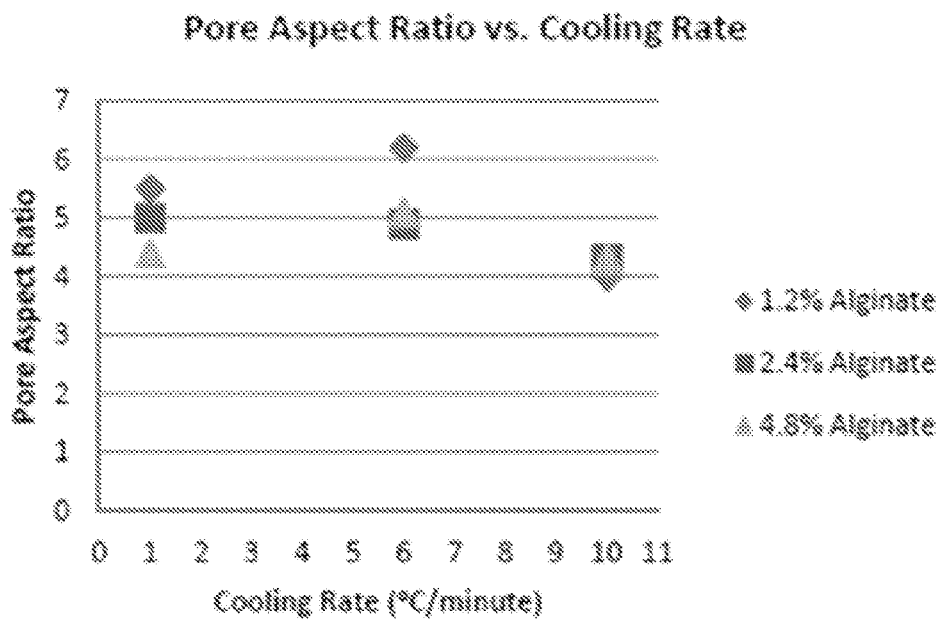
FIG. 43 is a chart of pore aspect ratio vs. cooling rate.

FIG. 43 shows pore aspect ratio slightly increases as cooling rate rises from 1° C./min to 6° C./min and then drops when the cooling rate rises again from 6° C./min to 10° C./min. The lower cooling rate produced the larger pore which resulted in the higher aspect ratio, as shown in Table 2.

Figure 44:
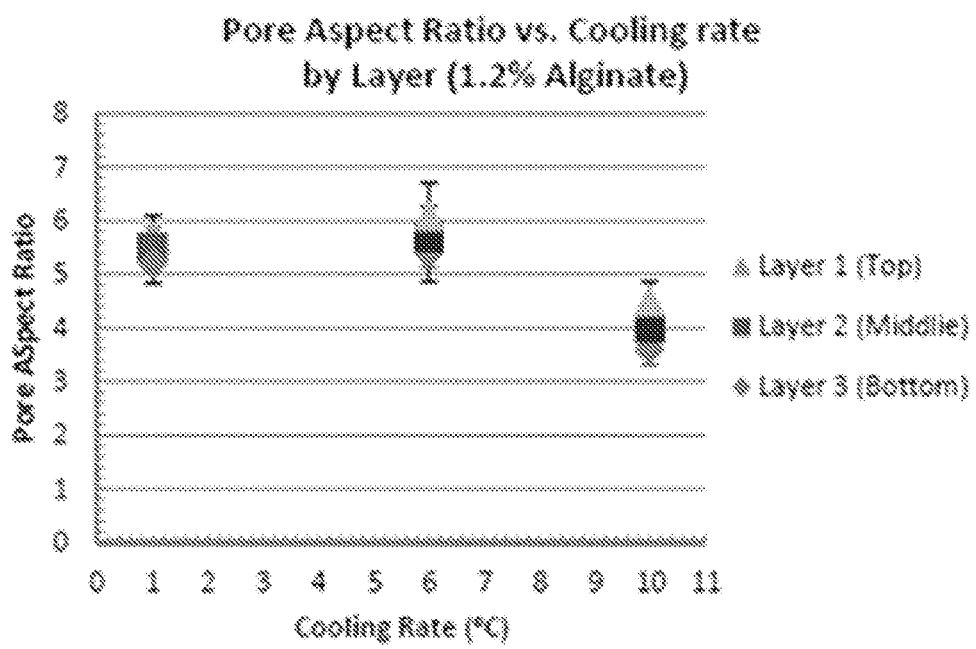
FIG. 44 is a chart of pore aspect ratio by layer vs. cooling rate.

In FIG. 44 it can be seen that the pore aspect ratio increases by layer as the distance from the bottom of the sample increases. The pore sizes varied with height in the sample in the non-crosslinked and L-phase samples. The pore sizes closest to the bottom of the sample were the smallest and so moving away from the bottom pore sizes increased by around 10 μm in each direction for each of the next two layers. There was near uniform pore size throughout the fully gelled samples. This is thought to be attributed to the crosslinking, by being fully crosslinked the polymer is stronger on a molecular level and is therefore not as easily moved to the side by the forming ice crystals. The crosslinking during freezing samples are thought to have the larger pores because the crosslinking process had not been completed. The calcium carbonate sample crosslinked during freezing and the 8 mMol CaCl$_2$ both had increased flexibility thought to be attributed to the crosslinkage. The discs cut for imaging and peeling were very flexible, and could be bent in half touching opposite sides together and they would return to the original shape and any pores that had been pressed closed reopened. A comparison of the two pores can be seen below.

A comparison to the properties of foams and lattices according to the model given by Gibson and Ashby was done. Based on the flexibility of the 88 mMol CaCl$_2$ and CaCO$_3$+GDL (during freezing crosslink) samples it is likely they will demonstrate bending dominated behavior. The CaCO$_3$+GDL fully gelled samples are brittle and were near impossible to peel because of it. These fully gelled samples will exhibit a buckling-dominated behavior. The non-cross linked samples should exhibit a bending-buckling-dominated behavior because they have some flexibility and the lamellae buckle when a load is applied. This was seen while trying to hold down a sample during the peeling process. A numerical, as shown in Table 3, and graphical comparison, as depicted in FIG. 47 through FIG. 52, was done for plain alginate. The model is based on equi-axed foams and very low aspect ratio honeycomb structures and pores and has become widely recognized and so a comparison was made. The model relates the properties of the porous samples to the bulk properties of a solid of the material used in the scaffold. The relative modulus is the modulus of the porous alginate scaffold created divided by the modulus of solid alginate, and the relative density is the scaffolds density divided by the density of solid alginate.

Figure 49:
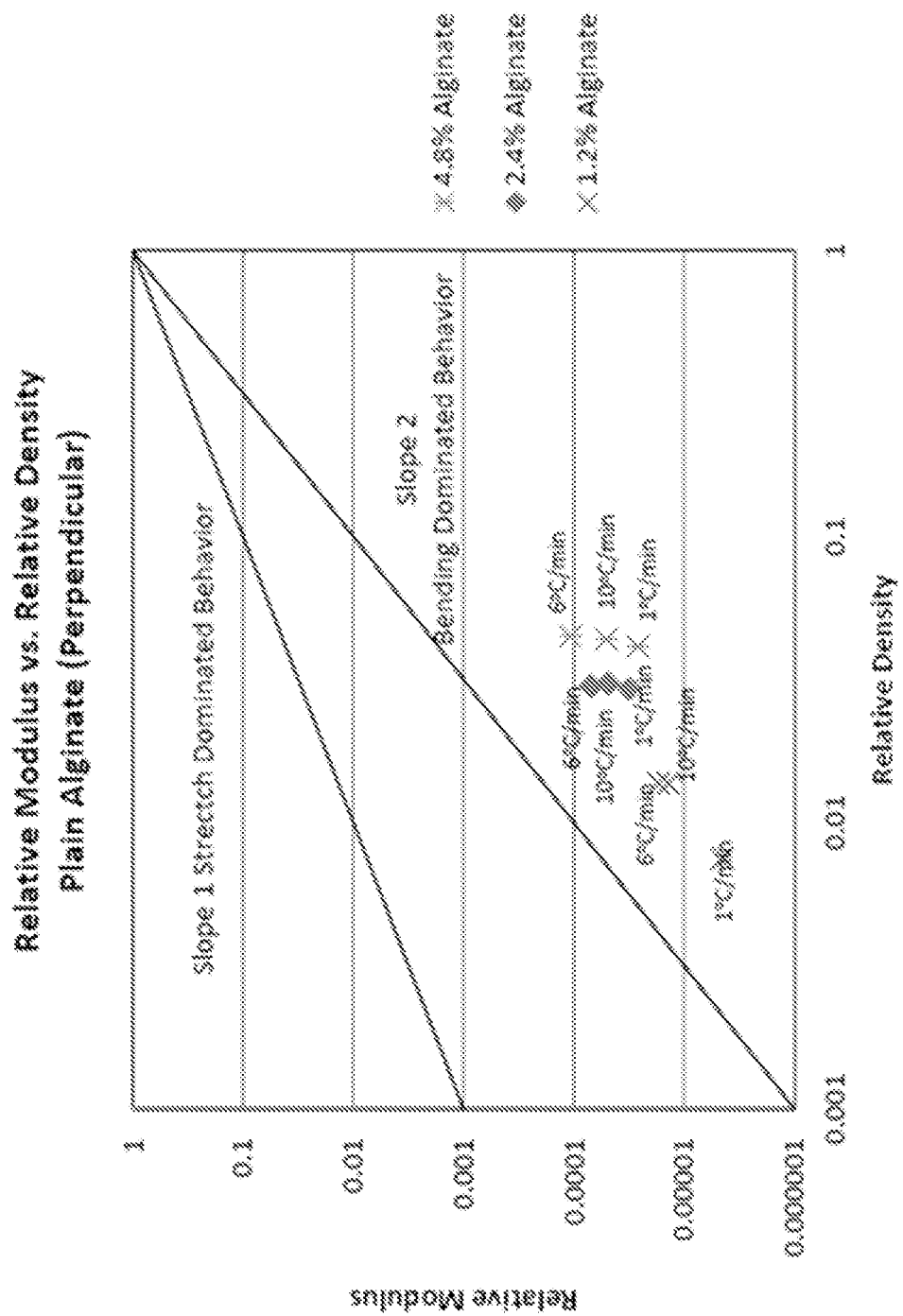
FIG. 49 is a chart of relative modulus vs. relative density (perpendicular to pores).
Figure 50:
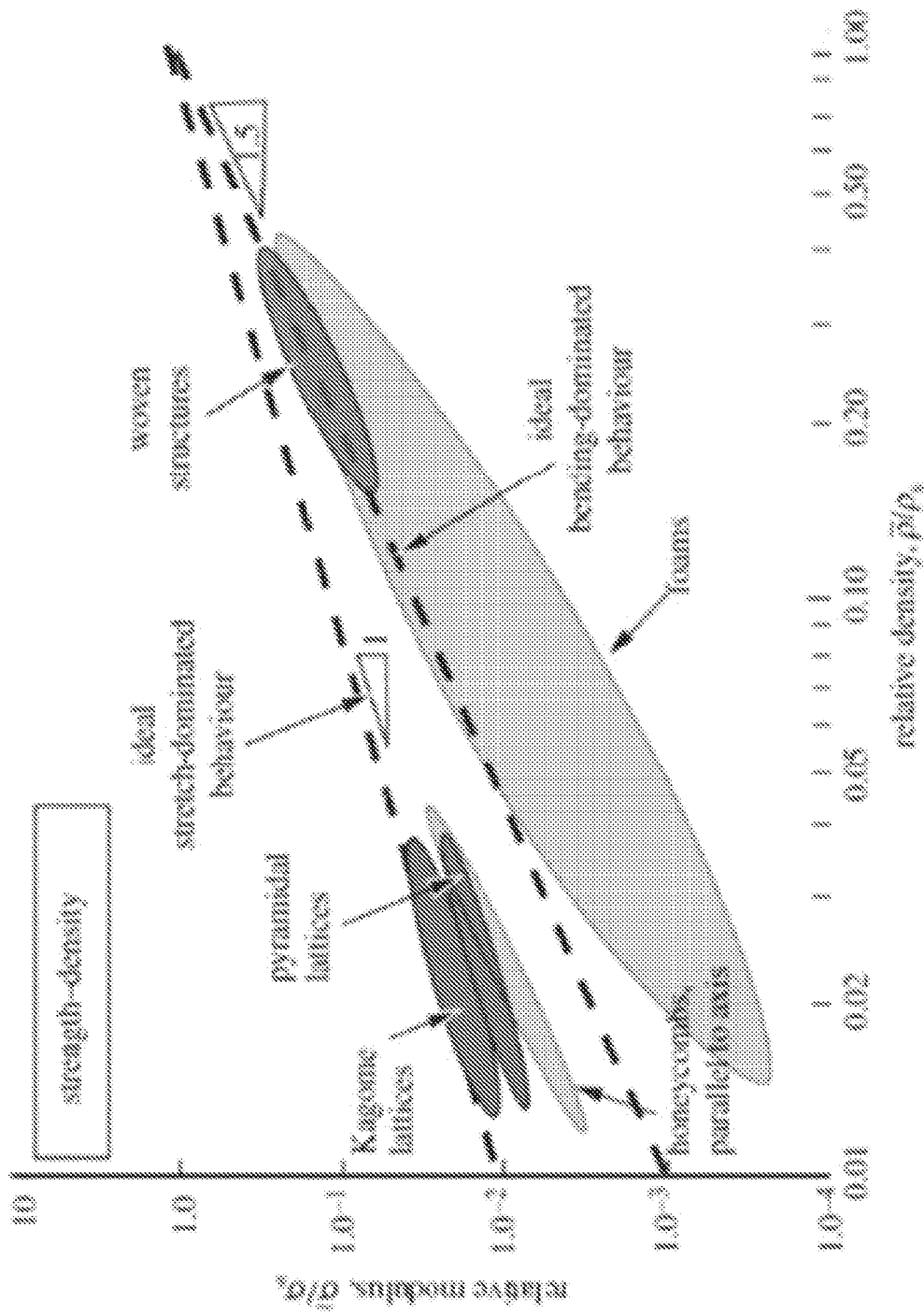
FIG. 50 is a chart of chart of relative strength vs. relative density, Gibson-Aschby Model.

The samples produced in the present experiment did not exactly match the model but were close as shown in FIGS. 49 through 52. Parallel to the pore direction, the samples from the present experiment are within the Gibson-Ashby model and the slopes are close to 1.4, when cooling rate is held constant. However, when cooling rate increases, the slopes become larger. Both of these trends can also be seen in the data from testing perpendicular to the pore direction, where the data points are just shifted down, as depicted in FIGS. 49 and 50. This is most likely due to the elongated nature and depth of the pores produced in these samples, some pores extended several millimeters axially. The slopes fall between the two models, which suggest there is a combination of bending and stretching behavior.

Figure 51:
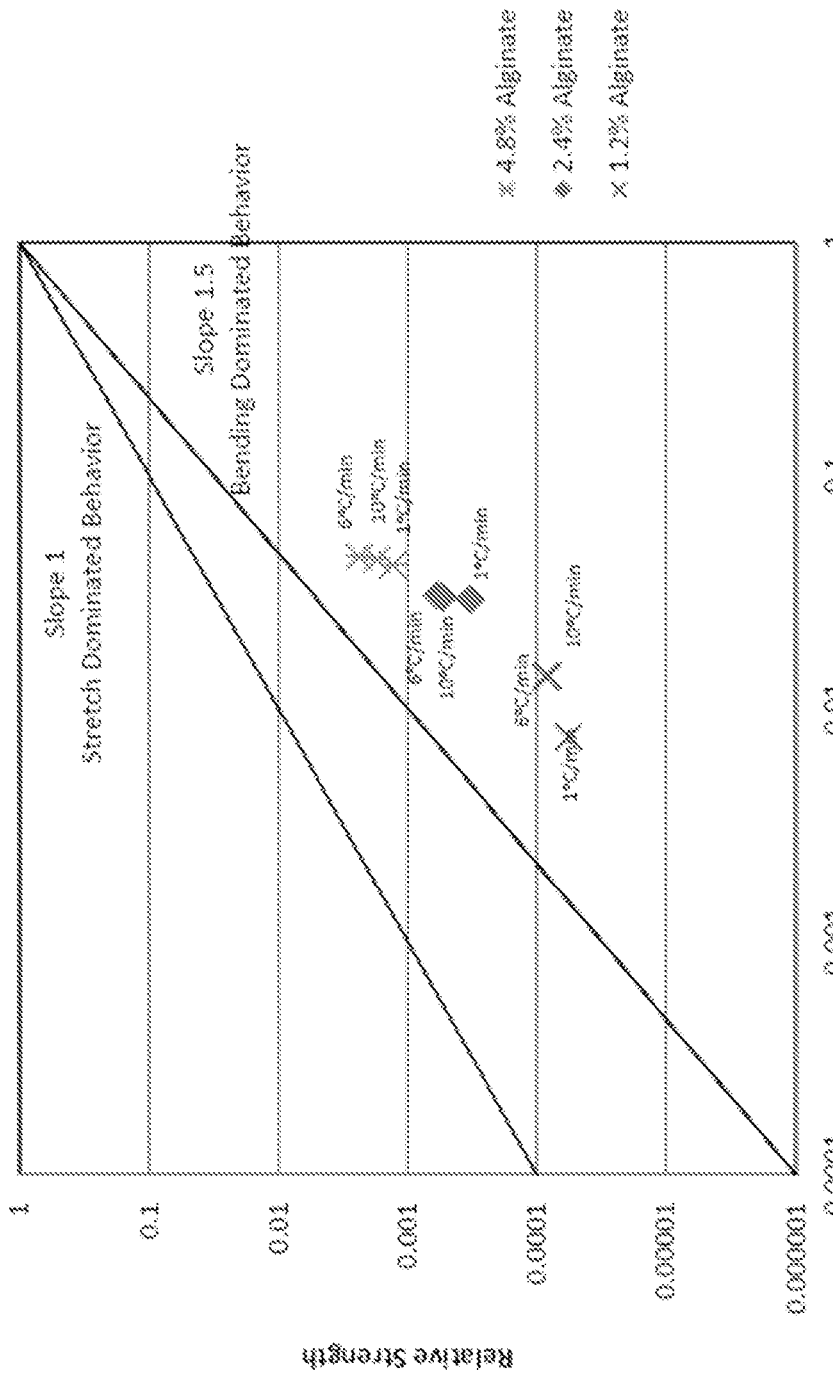
FIG. 51 is a chart of relative strength vs. relative density (parallel to pores) done for plain alginate.
Figure 52:
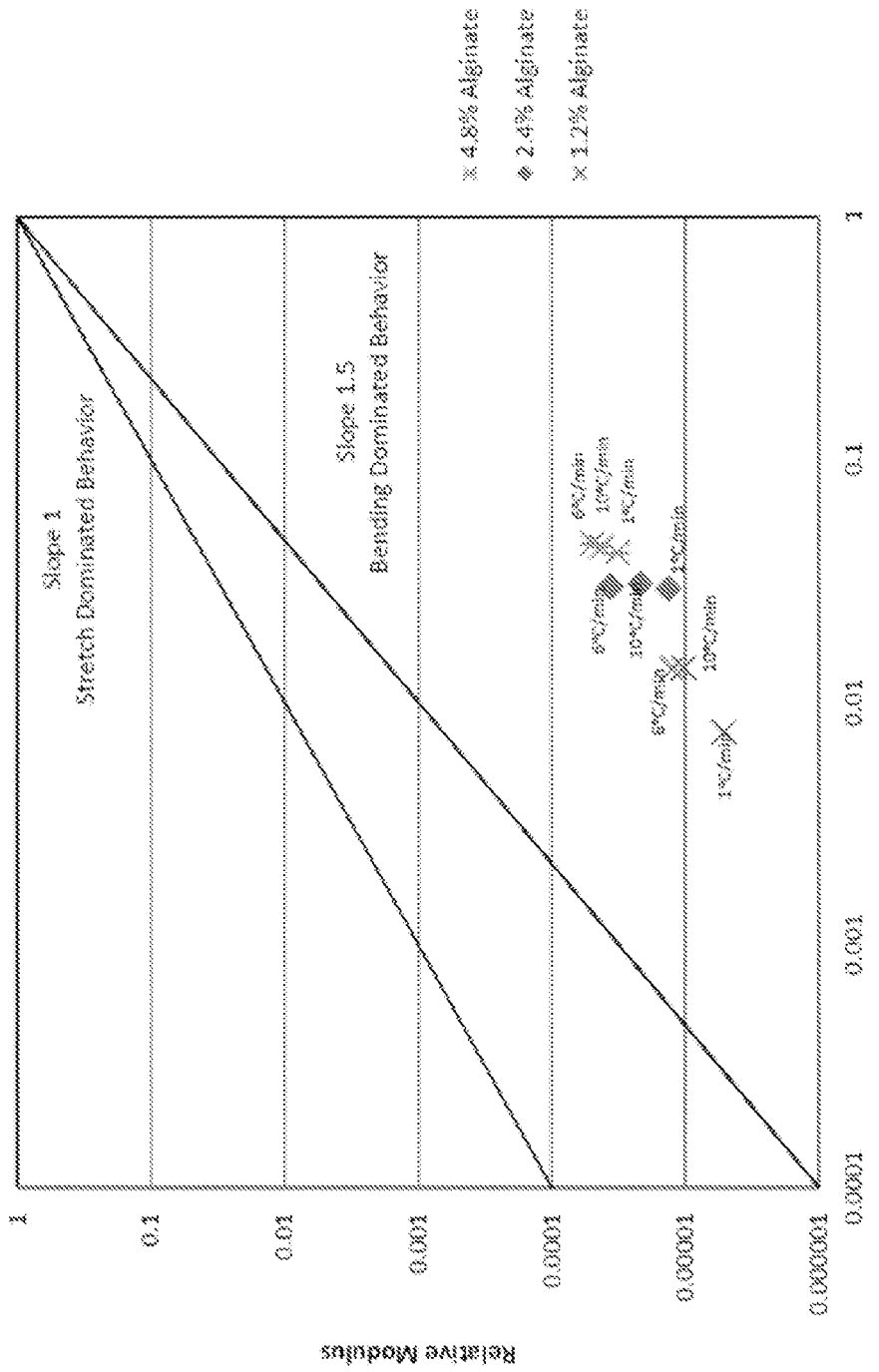
FIG. 52 is a chart of relative strength vs. relative density (perpendicular to pores) done for plain alginate.
Figure 53:
FIG. 53 is an image of DRG growing into microchannels.

FIGS. 51 and 52 show very similar trends to that of FIGS. 49 and 50, with the slopes close to that of that model when the cooling rate is held constant and the sharp increase in slope as cooling rate is increased in slope as cooling rate is increased for a single sample set.

In vitro testing was conducted by depositing DRGs from chick embryos onto 2D scaffolds (peelings). They were successful in attaching the DRG to the 2D scaffold and were able to image the nerve growth along the microchannels, as shown in FIG. 49.

Desired microchannel dimensions and mechanical properties were obtained and in vitro testing confirmed cells appear to attach to the scaffolds and the microchannels appear to effectively guide nerve growth, By increasing polymer concentration and the degree of crosslinking, the mechanical properties can be increased. A cooling rate of 6° C./min seemed optimal for higher mechanical properties. To alter microchannel dimensions, an increase of cooling rate will make them slightly more shallow and narrow. Pore sizes became smaller with increasing cooling rate and increased crosslinking; polymer concentration seemed to have much less of an effect.

Example 6

In Vitro Axonal Extension on an Ice-Templated, Linearly Aligned Chitosan-Alginate Scaffold Freeze casting, a directional solidification method that produces porous structures through ice templating, was successfully used to fabricate a chitosan-alginate scaffold with longitudinally aligned pores extending from end to end, as described herein. In addition to having compressive strength comparable to spinal cord tissue, the scaffold was able to support the attachment and growth of DRG axons in vitro, with surface adsorptions of a polycation and laminin synergistically promoting the maximum amount of axon growth. The data described herein show that this scaffold is useful as a physical guidance channel for the growth of regenerating axons in the injured spinal cord.

The materials and methods used in this example are now described.

Preparation of Chitosan-Alginate PEC Mixture

Chitosan (Sigma-Aldrich, MW approx. 50-190 kDa, 85% deacetylated) and sodium alginate (Protanal LF200M, MW approx. 270-325 kDa; FMC Biopolymer) were dissolved in 1% acetic acid and deionize water (DI), respectively, to produce separate 1.5% (w/v) solutions. Equal volumes of the chitosan and alginate solutions were added to a beaker (1.5% total polymer content) and the pH was adjusted to 7.4 with 6M sodium hydroxide. A homogeneous chitosan-alginate PEC mixture was produced by sonicating in an ice bath with 95 W applied power using a 20 kHz sonicator probe (CL4 tapped horn probe with 0.5" tip; Misonix Inc.) set to pulse for 2 minutes at 15 second intervals with a 3 second pause.

Fabrication of 3D Chitosan-Alginate Scaffold

The homogeneous chitosan-alginate PEC mixture was freeze cast into a three dimensional scaffold using the freeze casting system and method previously described [2010, Wegst et al., Philos Transact A Math Phys Eng Sci 368:2099-121]. Briefly, entrapped bubbles in the chitosan-alginate PEC mixture were removed by spinning at 2500 rpm for 1 minute in a shear mixer (SpeedMixer, DAC 1510 FVZ-K, FlackTek). The mixture was pipetted into a custom-built cylindrical polytetrafluoroethylene (PTFE) mold fitted with a copper bottom plate and secured onto the temperature-controlled copper cold finger of the freeze casting system. The cold finger temperature was lowered at a constant cooling rate of 1° C./min to a final temperature of −150° C., resulting in the directional solidification of the chitosan-alginate PEC dispersion. After the samples were frozen, they were removed from the molds and lyophilized until dry. Dried chitosan-alginate scaffolds (chitosan-alginate scaffolds) were stored in a desiccator at room temperature until use.

Preparation of Chitosan-Alginate Scaffolds for In Vitro Cell Culture

The dried scaffolds were cut into cube-shaped samples (3 mm×3 min longitudinally, 1 mm depth cross-section) using a sterile scalpel blade. The samples were then crosslinked with a 0.25% calcium chloride ($CaCl_2$) solution for 10 minutes and washed in phosphate buffered saline (PBS) prior to surface adsorption of polycations or laminin. For polycation adsorption, chitosan-alginate scaffolds were submerged in 3 ml of a 0.5 mg/mL solution of poly-L-lysine (PLL, Sigma-Aldrich, insert MW) or poly-L-ornithine (PLO, Sigma-Aldrich, insert MW) for 6 minutes at room temperature with gentle shaking and then washed 3 times in 3 ml PBS. This was followed by adsorption of laininin (Sigma-Aldrich) overnight at 37° C. (200 µl 100 mg/mL solution in PBS) and further washing with PBS before in vitro cell culture.

Mechanical Testing

Chitosan-alginate scaffolds were mounted on ceramic discs with Crystalbond 509 (Aremco Products, Inc) and sectioned with a 220 µm diameter diamond-decorated steel wire on a Well 4240 saw (WELL Diamond Wire Saws, Inc) at a wire speed of 0.7 m/s. Sample cubes (5×5×5 mm) were sectioned from each scaffold, cutting four cubes from three separate layers. Mechanical testing was performed on an Instron Model 4442 single-column bench-top machine using a 50 N load cell for dry scaffold testing and a 5 N load cell for wet scaffold testing (after crosslinking in $CaCl_2$, testing performed on samples saturated in PBS). The sample cubes were compressed in the axial direction with a cross-head speed of 0.05 minis, with the load parallel to the linearly oriented pores. The data obtained was used to generate stress-strain curves and derive the elastic modulus and plateau strength of the samples.

Dorsal Root Ganglia Isolation and Culture

Dorsal root ganglia (DRGs) were isolated from embryonic day 10 (E10) chick embryos (Charles River) and collected in sterile Hank's Buffered Saline Solution (Mediatech). Whole DRG explants were seeded onto a cross-sectional surface of the scaffold and incubated in growth medium (Dulbecco's modified Eagle medium (DMEM), 10% fetal bovine serum (FBS), 1% antibiotic, and 100 ng/ml nerve growth factor (NGF)) at 37° C. and 5% $CO_2$. Explants were cultured for 72 hours in vitro prior to immunocytochemical analysis.

Immunocytochemistry

After removal of the medium, DRG-seeded scaffolds were fixed in 4% paraformaldehyde for 30 minutes at room temperature and washed three times in PBS. The fixed cells were blocked in 0.1% Triton X-100 with 10% normal goat serum in PBS for 1 hour at room temperature, followed by an overnight incubation at 4° C. in blocking solution containing mouse monoclonal antibody anti-neurofilament 200 kDa (Sigma; 1:500). The cells were washed three times in PBS and the secondary antibody Alexa Fluor 488 goat anti-mouse IgG (Invitrogen; 1:500) was applied for 1 hour at room temperature. DRG-seeded scaffolds were visualized and images were captured using an Olympus 1×81 confocal microscope. A z-stack over approximately 20 sections of 10 µm thickness was performed, and single layers were merged into one image using FluoView software.

Scanning Electron Microscopy (SEM)

Dry, uncrosslinked chitosan-alginate scaffolds needed no additional preparation for SEM and were directly mounted onto aluminum stubs. Crosslinked chitosan-alginate scaffolds were washed thoroughly in deionized water, then frozen at −80° C. and lyophilized, before mounting on stubs. All specimens were sputter coated with a 3 inn thick layer of platinum-palladium and loaded into a Zeiss Supra 50VP SEM (Carl Zeiss SMT Inc.). Imaging was performed with an accelerating voltage of 6 kV at a working distance of 5 mm.

Statistical Analysis

Statistical analysis was performed with GraphPad Prism 5 (GraphPad Software) software. One-way analysis of variance (ANOVA) and Tukey-Kramer post-tests were performed for quantitative analysis of DRG axon elongation. A priori confidence intervals of 95% were used for the post hoc test results. Results are shown with SEM.

The results of this example are now described.

Scaffold Microstructure

Freeze casting, or directional solidification, produced 3D chitosan-alginate scaffolds with a linearly aligned, highly porous microstructure. Characterization of the dry scaffolds with SEM indicated an average channel width of 69±5.8 µm (range from approximately 60 to 80 µm), with channels extending longitudinally throughout the entire length of the scaffold (FIG. 54). The smooth surface and channel walls were shown to be connected via bridging and small fenestrations throughout the scaffold. The chitosan-alginate scaffolds also maintained their porous structure after crosslinking with $CaCl_2$ and immersion in aqueous medium, visible in FIG. 55. Some distortion can be seen in the structure due to hydration and re-freezing. The average channel width after crosslinking was 68±5.7 µm (range from approximately 60 to 80 µm). When the pH of the chitosan-alginate PEC mixture was not adjusted prior to freeze casting (pH approximately 4.35), the resulting scaffold was porous, but lacked a linearly aligned structure and continuous channels extending longitudinally through the full length of the scaffold. Light micrographs of this structure are shown in FIG. 56, comparing the cross-section of the scaffold resulting from the pH-adjusted chitosan-alginate PEC mixture and the non-pH-adjusted mixture.

Scaffold Surface Charge and Mechanical Properties

To assess the mechanical properties of the crosslinked, hydrated scaffolds, compression tests were performed to determine the elastic modulus. It was observed that the elastic modulus of the scaffolds was 5.08±0.61 kPa. Reported Young's modulus values for the spinal cord range greatly from approximately 3 kPa to 300 kPa depending on the presence or absence of meninges on the tested samples [2010, Straley et al., 1 Neurotrauma 27: 1-19], but the modulus of the chitosan-alginate scaffolds is close to the 3-5 kPa reported for isolated white and grey matter (no meninges present), indicating that the scaffold has mechanical characteristics comparable to that of native tissue [2001, Ozawa et al., J Neurosurg 95(2 Suppl):221-224].

In Vitro DRG Axonal Outgrowth

The 3D chitosan-alginate scaffolds were evaluated for their ability to support in vitro axonal extension using chick DRG explants. The explants were seeded directly onto the cross-sectional surface of the scaffolds, so that axons would be able to penetrate into the longitudinal channels. Prior to seeding with DRGs, polycations (PLO or PLL) and/or laminin were adsorbed on the scaffold surface to determine their effects on the promotion of axon outgrowth in the chitosan-alginate scaffolds.

DRGs adhered to the scaffold surfaces with or without polycation and/or laminin adsorption and extended axons in parallel alignment with the channel direction. It was necessary to fluorescently label the DRG axons in order to visualize their presence since the chitosan-alginate scaffolds were opaque, and fluorescently labeled axons could be observed after 24 hours.

Axon outgrowth on the scaffolds was quantified (FIG. 56) to reveal that the greatest length of axonal penetration was achieved with scaffold surface adsorption using a combination of polycation and laminin (mean axon length: 793.2±187.2 µm for PLO+laminin, 768.7±241.2 µm for PLL+laminin). There was no significant difference in axon length between use of PLO and PLL (p>0.05). The combination of polycation and laminin surface adsorption worked in synergy to promote significantly longer axons than the sum of individual scaffold surface treatments investigated here (p<0.001). Axon growth on scaffolds coated with a polycation alone (mean axon length: 36.92±65.71 µm for PLO, 53.19±92.13 µm for PLL), showed no statistical difference between polycation types (p>0.05). Axon growth on scaffolds coated with laminin alone was significantly longer than that on the uncoated scaffolds (mean axon length: 482.9±170.3 mm for laminin alone, 22.52±50.14 µm for uncoated scaffolds, p<0.001), but still significantly shorter than on scaffolds that received polycation+laminin surface adsorption. Representative confocal images of DRG-seeded scaffolds from each experimental group are shown in FIG. 58.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A scaffold for supporting cell growth, the scaffold comprising regions of aligned pores, wherein at least some walls of the pores include ridges that protrude from the walls and run parallel to a long axis of the pores.

2. The scaffold of claim 1, wherein the scaffold comprises a polymer.

3. The scaffold of claim 2, wherein the polymer comprises at least one selected from the group consisting of: chitosan, chitin, cellulose, alginate, agar, gelatin, soy protein, hyaluronic acid, collagen, elastin, and silk, and any combination thereof.

4. The scaffold of claim 2, wherein the modulus of the scaffold is controlled in the kPa to GPa range.

5. The scaffold of claim 2, wherein the strength of the scaffold is controlled in the kPa to GPa range.

6. The scaffold of claim 2, wherein the toughness and fracture toughness of the scaffold and scaffold forming material is controlled in the $J/m^3$ to $MJ/m^3$, and in the $kPa \cdot m^{1/2}$ to $MPa \cdot m^{1/2}$ range, respectively.

7. The scaffold of claim 1, wherein substantially parallel grooves are formed between adjacent ridges.

8. The scaffold of claim 7, wherein the width of each groove is controlled in a micrometer to nanometer length scale.

9. The scaffold of claim 1, wherein the formation of the height and width of each ridge is controlled in a micrometer to nanometer length scale.

10. The scaffold of claim 1, wherein the ridges have substantially rectangular profiles.

11. The scaffold of claim 1, wherein adjacent ridges are separated by between about 1 µm and about 50 µm.

12. The scaffold of claim 1, wherein the ridges have a height between about 6 µm and about 11 µm.

* * * * *